United States Patent
Gephart et al.

(10) Patent No.: US 8,551,141 B2
(45) Date of Patent: Oct. 8, 2013

(54) MINIMALLY INVASIVE SURGICAL SYSTEM

(75) Inventors: Matthew P. Gephart, Marquette, MI (US); Phillip J. Berman, Jacksonville, FL (US); John White, Marquette, MI (US); John Kovarik, Negaunee, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 586 days.

(21) Appl. No.: 12/438,538

(22) PCT Filed: Aug. 23, 2007

(86) PCT No.: PCT/US2007/076687
§ 371 (c)(1),
(2), (4) Date: Aug. 23, 2010

(87) PCT Pub. No.: WO2008/024937
PCT Pub. Date: Feb. 28, 2008

(65) Prior Publication Data
US 2010/0312279 A1   Dec. 9, 2010

Related U.S. Application Data

(60) Provisional application No. 60/839,895, filed on Aug. 23, 2006.

(51) Int. Cl.
*A61B 17/56* (2006.01)

(52) U.S. Cl.
USPC .................... 606/246; 606/86 A; 606/279

(58) Field of Classification Search
USPC ........... 606/246, 264–272, 279, 301, 99, 104, 606/86 A
See application file for complete search history.

(56) References Cited

U.S. PATENT DOCUMENTS

| 3,844,291 A | 10/1974 | Moen |
| 5,020,519 A | 6/1991 | Hayes et al. |
| 5,171,279 A | 12/1992 | Mathews |

(Continued)

FOREIGN PATENT DOCUMENTS

| EP | 1858422 | 11/2008 |
| WO | WO 2004047650 | 6/2004 |
| WO | WO 2008024937 | 2/2008 |

OTHER PUBLICATIONS

Foley, M.D., Kevin T., Schwender, MD., James D., and Rouben, MD., David P., Pyrametrix® Advance: Instrument Set Technique, surgical technique brochure provided by the manufacturer, Medtronic Sofamore Danek Inc., 2005.

(Continued)

*Primary Examiner* — Pedro Philogene
*Assistant Examiner* — David Comstock
(74) *Attorney, Agent, or Firm* — Fitch, Even, Tabin & Flannery LLP

(57) ABSTRACT

A multi-stage minimally invasive surgical procedure and associated instruments are disclosed. First, the surgical site is prepared. After preparation, the bone screws or anchors are attached to the bone. Subsequent to insertion of the screws, a rod or connecting member is positioned within the yoke portion of the bone screw. Caps are then placed in a pre-lock position within the yokes. The bone screws may be compressed together or distracted along the rod or connecting member, thereby setting the final spacing of the bones or bone segments. Finally the caps are moved to a final lock position to fix the screws to the rod or connecting member to maintain the bones in position relative to each other.

19 Claims, 77 Drawing Sheets

(56) References Cited

U.S. PATENT DOCUMENTS

| | | |
|---|---|---|
| 5,242,443 A | 9/1993 | Kambin |
| 5,258,005 A | 11/1993 | Christian et al. |
| 5,507,772 A | 4/1996 | Shutt et al. |
| 5,683,392 A | 11/1997 | Richelsoph et al. |
| 5,720,751 A | 2/1998 | Jackson |
| 5,782,833 A | 7/1998 | Haider |
| 5,863,293 A | 1/1999 | Richelsoph |
| 5,941,885 A | 8/1999 | Jackson |
| 5,954,635 A | 9/1999 | Foley et al. |
| 5,964,760 A | 10/1999 | Richelsoph |
| 5,964,761 A | 10/1999 | Kambin |
| 6,010,503 A | 1/2000 | Richelsoph |
| 6,090,111 A | 7/2000 | Nichols |
| 6,096,044 A | 8/2000 | Boyd et al. |
| 6,132,432 A | 10/2000 | Richelsoph |
| 6,174,311 B1 | 1/2001 | Branch et al. |
| 6,226,548 B1 | 5/2001 | Foley et al. |
| 6,287,313 B1 | 9/2001 | Sasso |
| 6,355,040 B1 | 3/2002 | Richelsoph et al. |
| 6,440,133 B1 | 8/2002 | Beale et al. |
| 6,485,491 B1 | 11/2002 | Farris et al. |
| 6,485,591 B1 | 11/2002 | Nakao et al. |
| 6,530,929 B1 | 3/2003 | Justis et al. |
| 6,565,565 B1 | 5/2003 | Yuan et al. |
| 6,648,888 B1 | 11/2003 | Shluzas |
| 6,660,006 B2 | 12/2003 | Markworth et al. |
| 6,666,866 B2 | 12/2003 | Martz et al. |
| 6,749,614 B2 | 6/2004 | Teitelbaum et al. |
| 6,755,829 B1 | 6/2004 | Bono et al. |
| 6,793,656 B1 | 9/2004 | Mathews |
| 6,875,212 B2 | 4/2005 | Shaolian et al. |
| 6,951,538 B2 | 10/2005 | Ritland |
| 6,964,667 B2 | 11/2005 | Shaolian et al. |
| 7,011,660 B2 | 3/2006 | Sherman et al. |
| 7,081,117 B2 | 7/2006 | Bono et al. |
| 7,083,621 B2 | 8/2006 | Shaolian et al. |
| 7,090,674 B2 | 8/2006 | Doubler |
| 7,125,426 B2 | 10/2006 | Bono et al. |
| 7,141,051 B2 | 11/2006 | Janowski et al. |
| 7,476,240 B2 | 1/2009 | Raymond et al. |
| 2002/0120272 A1 | 8/2002 | Yuan et al. |
| 2002/0161368 A1 | 10/2002 | Foley et al. |
| 2003/0060826 A1 | 3/2003 | Foley et al. |
| 2003/0073998 A1 | 4/2003 | Pagliuca et al. |
| 2003/0125742 A1 | 7/2003 | Yuan |
| 2003/0208203 A1 | 11/2003 | Lim et al. |
| 2003/0225408 A1 | 12/2003 | Nichols et al. |
| 2003/0229347 A1 | 12/2003 | Sherman et al. |
| 2003/0236447 A1 | 12/2003 | Ritland |
| 2004/0039384 A1 | 2/2004 | Boehm, Jr. et al. |
| 2004/0059333 A1 | 3/2004 | Carl et al. |
| 2004/0082960 A1 | 4/2004 | Davison |
| 2004/0092952 A1 | 5/2004 | Newton et al. |
| 2004/0133201 A1 | 7/2004 | Shluzas et al. |
| 2004/0138662 A1 | 7/2004 | Landry et al. |
| 2004/0143265 A1 | 7/2004 | Landry et al. |
| 2004/0147937 A1 | 7/2004 | Dunbar, Jr. et al. |
| 2004/0172022 A1 | 9/2004 | Landry et al. |
| 2004/0215190 A1 | 10/2004 | Nguyen et al. |
| 2004/0230100 A1 | 11/2004 | Shluzas |
| 2004/0230191 A1 | 11/2004 | Frey et al. |
| 2005/0004519 A1 | 1/2005 | Torode et al. |
| 2005/0004593 A1 | 1/2005 | Simonson |
| 2005/0021030 A1 | 1/2005 | Pagliuca et al. |
| 2005/0021031 A1 | 1/2005 | Foley et al. |
| 2005/0033297 A1 | 2/2005 | Davison |
| 2005/0033299 A1 | 2/2005 | Shluzas |
| 2005/0065516 A1 | 3/2005 | Jahng |
| 2005/0065517 A1 | 3/2005 | Chin |
| 2005/0075540 A1 | 4/2005 | Shluzas et al. |
| 2005/0075644 A1 | 4/2005 | Dipoto |
| 2005/0080418 A1 | 4/2005 | Simonson et al. |
| 2005/0085813 A1 | 4/2005 | Spitler et al. |
| 2005/0090822 A1 | 4/2005 | DiPoto |
| 2005/0090824 A1 | 4/2005 | Shluzas et al. |
| 2005/0090833 A1 | 4/2005 | Dipoto |
| 2005/0090899 A1 | 4/2005 | Dipoto |
| 2005/0107789 A1 | 5/2005 | Sweeny |
| 2005/0131408 A1 | 6/2005 | Sicvol et al. |
| 2005/0131419 A1 | 6/2005 | McCord et al. |
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0137593 A1 | 6/2005 | Gray et al. |
| 2005/0149022 A1 | 7/2005 | Shaolian et al. |
| 2005/0149036 A1 | 7/2005 | Varieur et al. |
| 2005/0149053 A1 | 7/2005 | Varieur et al. |
| 2005/0154389 A1 | 7/2005 | Selover et al. |
| 2005/0159651 A1 | 7/2005 | Raymond et al. |
| 2005/0171540 A1 | 8/2005 | Lim et al. |
| 2005/0171551 A1 | 8/2005 | Sukovich et al. |
| 2005/0192570 A1 | 9/2005 | Jackson |
| 2005/0192579 A1 | 9/2005 | Jackson |
| 2005/0192589 A1 | 9/2005 | Raymond et al. |
| 2005/0215999 A1 | 9/2005 | Birkmeyer |
| 2005/0216002 A1 | 9/2005 | Simonson |
| 2005/0228380 A1 | 10/2005 | Moore |
| 2005/0228400 A1 | 10/2005 | Chao et al. |
| 2005/0251192 A1 | 11/2005 | Shluzas et al. |
| 2005/4245942 | 11/2005 | Dipoto |
| 2005/0273131 A1 | 12/2005 | Shluzas et al. |
| 2005/0273132 A1 | 12/2005 | Shluzas et al. |
| 2005/0273133 A1 | 12/2005 | Shluzas et al. |
| 2005/0288671 A1 | 12/2005 | Yuan et al. |
| 2006/0036244 A1 | 2/2006 | Spitler et al. |
| 2006/0074445 A1 | 4/2006 | Gerber et al. |
| 2006/0089651 A1 | 4/2006 | Trudeau et al. |
| 2006/0111714 A1 | 5/2006 | Foley |
| 2006/0155278 A1 | 7/2006 | Warnick |
| 2006/0173456 A1 | 8/2006 | Hawkes et al. |
| 2006/0200135 A1 | 9/2006 | Sherman et al. |
| 2006/0229614 A1 | 10/2006 | Foley et al. |
| 2006/0235393 A1 | 10/2006 | Bono et al. |
| 2006/0241600 A1 | 10/2006 | Ensign et al. |
| 2006/0247630 A1 | 11/2006 | Lott et al. |
| 2006/0247636 A1 | 11/2006 | Yuan et al. |
| 2006/0264962 A1 | 11/2006 | Chin et al. |
| 2006/0276791 A1 | 12/2006 | Shluzas |
| 2006/0276792 A1 | 12/2006 | Ensign et al. |
| 2007/0055235 A1 | 3/2007 | Janowski et al. |
| 2007/0078460 A1 | 4/2007 | Frigg et al. |
| 2007/0093817 A1 | 4/2007 | Barrus et al. |
| 2007/0093826 A1 | 4/2007 | Hawkes et al. |
| 2007/0093827 A1 | 4/2007 | Warnick |
| 2007/0185491 A1 | 8/2007 | Foley et al. |
| 2007/0198015 A1 | 8/2007 | Foley et al. |
| 2007/0225711 A1 | 9/2007 | Ensign |
| 2008/0039839 A1 | 2/2008 | Songer et al. |
| 2008/0039840 A1 | 2/2008 | Songer et al. |
| 2008/0045956 A1 | 2/2008 | Songer et al. |
| 2008/0154277 A1 | 6/2008 | Machalk et al. |
| 2008/0195155 A1 | 8/2008 | Hoffman et al. |
| 2008/0228233 A1 | 9/2008 | Hoffman et al. |
| 2009/0228054 A1 | 9/2009 | Hoffman et al. |
| 2010/0160977 A1 | 6/2010 | Gephart |

OTHER PUBLICATIONS

International Search Report and Written Opinion for PCT/US2006/06684, dated Sep. 20, 2007.

International Search Report and Written Opinion for PCT/US2007/76687, dated Sep. 22, 2008.

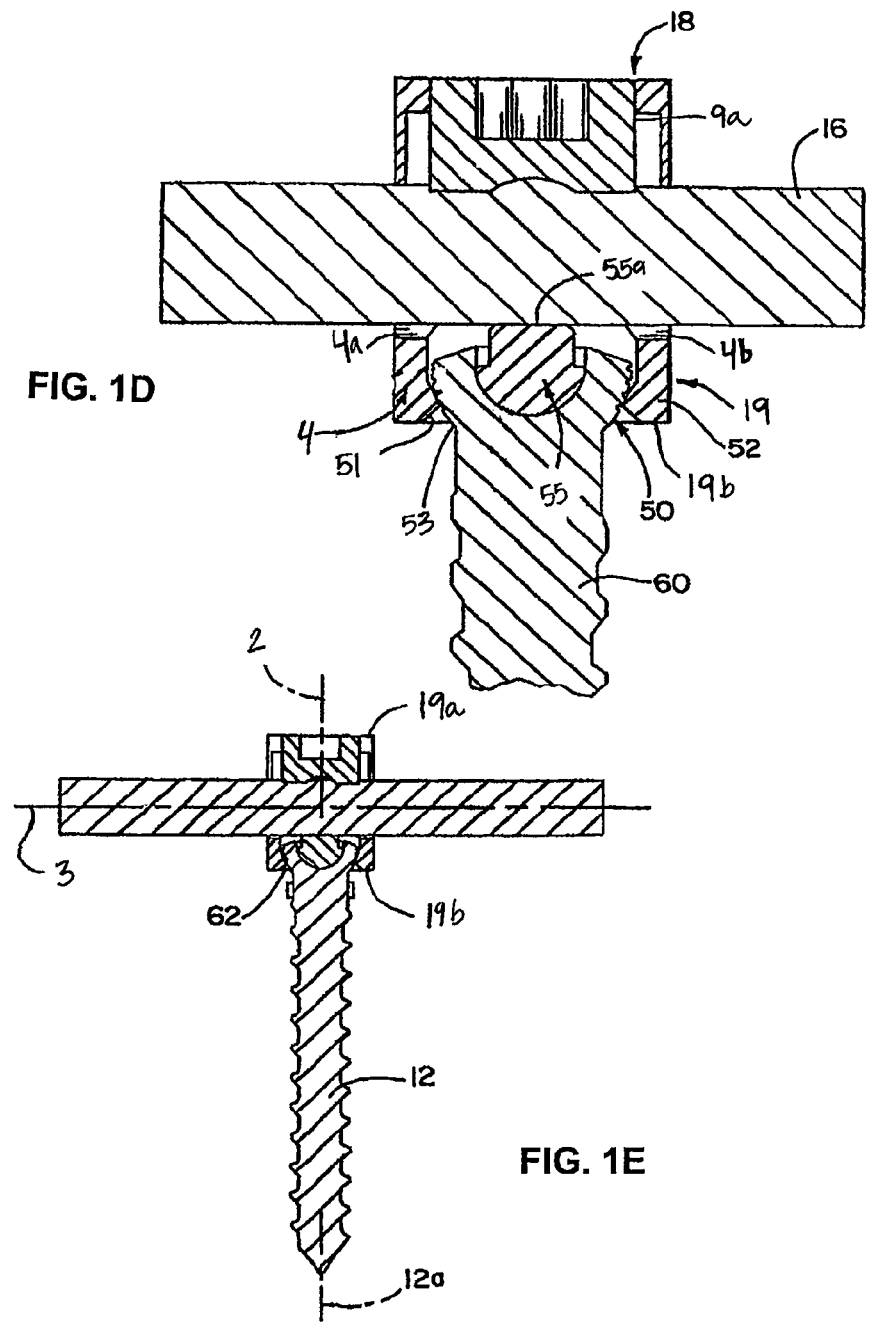

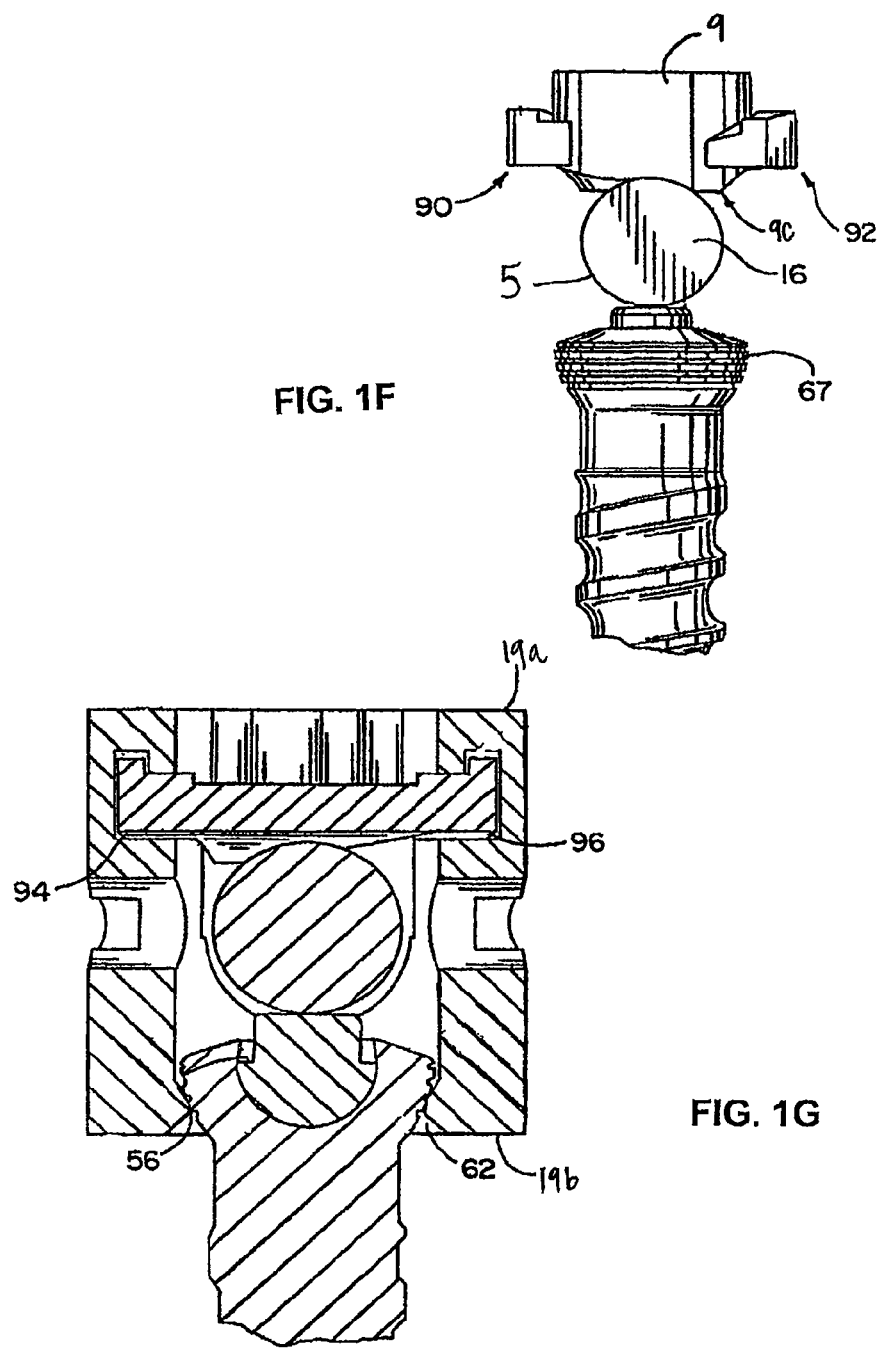

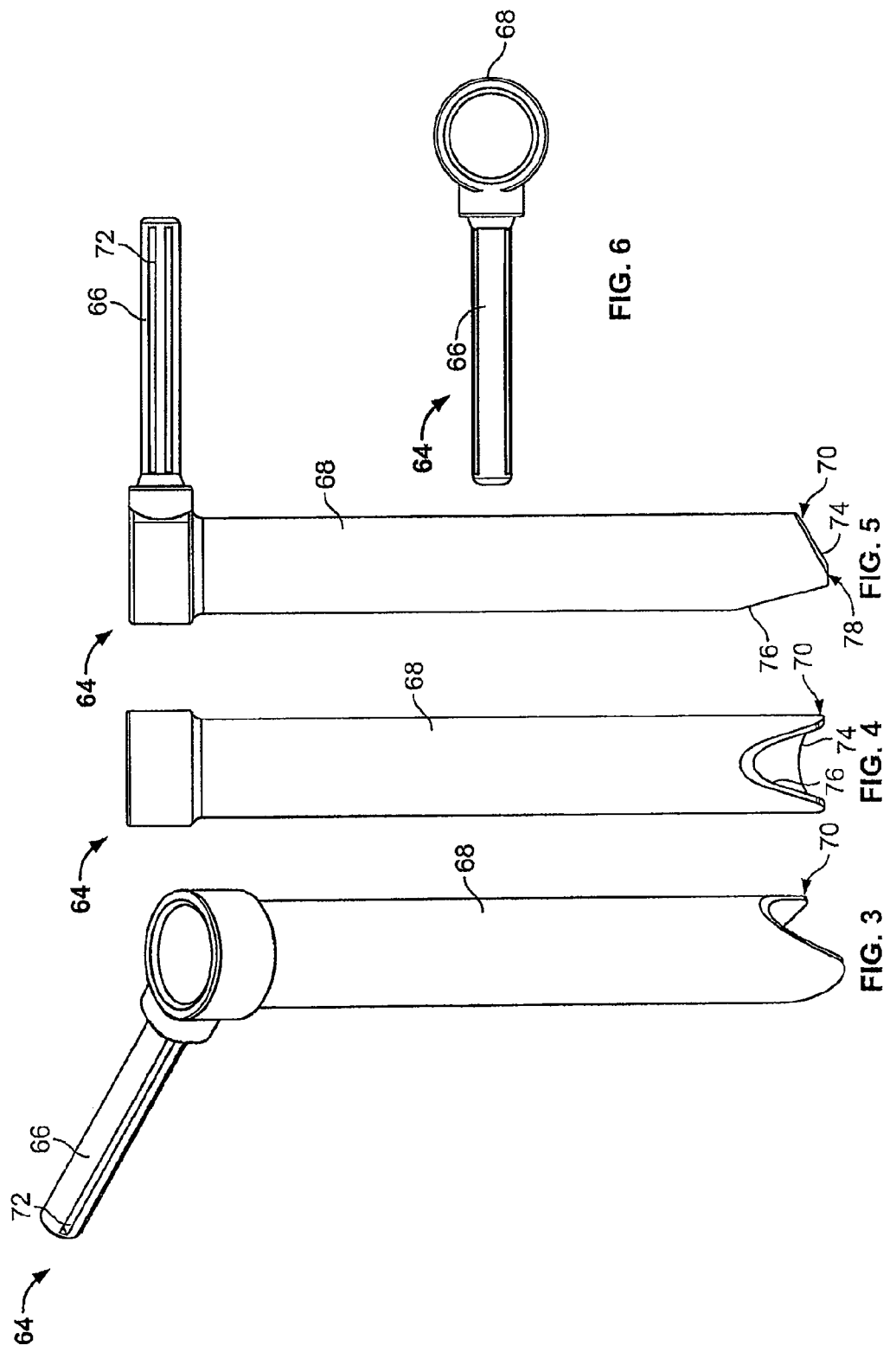

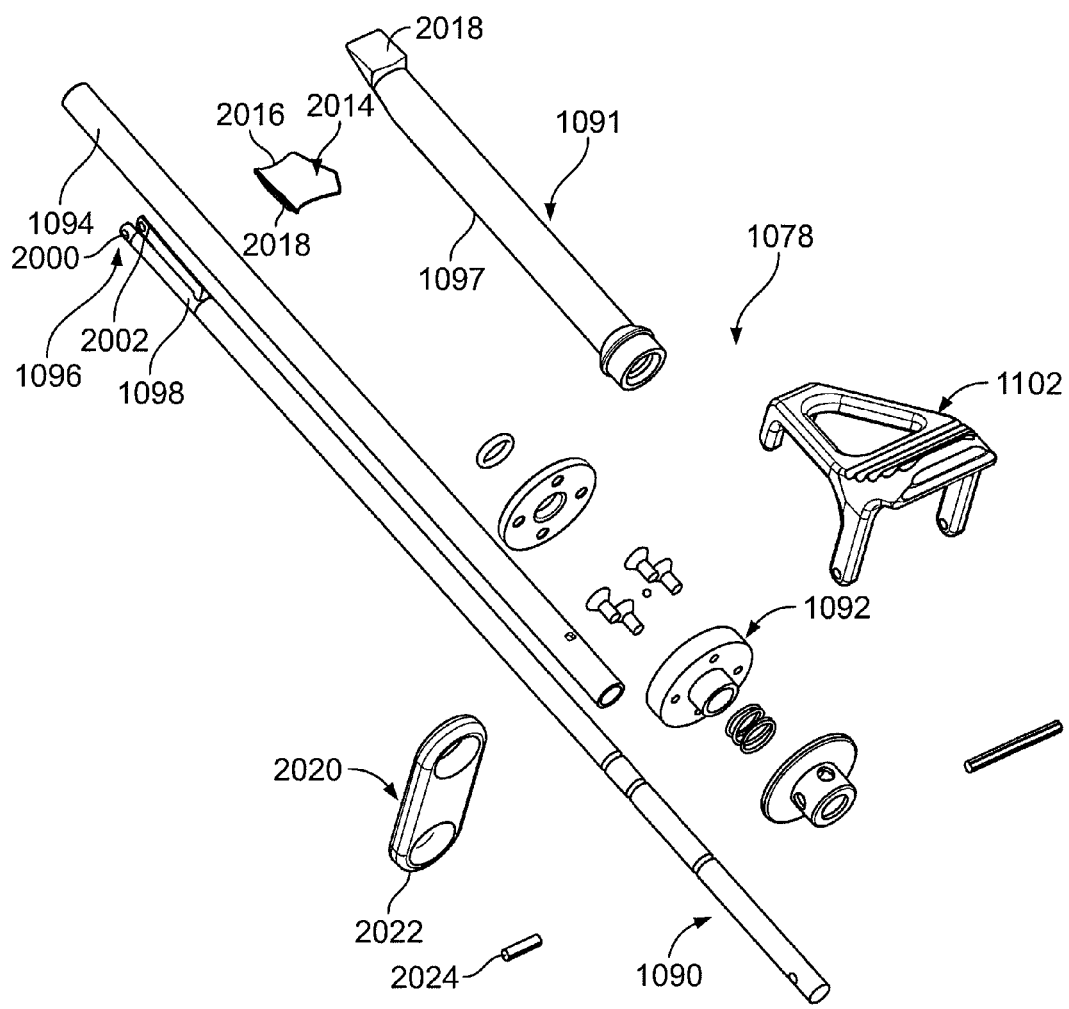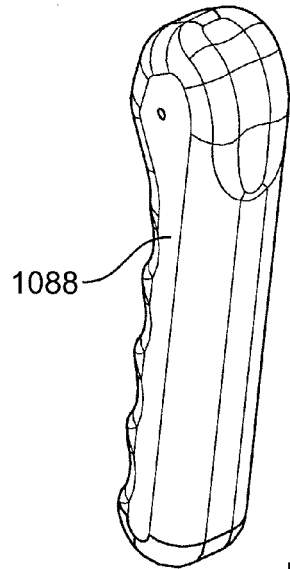
FIG. 48C

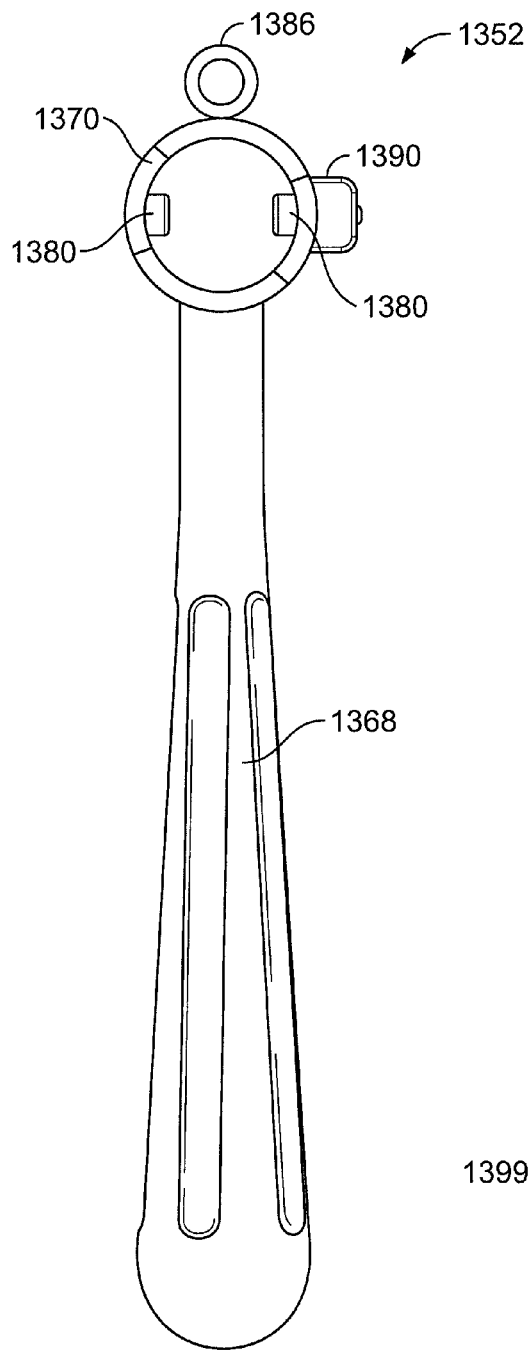
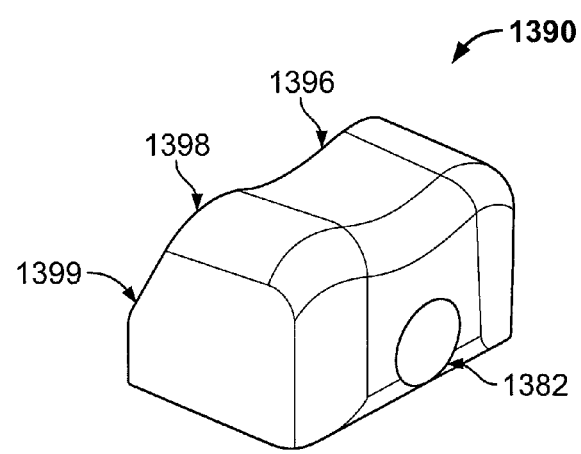
FIG. 51C
FIG. 51D

MINIMALLY INVASIVE SURGICAL SYSTEM

CROSS-REFERENCE TO RELATED APPLICATIONS

This application is a U.S. national phase application filed under 35 U.S.C. §371 of International Application PCT/US2007/076687, filed on Aug. 23, 2007, designating the United States, which claims priority to U.S. Provisional Application 60/839,895, filed on Aug. 23, 2006, which are hereby incorporated herein by reference in their entirety.

FIELD OF THE INVENTION

This invention relates generally to apparatus and methods for surgically implanting bone fixation devices, and more particularly, to surgical instruments and surgical methods that secure bone or bone segments relative to one another with minimal invasion into the surrounding body tissue.

BACKGROUND OF THE INVENTION

Implant devices secured to bone or bone segments are utilized to promote the healing and repair of various parts of the human body. In some cases, the implant devices are secured to the bone or bone segments such that the bones themselves heal, fuse, or stabilize relative to one another. In other cases, implant or fixation devices are used to secure bones or bone fragments so that the surrounding soft tissue may heal without disruption by relative movement of the bones.

During the surgical procedure to implant the fixation devices, a plurality of bone screws or other fixations elements are secured to a plurality of respective bones. Then, each of the bone screws is secured relative to the others with an additional apparatus, such as a connecting member or rod.

For example, spinal rods that immobilize vertebral bones of the spinal column are typically anchored to the vertebrae via bone screws that extend through the pedicle into the vertebral bodies or by hooks that engage about the vertebrae. The spinal rods are connected to the screws or anchor members by coupling members, which may be yoke-shaped. Such coupling members may be integral with the anchor member head or separate components from the anchor member.

While an incision into a patient's skin is often required during surgical implant procedures to gain access to a surgical site, such incisions can cause damage, injury, and trauma to the patient's body. Increased trauma to the body can undesirably lead to prolonged recovery time, infections and longer hospital stays following surgery. To avoid causing unnecessary trauma, it is preferable to make the incisions as small as possible, while also providing sufficient access to the surgical site. One way to accomplish these dual objectives is to make the incisions as small and as few as possible.

One prior approach to implanting a bony structure stabilization device uses an installation instrument with a pivoting brace inserter. To implant the connecting element, extensions are attached to the anchors and the installation instrument with the pivoting brace inserter being ridgidly attached to the extensions. The pivoting brace inserter employs a fixed geometric relationship to guide the connecting element into position. The installation instrument mounts to the bone anchors extension and holds the connecting element such that when the instrument's pivoting arm is pivoted, the connecting element follows a direct predetermined path into position about the anchor. As the connecting element is swung into position, the element enters the body through the skin at a remote location removed from the surgical incisions made to attach the bone anchors.

This approach can be problematic because another incision or opening is made through the skin, in addition to the openings required to insert the two screws. This additional opening allows for insertion of the brace or rod. Further, because of the fixed path, such a system is unable to direct the connecting element along a path of least resistance through the soft tissues and thereby causes tissue trauma that could otherwise be avoided by the surgeon variably moving the connecting element around and between these tissues. In addition, if the patient's vertebrae are misaligned the surgeon can encounter difficulty when inserting the brace along predetermined path because the predetermined path may not account for the various vertebrae locations.

Another approach to the minimally invasive system utilizes the same pathway that is used to insert the spinal anchors to also insert the connecting element. The connecting element is then manipulated such that it shifts to a perpendicular orientation to the insertion pathway in order to connect the bone anchors. Position of the connecting element can be assisted by a manipulation tool such that it is relatively guided relying on the predetermined path created by the various instrumentation tools.

Accordingly, there is a need for a minimally invasive surgical system that limits the number and size of the incisions, minimizes trauma to the soft tissues, and also provides physicians with control to efficiently and effectively implant necessary devices.

SUMMARY OF THE INVENTION

In accordance with one aspect of the present invention, a minimally invasive surgical (MIS) system and method are disclosed that secure bone or bone fragments together, such as vertebrae. To this end, the apparatus and methods utilize a plurality of pedicle screw assemblies and a connecting member. The bone anchors are fixed to the bone and the connecting member or rod is secured to the bone anchors by a yoke, such that the bones are substantially fixed relative to one another. To implant the anchors and connecting member, the system utilizes a number of tools or instruments that provide the surgeon with accurate and precise implant insertion, while limiting the number and the size of the incisions required. While the MIS system can be used to secure various bones and bone fragments relative to one another, a pedicle screw assembly with a spinal rod is described herein as an example.

In one form, the MIS procedure is performed in stages. First, the surgical site is prepared. After preparation, the pedicle screw assemblies are attached to the bone. Subsequent to insertion of the screws, a rod or connecting member is positioned within the yoke portion of the pedicle screw assembly. The caps are then placed in either a pre-lock or final-lock position within the yokes. When only one of the caps is in the final-lock configuration, the bone screws may be compressed together or distracted along the rod or connecting member, thereby setting the final spacing of the bones or bone segments. Finally, the remaining caps are moved to the final lock configuration to fix the screws to the rod or connecting member to maintain the bones in a desire position relative to one another.

A surgical procedure typically begins by preparing the surgical site. Preparation may require a number of steps, including, but not limited to creating an incision, stretching the tissue surrounding the incision, and smoothing or otherwise preparing the surface of the bone. Next, the screws or bone anchors, along with the yoke, are inserted into the site and driven into the bone. After the bone anchors have been driven into the bone, the rod or connecting member is seated within the yoke of each bone anchor and spans between each bone anchor. A cap is seated within the yoke to secure the connecting member within the yoke. After the cap is inserted into the yoke, the cap is advanced to the pre-lock position. With one cap in the pre-lock position, the spacing between the bone anchors can be adjusted to ensure proper spacing of the vertebra by permitting the bone anchors to translate along the connecting member. After proper spacing is achieved, the caps are moved to a final locking position to fix the bone anchors to the connecting member. After final locking, the various tools used to complete the procedure can be removed from the surgical site and the incisions can be closed.

The preferred MIS implant includes at least two pedicle anchors or screws, yokes, caps, and a connecting member, although three or more screw assemblies can also be used. Ensuring proper anchor placement is generally necessary for a successful procedure. Therefore, a number of tools can be utilized to correctly position the implant. In a preferred form, the system may include a dilation tool, docking ports, yoke manipulators, restraints that engage the yoke manipulators, a rod inserter, and optionally a guide bar. Some or all of these tools may be used during a procedure, depending upon the needs of the patient and the preferences of the surgeon.

To begin the preparation step of the procedure, an opening or incision, such as a stab wound, is made at the surgical site. This may be done with a scalpel or possibly a self-cutting, self-tapping guide wire. The opening is then stretched or dilated to accommodate the tools needed to implant the device. Such dilation may be accomplished by a number of tools, such as series dilators, a multi-stage telescoping tissue dilator, or obturators. After the surrounding tissue is sufficiently stretched, a docking port is positioned in the opening and functions as the access window through which the rest of the procedure is conducted. After the docking port is secured in the opening, such as by using an articulating arm, such as an iron intern an example of which is disclosed in U.S. Pat. No. 6,308,423, the vertebrae can be prepared by using an awl or facing tool such that the bone anchors can be readily attached to the vertebrae.

After the surgical site has been prepared, the bone anchors are driven into the vertebrae. This stage of the procedure begins by attaching the bone anchors to the yoke manipulators. The bone anchors typically have a yoke attached or include a yoke portion integral with the anchor. Each yoke manipulator is positioned about a yoke before being inserted. Following attachment of the yoke to the yoke manipulator, the bone anchor, yoke, and yoke manipulator can together be advanced through the docking port to the surgical site where the anchor will be seated. A screw driver, separate from the yoke manipulator, can be used to advance the bone anchors into the bone. The screw driver can be mated with the head of the bone anchor before or after the yoke manipulator, anchor, and yoke are positioned at the surgical site through the docking port. After the anchor has been seated in the bone, the screw driver is removed.

After each of the bone anchors has been driven into to the vertebrae, the rod or connecting member is positioned within the yokes. To begin this stage of the procedure, a guide bar can be employed to align the openings in the yoke manipulators. The guide bar may be attached to the upper ends of the yoke manipulators and may permit selective locking of each relative to the guide bar. After the manipulator openings are aligned, the rod inserter, having the connecting member attached to one end, can be advanced through one of the yoke manipulators. The rod inserter is maneuvered to position the connecting member in the yokes, beginning with the yoke opposite the incision into which the rod inserter is located. Once the connecting member is positioned in the opposite yoke, the rod inserter is used to manipulate the connecting member into the yoke associated with the incision in which the rod manipulator is located. The connecting member can move relative to the rod inserter in different arrangements to facilitate insertion of the connecting member into the yokes. For example, the rod inserter can be configured to securely hold the connecting member such that there is no relative movement between the inserter and the connecting member. In another configuration, the connecting member is allowed to rotate relative to the rod inserter. In a preferred embodiment, the rotation only occurs in one limited direction. In another configuration, the connecting member is released from the inserter. Slots may be provided in the yoke manipulators to facilitate insertion of the rod into the yokes. Before the connecting member is completely released, the inserter is maneuvered such that the connecting member is fed into the other manipulator and into the yoke. After the connecting member is positioned in the yokes and one cap is in the pre-lock position so as to prevent rotation, the inserter is removed from the incision.

Subsequent to the positioning of the connecting member into the yokes, a cap is inserted into each of the yokes to secure the member therewith. The cap may be inserted in two steps: pre-lock and final-lock. In the pre-lock stage, the cap is rotated about its rotary axis so that a portion of the cap is advanced axially to a predetermined position or depth on the yoke such that there is adequate spacing between the cap and the head of the bone anchor or insert to allow the connecting member to be adjusted along the axis thereof in the yokes. The pre-lock configuration allows for the adjustment of the spacing of the bone anchors and vertebrae. It is often desirable to fully lock one of the caps in a system with two or more bone anchors and pre-lock the other cap or caps to allow the vertebral spacing to be adjusted. A cap inserter or rod persuader may be employed to pre-lock the caps. The cap inserter is typically used for the first cap that is seated in its respective yoke. The rod persuader, which can provide a mechanical advantage for seating the rod in the yoke, is typically used for the subsequent cap insertion after the first cap is seated. After the caps are pre-locked and the desired spacing of the vertebrae is accomplished, a final locking instrument is used to tighten the caps into the final-lock position.

Depending on the patient's anatomy, the device implanted, or the preferences of the surgeon, the procedure may be customized by employing various instruments alternative to those previously discussed or by using a different combination of tools. Thus, a number of tools are disclosed below having various configurations that may be suited to particular situations. The various tools can provide surgeons with flexibility to accommodate different patients and may also allow the surgeon to employ tools more suited to the surgeon's preferences.

One such alternative tool is an alternative rod inserter, which functions similar to the previously discussed rod inserter. The alternative rod inserter further includes structure in the form of a latch to limit movement of the members of the shaft assembly to thereby prevent accidental release of the connecting member from the alternative rod inserter. The alternative rod inserter also includes structure configured to engage the yoke manipulators during portions of the insertion procedure to verify correct positioning of the connecting member despite the lack of visual indication.

Another alternative tool is the convincing tool that provides a surgeon with another option for customization. The convincing tool is positioned around the yoke manipulators in order to seat or position the connecting member within the yokes of the pedicle screw assemblies. The convincing tool may be employed to position the rod in a procedure separate from the cap insertion procedure. A counter torque tube may also provide the surgeon with structure to move the connecting member down relative to the yoke of the pedicle screw in order to thereby seat the connecting member.

In addition to the MIS system, a number of the instruments described herein may also be used for a minimally open procedure (mini-open). During a MIS implantation, the implant is typically, though not necessarily, inserted through two or more expanded stab wounds. By comparison, the mini-open procedure can employ a slit opening that spans the distance between the vertebrae where the bone anchors will be seated. A retractor can be used with a mini-open procedure to expand the slit to provide the surgeon sufficient clearance to perform the procedure and, therefore, the instruments used for such a procedure are preferably sized and designed to fit easily within the opening created by the retractor. While the mini-open procedure can be more invasive than a typical MIS procedure, the mini-open procedure may be preferable depending on the patient's anatomy or the surgeon's preferences.

In one aspect of the methods disclosed herein for securing a spinal rod to a vertebral bone, a relatively small incision can be formed at a surgical site adjacent a first vertebral bone. A guideway can be confined through the small incision through which a tool or tools can be used to manipulate a pedicle screw assembly and spinal rod. During such manipulation, the tools can obstruct viewing of the pedicle screw assembly and the spinal rod through the confined guideway. A driving tool extending in the confined guideway can be used to turn a locking device of the pedicle screw assembly secured to the vertebral bone. During such turning, tactile feedback can be generated upon turning of the locking device to a predetermined rotary position in order to indicate that the spinal rod is clamped so that viewing of the locking device and spinal rod through the obstructed guideway to determine the clamping of the spinal rod is unnecessary.

In a further aspect, the turning of the locking device in order to clamp the spinal rod may include stopping rotation of the locking device at the predetermined rotary position at which the tactile feedback is generated. The stopping of the rotation of the locking device may include abutting a lower rod engaging portion against a stop of a turned upper portion of the locking device. The turning of the locking device for clamping the spinal rod includes driving a lower rod engaging portion of the locking device into clamping engagement with the spinal rod.

In another aspect of the system disclosed herein for positioning a spinal rod relative to two or more pedicle screws, a rod insertion tool is provided that includes an inner shaft having an end potion adapted to pivotably engage a spinal rod about a pivot axis and an outer control sleeve surrounding at least a portion of the inner shaft and having an end portion shiftable between a blocking position covering the pivot axis to restrict pivoting of the spinal rod about the pivot axis and an unblocking position spaced from the pivot axis to permit pivoting of the spinal rod about the pivot axis. A spinal rod can be pivotably connected to an end portion of the inner shaft about the pivot axis. The outer control sleeve can be positioned in a blocking position over the pivot axis to prevent pivoting of the spinal rod about the pivot axis. A first portion of the spinal rod can be inserted into a yoke of a first pedicle screw. The outer control sleeve can be moved to the unblocking position away from the pivot axis to permit pivoting of the spinal rod about the pivot axis and a second portion of the spinal rod can be inserted into a yoke of a second pedicle screw by pivoting the spinal rod about the pivot axis. Then the spinal rod can be disconnected from the end portion of the inner shaft.

The rod insertion tool may include a shaft assembly having a longitudinal axis, an inner elongate rod holding member of the shaft assembly extending along the axis of the shaft assembly, an outer shaft member of the shaft assembly extending along the axis of the shaft assembly, and a pivot connection of the rod holding member for pivotally connecting the spinal rod thereto. The outer shaft member of the shaft assembly can be moveable relative to the inner elongate rod member to block the pivot connection to prevent pivoting of the spinal rod.

In another aspect of the system disclosed herein for inserting a cap having a drive recess, into a yoke of a pedicle screw assembly, the cap inserter including an outer shaft having a drive end for insertion into the bore of the cap. The drive end of the outer shaft can have a plurality of prongs. An inner shaft can be disposed within the outer shaft. A cam interface is located between the drive end of the outer shaft and the inner shaft. The inner shaft is shiftable into a biasing position biasing the prongs outwardly for frictionally engaging inner surfaces of the drive recess of the cap in order to securely hold the cap.

In another aspect of the system disclosed herein for inserting a cap having a drive recess into a yoke of a pedicle screw, the cap inserter has an outer cylindrical shaft having a drive end for insertion into the drive recess of the cap. The drive end has a plurality of moveable prongs with a bore between the moveable prongs. The prongs may have internal cam surfaces. The cap inserter further includes an inner cylindrical shaft disposed within the outer shaft and having external cam surfaces. The cam surfaces of the inner shaft are axially shiftable toward the cam surfaces of the outer cylindrical shaft to urge the prongs outwardly for frictionally engaging inner surfaces of the drive recess of the cap in order to securely hold the cap.

In another aspect of the method disclosed herein for gripping a cap having a drive recess insertable into a yoke of a pedicle screw, a split drive end can be inserted into the drive recess of the cap and shifted in a transverse direction into tight engagement with the drive recess of the cap.

In another aspect of the system disclosed herein for inserting a cap having a drive recess into a yoke of a pedicle screw, the cap inserter has a shaft assembly with an elongate drive member having a split drive end configured for engaging the drive recess of the cap. An actuator of the shaft assembly is operable to shift the split drive end of the elongate drive member into tight engagement with the drive recess of the cap for securing the cap to the elongate drive member.

In another aspect of the method disclosed herein for inserting a spinal rod into the yokes of at least two pedicle screw assemblies, a first yoke manipulator can be placed around a yoke of a first pedicle screw assembly. The first yoke manipulator has an axial entrance slot aligned with one of the side openings in the yoke of the first pedicle screw assembly and an axial exit slot aligned with the opposing side opening. A second yoke manipulator can be placed around a yoke of a second pedicle screw assembly. The second yoke manipulator may have an axial entrance slot aligned with one of the side opening in the yoke of the second pedicle screw assembly and an axial exit slot aligned with the opposing side opening. The slots may have a length longer than a depth of the side opening. A spinal rod inserter can be provided having a spinal rod connected thereto about a pivot axis. A distal end portion of the spinal rod can be passed through the entrance and exit slots of the first yoke manipulator to position the pivot axis between the entrance slots of the first and second yoke manipulators. The distal end portion of the spinal rod can then be passed through at least the entrance slot of the second yoke manipulator to a position in the side opening of the yoke of the second pedicle screw assembly. The proximate end portion of the spinal rod may then be positioned in the side opening of the yoke of the first pedicle screw assembly.

In another aspect of the method disclosed here in for positioning a spinal rod between a pair of pedicle screw assemblies, a first yoke manipulator can be positioned around one of the pair of pedicle screw assemblies and a second yoke manipulator can be positioned around the other of the pair of pedicle screw assemblies. Each of the first and second yoke manipulators may have a pair of opposing slots aligned with side opening in yokes of the pair of pedicle screw assemblies. A spinal rod can be provided that connects to an insertion tool about a pivot axis. The spinal rod can be passed through the first yoke manipulator to position the pivot axis between the first and second yoke manipulators. The spinal rod can be freely orientated in the side opening of the yoke of the pedicle screw assembly in the second yoke manipulator. The spinal rod can then be pivoted relative to the insertion tool about the pivot axis to shift the pivot axis from between the first and second yoke manipulators to an opposite side of the first yoke manipulator to position the spinal rod in the side opening of the pedicle screw assembly in the first yoke manipulator.

The minimally invasive surgical system may include a pedicle screw assembly having an anchor for engaging the vertebral bone, a yoke for receiving the spinal rod and a locking device for clamping the spinal rod in the yoke. An elongate tubular member is provided for extending through an incision to allow for tool access to the vertebral bone. A tool is adapted to fit through the tubular member and to turn the locking device until reaching a stop that keeps the tool from turning the locking device by more than a predetermined amount.

The minimally invasive surgical system may include a pedicle screw assembly having an anchor for engaging the vertebral bone, a yoke for receiving the spinal rod, and a non-threaded locking device for clamping the spinal rod in the yoke. An elongate tubular member may extend through an incision to allow for tool access to the pedicle screw assembly anchored to the vertebral bone. A tool is provided and configured to fit through the tubular member and to turn the non-threaded locking device for clamping of the spinal rod in the yoke.

In another aspect of the method disclosed herein for securing a spinal rod to a vertebral bone, a relatively small incision can be formed at a surgical site adjacent a first vertebral bone. A pedicle screw assembly and spinal rod can be manipulated with surgical tools via the small incision. The pedicle screw assembly can be secured to the first vertebral bone and a locking device of the pedicle screw assembly can be turned to a first predetermined rotary position in a yoke of the pedicle screw assembly. The turning of the locking device can be restricted beyond the first predetermined rotary position. The spinal rod received in the yoke can be adjusted in the yoke of the pedicle screw assembly with the locking device at the first predetermined rotary position. The locking device can then be turned beyond the first predetermined rotary position to clamp the spinal rod in the yoke once the spinal rod has been adjusted. A guideway is confined through the small incision through which tools manipulate the pedicle screw assembly and the spinal rod with viewing of the pedicle screw assembly and spinal rod during manipulation being obstructed by the confined guideway and tool or tools therein.

BRIEF DESCRIPTION OF THE DRAWINGS

FIG. 1D is a cross-sectional view of the spinal fixation device showing a recess formed in the screw head in which a low profile anvil insert is received for clamping of the spinal rod thereagainst;

FIG. 1E is a cross-sectional view similar to FIG. 1D showing the relative sizes of the various components of the spinal fixation device;

FIG. 1F is an elevational view similar to FIG. 1C with the coupling member removed to show the radial flanges on the cam lock member and a bottom cam surface thereof;

FIG. 1G is a cross-sectional view of the spinal fixation device. showing the recesses formed in the coupling member configured to receive the radial flanges on the cam lock member;

FIG. 3 is a perspective view of a docking port;

FIG. 4 is a front view of the docking port of FIG. 3;

FIG. 5 is a side elevation view of the docking port of FIG. 3;

FIG. 6 is a top view of the docking port of FIG. 3;

FIG. 16a is a top view of a portion of the guide bar of FIG. 16;

FIG. 48C is an exploded view of the rod inserter of FIG. 48A showing the components of the rod inserter;

FIG. 51C is a top plan view of the alternative counter torque tube of FIG. 51A;

FIG. 51D is a perspective view of a fulcrum portion of the counter torque tube of FIG. 51A;

The elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements may not be depicted in order to facilitate a less obstructed view of the various structures. It will further be appreciated that certain actions and/or steps may be described or depicted in a particular order of occurrence while those skilled in the art will understand that such steps can be performed in different orders and that certain steps may be omitted, depending upon patient need and/or surgeon preference.

DETAILED DESCRIPTION OF THE DRAWINGS

Figure 1A:
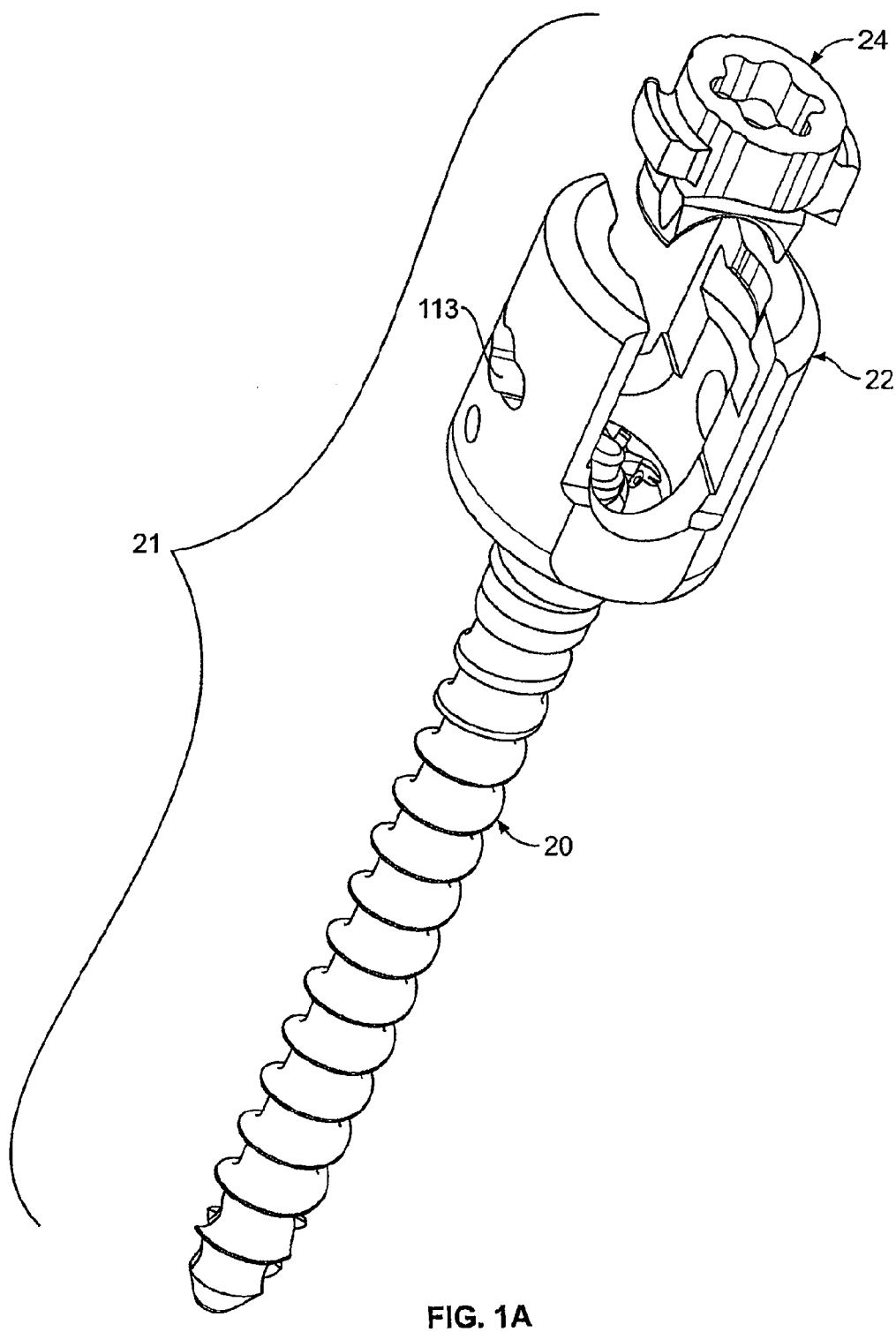
FIG. 1A is a perspective view of a bone anchor, a yoke, and a cap.
Figure 2:
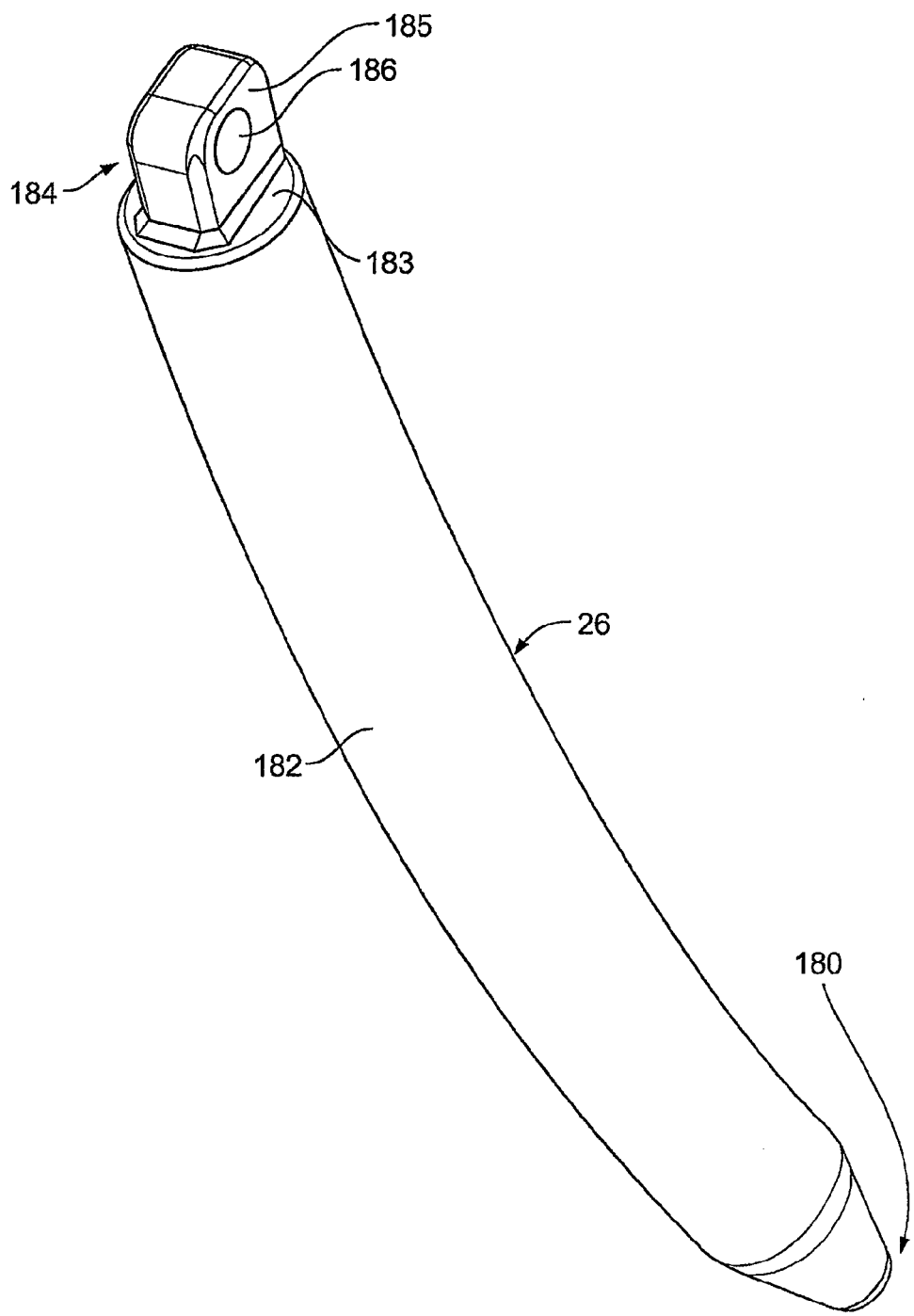
FIG. 2 is a perspective view of a connecting member.

The minimally invasive surgical ("MIS") system can be utilized to attach an implant or fixation device to bone or bone segments. The fixation device illustrated herein is attached to the spinal column, but such a fixation device could be attached to bones other than vertebrae. The fixation device stabilizes bone or bone segments relative to one another. In one form, the fixation device includes a bone anchor or screw 20, a yoke 22, and a closure cap 24, as illustrated in FIG. 1A. The cap 24 locks into the anchor yoke 22 such that an intermediate spinal rod or connecting member 26 is held in position. The connecting member 26 may be curved, as shown in FIG. 2, or it may be straight, depending upon the curvature of the patient's spine. The connecting member 26 is seated into the yoke 22 and secures the bone anchors 20 relative to one another when locked by the cap 24.

One embodiment of the fixation device includes two anchors 20, two yokes 22, two caps 24, and a connecting member 26. In another preferred embodiment, a fixation device may include three anchors 20, three yokes 22, three caps 24, and one connecting member 26. A similar fixation device is disclosed in co-pending applications PCT/US2004/003605 and U.S. patent application Ser. No. 10/973,659, both of which are hereby incorporated by reference in their entirety. Since the bone anchors 20, yokes 22, and closure caps 24 are implanted into the body, they are preferably made of biocompatible material.

An exemplary embodiment of a low profile spinal fixation system or device 10 is shown in FIGS. 1B-1H. This spinal fixation device 10 includes a pedicle screw assembling having a bone anchors or bone screw 12 and the coupling device generally designated 14. The coupling device 14 is operable to secure an elongate member such as the connecting member or spinal rod 16 in place relative to the bone screw 12. The coupling device 14 includes a compression or cam lock member or device 18 and a coupling member 19 that cooperate to secure the spinal rod 16 relative to the bone screw 12 anchored in a vertebral bone with the rod 16 generally extending axially along the spinal column. The coupling device 14 and specifically, the cam lock member 18 and coupling member 19, are provided with a compact configuration. In particular, the cam lock member 18 and coupling member 19 may be provided with a very low profile in a direction indicated by the axis line 2 extending transverse and specifically orthogonally to the axis 3 of the spinal rod 16 fixed relative to the bone screw 12 by the coupling device 14, as best seen in FIG. 1E.

The low profile of the coupling device 14 is obtained by having the cam lock member 18 able to lock the spinal rod 16 without needing to advance the cam lock member 18 along the coupling member 19. In this regard, the coupling member 19 can be provided with a body 4 having side openings 4a and 4b through which the spinal rod 16 passes with the body 4 free of any threading or cam surfaces that cooperate with the cam lock member 18 for locking of the spinal rod 16 relative to the bone screw 12. Instead, the cam lock member 18 is fixed against translation relative to the coupling member 19, and preferably cooperates with the outer curved surface 5 of the rod 16 itself to secure it in position relative to the screw 12 in the device 10.

For this purpose, the cam lock member 19 has a generally annularly configured body 9 having a very short axial extent along turning axis 2 thereof via annual side surface 9a extending between its tip and bottom surfaces 9b and 9c. The top surface 9b is provided with driving surface portions 11 which cooperate to form a predetermined configuration for the receipt of a similarly configured drive tool for turning the cap member 18 between unlocked and locked positions thereof. The bottom surface 9c is programmed or contoured to provide a camming action on the curved surface 5 of the rod 16 when the cal lock member 18 is turned. In another form, an intermediate clamping member in the form of a saddle member can be provided between the lock member 18 and the spinal rod 16. The saddle member may have an upper cam surface configured for cooperation with the lock member cam surface when the lock member 18 is turned to its locked position so that the saddle member shifts downwardly along axis 2 for clamping against the rod 16 without camming thereagainst.

Similar to the cam lock member 18, the coupling member 19 also has a relatively small axial extent between the top and bottom surfaces 19a and 19b thereof. The body of the coupling member generally has a U-shaped or yoke configuration including opposing upstanding walls 19c, 19d spaced from each other by the rod openings 4a and 4b which can have an elongate configuration and be open to the top 19a of the coupling member body 4. Since the cam lock member 18 need not be advanced down along the walls in the direction 2, the size in this direction can be minimized.

The annular body of the cam lock member 18 is sized to fit in the internal space of the coupling member between arcuate upstanding walls 19c, 19d that cooperate with the cam lock 18 for shifting it to a locked position. The walls 19d, 19d are free of threading or cam surfaces that cooperate with the cam lock member 18 for shifting it to a locked position. More particularly, the inner surface 13 of the coupling member 19 including arcuate surface portions 13a and 13b on the respective coupling walls 19c and 19d are sized to closely receive the outer surface 9a of the cam lock member annular body 9. These surface portions 13a and 13b are each free of threading or cam surface and thus only serve as guide surfaces or the like, the size of the coupling device 14 can be kept to a minimum in the widthwise direction along the axis 3 of the spinal rod 16 as well.

Referring now to FIGS. 1D and 1E, the illustrated spinal fixation device 10 has a polyaxial bone screw 12 whose orientation can be changed such that its longitudinal axis 12a extends transverse to the axis 2 of the coupling device 14 or is substantially aligned therewith. To this end, the coupling device 19 is provided with a bottom throughbore 50 that extends through the bottom wall 52 of the coupling member 19. The bottom wall 52 includes an inner surface portion 54 that tapers or curves inwardly from the surface portions 13a, 13b toward the center axis 2. The diameter across the inner surface portion 54 at it lowermost end 56 is sized to be smaller than an enlarged head 58 of the bone anchor screw 12. In addition, the diameter at 56 is sufficiently large to allow the threaded shank 60 depending from the screw head 58 to be advanced therethrough. In this manner, the inner surface portion 54 serves as a seating surface from the screw head 58. As an alternative, the diameter 56 is threaded with a thread oversized relative to the shank, thereby allowing the screw shank 60 to be loosely threaded through. In this instance, the diameter 56 is sized to hold the shank 60 from passing easily through so that the screw 12 and coupling member 19 may be handled by a surgeon as a single component during the operation. In addition, the oversized threads allow the screw to be polyaxial in its orientation. As a further alternative, the screw 12 may be passed through the diameter 56, and a c-ring or radial spring may be attached to the screw 12 immediately adjacent to the coupling member 19, thereby holding the two together and allowing the surgeon to utilized them as a single component during the operation.

The throughbore 50 extends centrally through the inner surface portion 54 and includes and enlarged lower portion 62 formed by tapered or curved surface portion 51 on the bottom wall 52 of the coupling member 19. The tapered surface 51 extends from the smallest diameter of the bore 50 at 56 tapering outwardly relative to the center axis 2 of the coupling member 19 to the bottom surface 19b thereof. The enlarged bore portion 62 allows the screw 12 to swivel or pivot to a variety of different orientations thereof relative to the coupling device 14. For example, in the illustrated form, the enlarged bore portion 62 allows the screw shank to pivot by 20 degrees on either side of the coupling device axis 2. As the screw 12 is pivoted, the outer arcuate surface 53 of the screw head 58 rides or shifts on the tapered seat surface 54 in the coupling member 19. Once the orientation of the coupling device 14 relative to the bone screw 12 fastened into a vertebral bone is determined with the spinal rod 16 extending through the coupling member 19 and up along the spinal column, the cam lock member 18 is then turned to its locked position. In the locked position the cam lock member 18 anchors the rod 16 to the spinal column so it is fixed relative to the bone screw 12 fastened into a vertebral bone with the bone screw head 58 clamped against the seat 54 thereof in the coupling member 19 thereby fixing coupling device 14 against shifting relative to the bone screw 12. The outer screw head surface 53 can be configured with concentric friction enhancing ridges or helical threads 67 to enhance the locking action between the screw head 58 and seat 54.

Continuing reference to FIGS. 1D and 1E, it can be seen that in the illustrated polyaxial spinal fixation device 10, the spinal rod 16 is pushed downwardly for being clamped against a small anvil insert 55. It should be noted that the previously described low profile coupling device 14 could be employed in spinal fixation systems that are not polyaxial and/or which do not employ an insert as described hereinafter. Similarly, the present insert 55 could be advantageously employed in systems that employ threads or cams in the coupling members thereof.

The insert 55 has an upper anvil surface 55a that engages against the underside of the spinal rod surface 5 to maintain enhanced contact therewith over the curved surfaces of bone screw heads. The insert 55 has an upper surface 55a that may be substantially flat, may have radially oriented concave paths or valleys so that the insert 55 rotates to the closest path to meet with the spinal rod surface 5 or, may have a cup or peripheral ridge that deforms when compressed by the spinal rod 16 to form a path without deforming the spinal rod. Accordingly, the insert 55 provides at least a line of contact with the curved rod surface 5. In other embodiments, it is anticipated that the bone anchor 12 and the insert 55 will have a unitary configuration.

The cam lock member 18 does not translate along the coupling member 19 when it is turned to its locked position. In order to keep the cam member 19 fixed against movement in the direction along axis 2, it is provided with radial flanges 90 and 92 extending radially outwardly from the annular body 9 at diametrically opposite positions thereon. The flanges 90 and 92 are received in correspondingly configured recesses 94 and 96 formed in the coupling member walls 19c and 19d, as can be seen in FIG. 1G. The recesses 94 and 96 have an arcuate configuration extending about axis 2 as do the radial flanges 90 and 92 for fitting therein and allowing turning of the cam lock member 19 between unlocked and locked positions thereof. The flanges 90 and 92 are received in the recesses 94 and 96 when the cam lock member 18 is turned toward its locked position. With the cam surface 9c camming on the rod surface 5, the flanges 90 and 92 in the closely conforming recesses 94 and 96 prevent the cam lock member 18 from shifting upwardly away from the spinal rod 16 and instead forces the spinal rod 16 down into clamping engagement with the insert 55 which, in turn, causes the screw head 58 and specifically outer head surface 53 to be clamped against the seat surface 54 in the coupling member 19 thus fixing the coupling device 14 relative to the bone screw 12 and anchoring the spinal rod 16 to the spinal column.

Figure 11:
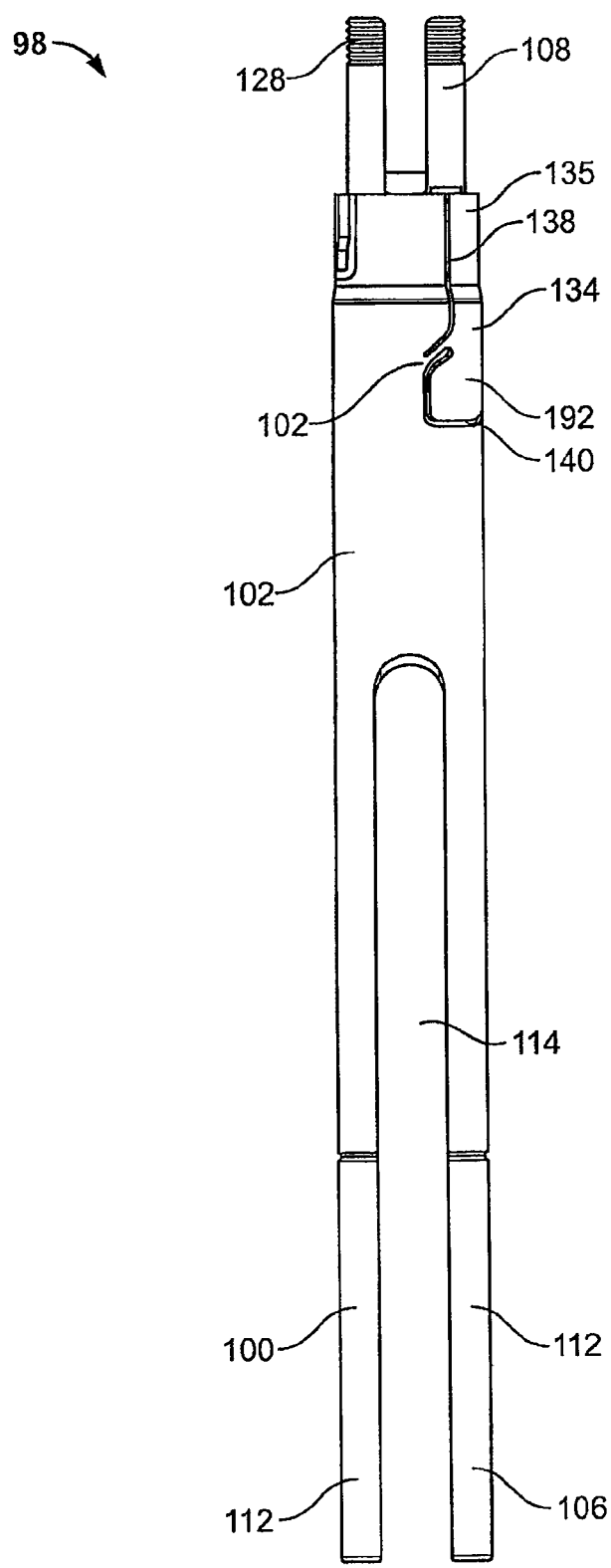
FIG. 11 is a front view of the yoke manipulator of FIG. 10.

As previously mentioned, the cam lock member 18 has a contoured bottom cam surface 9c that cams on the curved cam surface 5 of the spinal rod 16. The cam surface 9c is best seen in FIG. 11. In the illustrated and preferred form, the cam surface 9c is contoured to provide three distinct regions defined in relation to their action of the spinal rod 16. A first concave region 61 extends across the bottom 9c of the cam lock member body 9 and can be aligned with the radial flanges 90 and 92. Accordingly, the radial flanges 90 and 92 will be disposed slightly above the bottom 9c of the cam lock member body 9 to accommodate the spinal rod curved surface 5 extending therebelow with the cam lock member 19 in the unlocked position thereof. In this position, the flanges 90 and 92 are not received or fully received in the recesses 94 and 96 thereof.

Diametrically opposite sections 61a, 61b of the concave surface region 61 are provided so that rotation of the cam lock member 18 in the unlocked position does not cause a camming action to occur with only a slight initial turning action thereof. With the spinal rod surface 5 aligned with the surface portions 61a and 61b, the spinal rod 16 is still loosely received under the cam lock member 18 and is not cammed thereby. The surgeon may use this position as a pre-lock configuration. Beneficially, the spinal rod 16 is captured under the cam lock member 18 so as to provide the surgeon with greater freedom of manipulation before finally locking the cam lock member 18. With continued turning of the cam lock member 18, the camming action begins at ramp regions 35 and 37 that are diametrically opposite to each other on the cap bottom surface 9c and project downwardly from the adjacent surface sections 61a, 61b along direction 2. The ramp regions 35, 37 are configured so that the rod 16 is progressively pushed downward in the direction 2 as the cam lock member 18 is turned about the turning axis 2 toward the locked position. Accordingly, in the unlocked position these ramp surface regions 35 and 37 on the bottom cam surface 9 extend down along either side of the spinal rod 16 so as to advantageously take up the space on either side thereof thus serving to keep the space occupied by the cam lock member 18 in the coupling member 19 to a minimum for providing the overall coupling device 14 with a low profile.

Figure 1B:
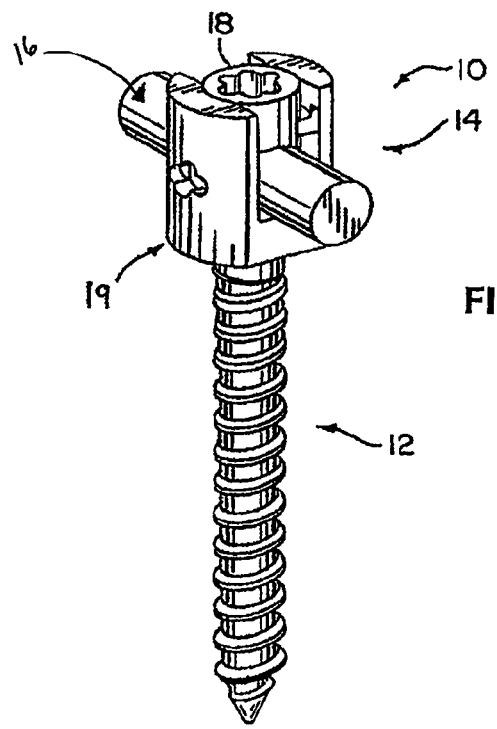
FIG. 1B is a perspective view of a spinal fixation device showing a bone screw and coupling device including a coupling member and a cam lock member for securing a spinal rod relative to the bone screw.
Figure 1C:
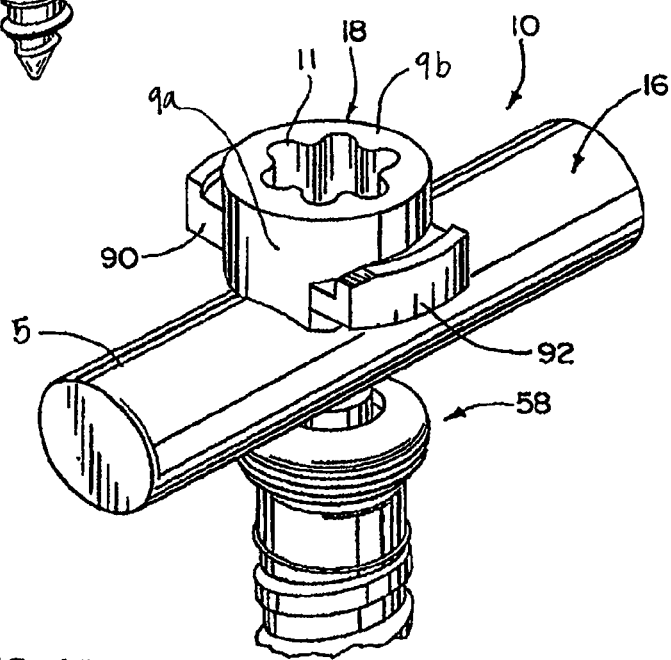
FIG. 1C is an enlarged perspective view of the spinal fixation device of FIG. 1B with the coupling member removed to better illustrate the cam lock member and to show the configuration of the head of the bone screw.
Figure 1H:
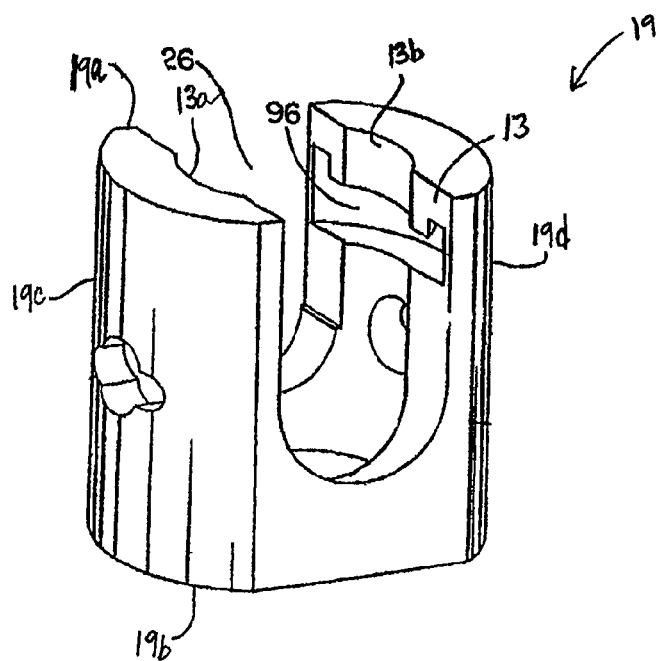
FIG. 1H is an enlarged perspective view of the yoke-shaped coupling member illustrated in FIG. 1B.
Figure 1I:
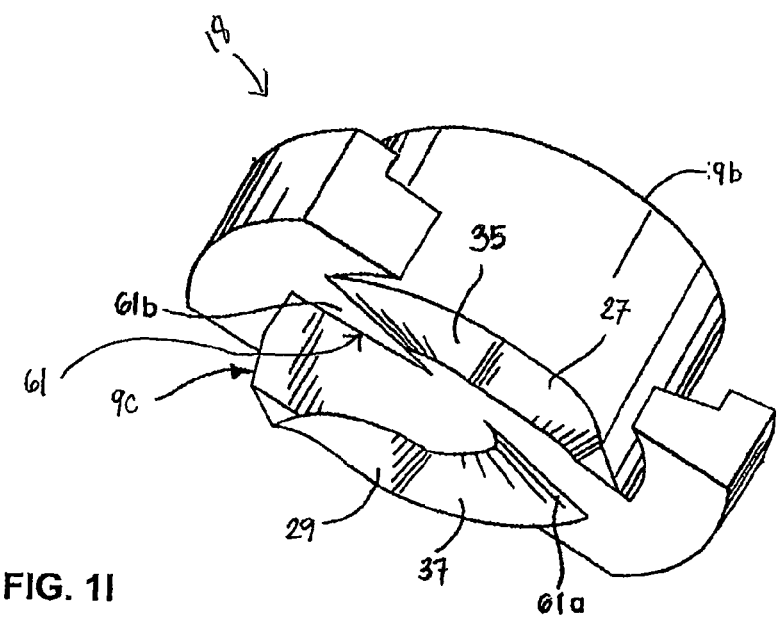
FIG. 1I is an enlarged perspective view of the cam lock member illustrated in FIG. 1B.

Continued turning of the cam lock member 18 toward the locked position causes the rod surface 5 to be engaged against diametrically opposite generally flat surface regions 27 and 29 adjacent to the ramp surface regions 35 and 37 respectively. In an alternative form, the surface regions 27 and 29 may be a valley shape providing a depression such that the rod 16 is received into the depression. The surface regions 27 and 29 are not inclined relative to the axis 2 like the preceding ramp surfaces 35 and 37 and are the lowest point of engagement of the cam surface 9c with the rod surface 5. With the cam lock member 18 turned so that the rod surface 5 is only engaged by the surface regions 27 and 29, the cam lock member 18 is in its fully locked position with the cam lock member flanges 90 and 92 fully received in the corresponding yoke wall recesses 94 and 96, as shown in FIGS. 1B and 1G. Continued turning of the cam lock member 18 in the same direction after the fully locked position has been reached is prevent by abutment surface regions adjacent to the surface regions 27 and 29 respectively. These abutment surfaces extend further downwardly in direction 2 from the surface regions 27 and 29.

Accordingly, in the exemplary embodiment illustrated, programmed cam surface 9b provides several stages for the camming and locking action on the spinal rod 16. As shown, the cam member 18 can be rotated by approximately 20 degrees from the unlocked position before the rod surface 5 reaches the ramp surfaces 35 and 37. At this point, the rod 16 is cammed downwardly and the cam lock member can be turned for another approximately 60 degrees before the rod surface 5 reaches the flat locking surfaces 27 and 29. The cam lock member 18 can then be turned by another approximately 20 degrees before the rod surface 5 abuts against the stop surfaces and then the cam lock member 18 is in its fully locked position. Thus, in one embodiment, there is approximately 100 degrees of rotation of the cam lock member 18 that is required from the fully unlocked position to the fully locked position with 20 degrees of play provided before the camming action begins and the camming of the rod 16 occurring over the final 80 degrees of rotation to the fully locked position.

Figure 1J:
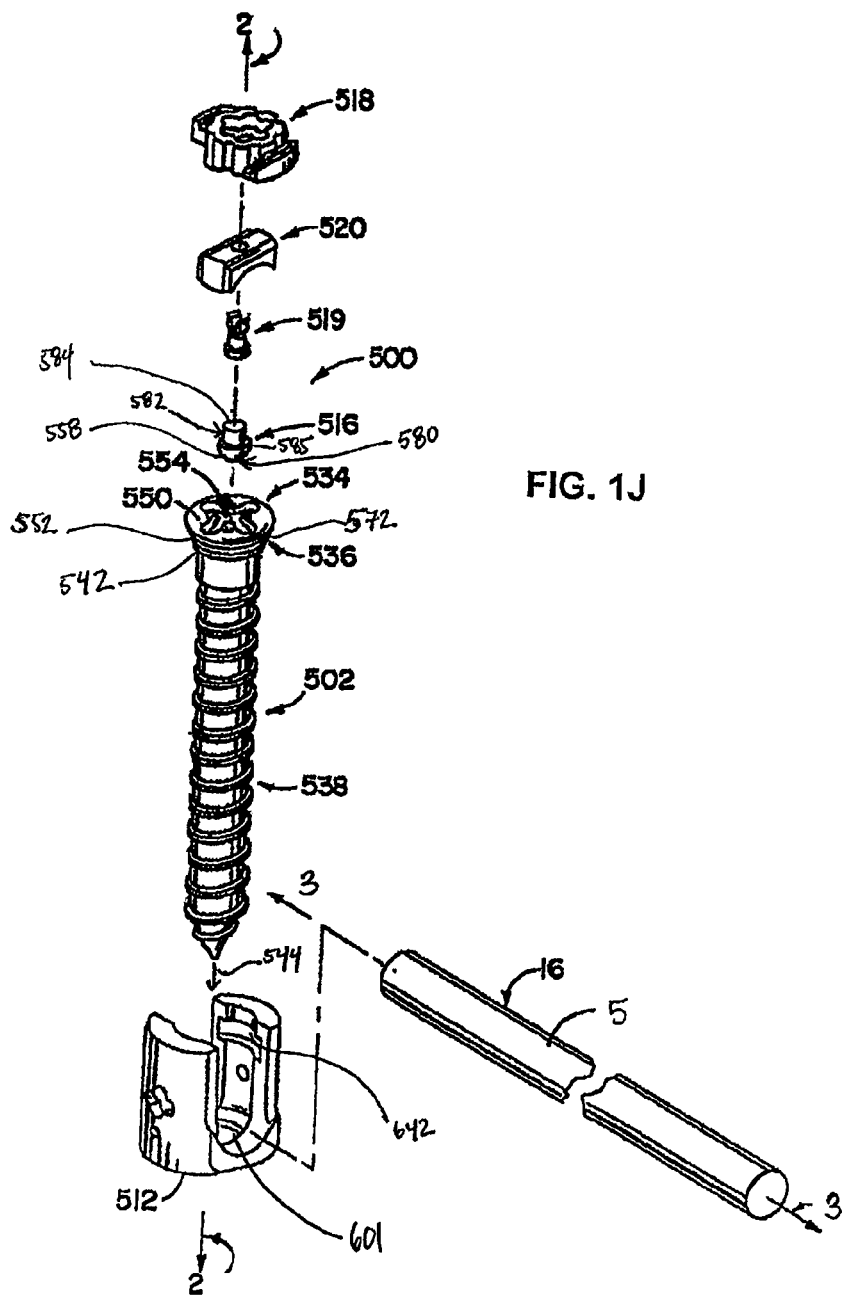
FIG. 1J is an exploded perspective view of another form of the spinal fixation system showing a bone screw and a coupling device including a coupling member, a cam lock member, a spring clip connector member, a clamping member, and an insert for securing a spinal rod relative to the bone screw.
Figure 1K:
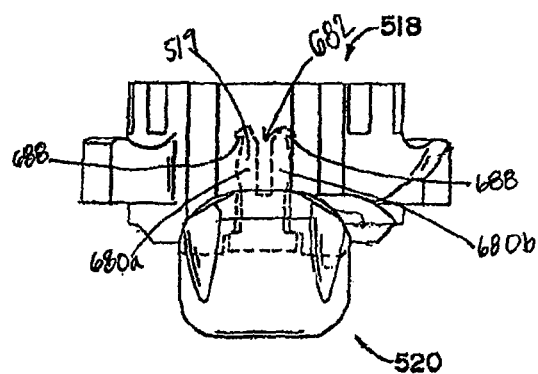
FIG. 1K is side elevational view of the cam lock member, and the clamping member in an unlocked position relative to the spinal rod.
Figure 1L:
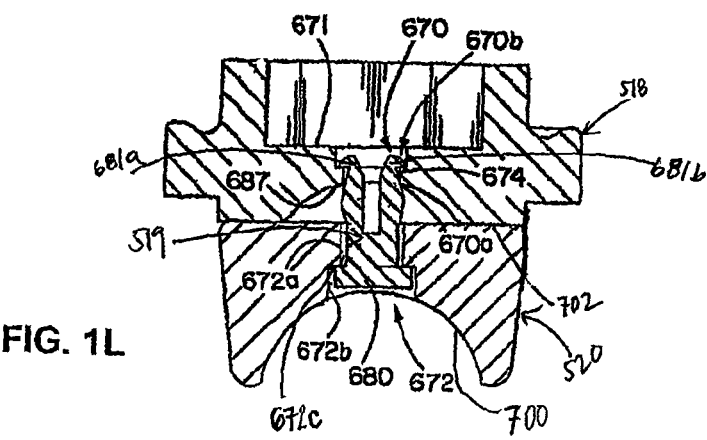
FIG. 1L is a cross sectional view of the cam lock member and the clamping member showing the clamping member shifted down along with the spring clip connecting with the cap member axially fixed and rotated to its locked position.

FIGS. 1J-1L illustrate another exemplary embodiment of a low profile spinal fixation system or device 500 for securing a spinal rod 16. The device 500 includes a bone anchor member such as a screw 502 and a coupling device for securing the spinal rod 16 relative to the bone screw 502. The coupling device includes a coupling member in the form of a unitary yoke 512, an insert in the form of anvil 516, a cam lock member in the form of a cap 518, a connector member in the form of a spring clip 519, and a clamping member in the form of a saddle 520. The fixation device 500 is similar to the embodiment of FIGS. 1A-1I in that the cap 518 and yoke 512 are provided with a very low profile in the direction indicated by yoke axis line 2 extending transverse and specifically orthogonally to the axis 3 of the spinal rod 16 fixed relative to the bone screw 502 by the coupling device.

The screw 502 is directed through the yoke 512 and attaches the yoke 512 to a bone or bone fragment. The screw 502 has a head 536 with a recess 554, and the recess 554 receives the anvil 516. The spinal rod 16 is received within an internal space or channel 601 in the yoke 512 and is seated on top of anvil 516. The screw 502 is preferably a polyaxial screw, and the anvil 516 is permitted to move within the head 536 of the screw 502. Accordingly, prior to the device 500 being secured, the screw 502 may move relative to the yoke 512 so that the yoke 512 and screw 502 may be selectively positioned to assume different orientations relative to each other so that their respective axes 2 and 544 are not necessarily aligned with each other, and the anvil 516 may move and pivot or rotate relative to the screw 502 so that the anvil 516 may be properly positioned by orienting itself with the outer surface 5 of the rod 16 similar to the previously described anvil 55.

The rod 16 is secured or locked within the yoke 512 with the cap 518 and saddle 520. As will be discussed below, rotation of the cap 518 has the dual function of securing the cap 518 within recesses 642 in the yoke 512 and of forcing the saddle 520 against the rod 16 to lock the rod 16 between the saddle 520 and the anvil 516. The saddle 520 and cap 518 are secured together in assembly by a distinct connector in the form of a dual-pronged, spring clip 519.

The bone screw 502 is preferably polyaxial, and the head 536 is diametrically larger than the shank 538 at the neck 542. The polyaxial features of the screw 502 allow the screw 502 to be secured to a bone in a desired orientation for proper fixation to the bone while allowing the yoke 512 to be oriented relative to the screw 502 in an orientation desired for seating a rod 16 therein.

The head 536 of the screw has an arcuate or slightly ramped top surface 550 which meets a peripheral outer surface 552 of the screw head 536. The peripheral outer surface 552 of the screw head 536 has a generally arcuate or spherical profile. The profile is interrupted with a series of concentric ridges or circular grooves cut therein. As discussed above, the screw 502 is polyaxial so that its orientation relative to the yoke 512 can be precisely positioned. When the coupling device is secured to the screw 502, the grooves grip of cut into the interior of the yoke 512 to immobilize the screw 502 in the desired position against the yoke 512.

The top surface 550 includes an upwardly opening recess 554 formed therein for receiving the anvil 516. The recess 554 has an arcuate or, preferably, spherical bottommost surface portion sized and configured to allow the small anvil 516 to shift when seated in the recess 554. To this end, the anvil 516 has a bottom surface 558 supported on and slidable against the bottommost surface portion. Furthermore, the recess 554 has two pair of diametrically opposed notches, each pair perpendicularly oriented from the other pair for receiving similarly configured prongs of a driver without interfering with the anvil 516 therein. The top surface 550 includes a retainer or staked portion in the form of short tabs located at the opening to the recess 554 and between each notch. Prior to disposing the anvil 516 in the recess 554, the tabs rise upwardly from the top surface 550 in the axial direction so that the tabs do not hinder insertion of the anvil 516. Once the anvil 516 is located in the recess 554, the tabs are deflected over to extend radially into interference with the anvil 516 while still allowing the anvil 516 to move within the recess 554 but be captured therein by the tabs. After assembly, heat or other treatment may be utilized to relieve residual stresses within the bent tabs.

The anvil 516 has a bottom portion 580 with a generally arcuate bottom surface 558 which rests against the bottommost portion of the seat 554. Accordingly, the anvil 516 may pivot or rotate within the recess seat 554. The anvil 516 further includes a seat portion 582 extending centrally upward from the anvil bottom portion 580 to a top surface 584 with a transverse shoulder surface 585 between the anvil portions 580 and 582.

When the rod 16 is inserted within the yoke 512, the side surface 5 of the rod 16 is advanced into contact with the anvil 516. If the bone screw 502 is deflected or secured so that its central axis 544 is not coincident or aligned with the yoke central axis, the anvil 516 is initially deflected or tilted in a similar deflection. As the rod 16 is secured and forced against the anvil 516, the anvil 516 pivotable in the recess 554 will shift to require the minimized distance between the rod 16 and the bottom surface portion of the recess 554.

In order to have a low profile, it is preferred to minimize the height of the anvil 516 while remaining above the top surface 550 of the screw head 536. The anvil top surface 584 is sized so that, when deflected to the deflection of the bone screw 502, at least a portion of the top surface 584 is contact by rod 16 being advanced toward the anvil 516 in the yoke 512. Accordingly, the anvil 516 is self-righting as the rod 16 contacting the anvil top surface 584 forces the anvil 516 to shift to align tangentially its minimum height, as discussed above, with the surface 5 of the rod 16.

As depicted in FIGS. 1K and 1L, the cap 518 and the saddle 520 each define central openings 670 and 672 respectively, through which the clip 519 extends. The cap opening 670 is segmented between a lower portion 670a and an upper portion 670b that steps open to a diameter larger than that of the lower portion 670a. An annular shoulder seating surface 674 is at the transition between the lower portion 670a and the upper portion 670b of the cap opening 670. The upper portion 670b also opens to a recessed bottom surface 671 in the drive socket of the cap member 518.

The clip 519 includes an annular base portion 680 and two resilient prongs or stems 680a, 680b projecting upward therefrom and spaced by an axially extending gap 682 therebetween. Each stem 680a, 680b terminates at their free ends with flanges 681a and 681b including an upwardly facing cam surface that can be ramped or inclined relative to the clip axis, or have a curvature thereto. The cam surfaces aid in insertion of the clip 519 through the openings 670 and 672, and a corresponding lower stop surface 688 is provided at the prong flanged ends 681a and 681b extending normal to clip axis that substantially prevents unintentional removal of the clip 519 back through the openings 670, 672.

The central opening 672 of the saddle 520 also includes an upper portion 672a and a lower portion 672b. The lower portion 672b opens to a concave bottom 700 of the saddle 520 and has a larger diameter than the upper portion 672a so that there is an annular shoulder surface extending therebetween. The enlarged lower portion 672b is sized such that the base portion 680 of the clip 519 is fit and held therein in interference with the surface 672c. Preferably, the diameter of the opening lower portion 672b is kept to a minimum to increase the surface contact area of the saddle surface 700 on the rod 16. The opening upper portion 672a can be sized to have a similar diameter as that of the smaller lower portion 670a of the cap opening 670.

To assemble the cap member 518 and saddle member 520 together, initially the spring clip member 519 is axially inserted in saddle opening 672 with prong free ends 681a and 681b first inserted in enlarged lower opening 672b. With continued axial insertion, the cam surfaces engage and cam against shoulder surface 672c resiliently forcing the spring prongs 680a and 680b toward each other to take up the gap 682 therebetween. With the prongs 680a and 680b pushed together, the lateral outer edges of the cam surfaces are spaced by a distance slightly less than the opening portions 670a and 672a. This allows the clip member 519 to continue to be inserted through the opening 672 including the smaller diameter opening upper portion 672a. Depending on the distance across the undeformed prong upper edges relative to the diameter of opening lower portion 672b, there may also be camming against the saddle surface 700 with some attendant prong deformation to enable the clip prongs 680a and 680b to fit into opening lower portion 672b. Once the prong ends 681a and 681b and specifically prong surfaces 688 thereat clear the opening upper portion 672a, the clip prongs 680a and 680b return to their original undeformed state with surfaces 688 in conforming relation with upper surface 702 of the saddle 520 so that absent exerting a force to bring the prongs 680a and 680b together, the clip member 519 and saddle member 520 stay assembled together.

To complete the assembly process, the prong ends 681a and 681b are next axially inserted in the cap opening 670, and specifically, smaller lower portions 670a thereof. Accordingly, cam surfaces cam against a lower surface 687 of the cap 518 about the central opening 670 therein which forces the resilient stems 680a, 680b together taking up the gap 682 therebetween to allow the clip prongs 680a and 680b to be inserted through the opening portion 670a. Once the clip cam surfaces pass through the lower portion 670a of the cap opening 670, the stems 680a, 680b resiliently return back toward their non-flexed position. After the prongs ends 681a and 681b exit the opening 670, the prongs 680a and 680b will return to their undeformed state, and the stop surfaces 688 will be facing the cap surface 671 and spaced therefrom so that there is play between the connected components, i.e., the cap 518, the saddle 520, and the clip 519, as shown in FIG. 1L. Upon turning the cap 518 to its locked position, the prong ends 681a and 681b reenter the opening upper portion 670b as the saddle member 520 is driven toward the rod 16 shifting the spring clip member 519 axially therewith due to engagement of the surface 672c on the clip base 680 with the stop surfaces 688 brought into abutting engagement with the seating surface 674 to substantially prevent the clip 519 from being unintentionally pulled back through the openings 670, 672 of the cap is turned into its locked position.

The MIS system, described herein, can be used to implant bone fixation devices similar to the ones briefly described above. Such systems are particularly useful during spinal and neurosurgical procedures because the surgeon can need access to locations deep within the body and such access requires the surgeon to reposition or avoid vital tissues and nerves. While the MIS system is useful for performing spinal surgery, it can also be effectively used for non-spinal applications in humans and other mammals. The implants described herein are exemplary, however, and the minimally invasive instrumentation described may be used with a variety of implant forms, spinal and non-spinal, in some cases with minimal or no modification. For example, some or all of the tools described herein may be used for repairs of the hip as well as for repairs of the spine, and they may be used to implant bone screws, fusion devices, and many other prosthetic and non-prosthetic implants, or to perform non-implant repair.

The MIS system can be configured to accommodate both cannulated and non-cannulated implant placement. This allows the system to be tailored to a particular surgeon's preferences. For example, when employing guide wires, cannulated pedicle bone screws along with cannulated tools can be utilized. However, some surgeons find cannulated instruments to be less effective due to the movement constraints resulting from the presence of the guide wire.

The MIS system includes a number of instruments that the physician may use to perform the implant procedure. In sum, the MIS system provides the surgeon with tools for gaining access to the surgical site, for preparing the surgical site, attaching the fixation device, or the connecting member to the surgical site, adjusting the fixation device, and closing the surgical site. The MIS system may include: a Jamshidi needle, a guide wire, a pedicle finder, series dilators, a multistage telescoping dilation tool, a cannulated cutting instrument, obturators, a docking port or sleeve, a facing tool, an awl, a screw driver or other various locking instruments, pushers, inserters, persuaders, yoke manipulators, compression-distraction tools, and a number of other instruments. Examples of these and other tools are described in U.S. patent application Nos. 60/655,983 and 60/722,604 and PCT/US2006/06684 and herein incorporated by reference. The MIS system may include all the surgical tools necessary to accomplish the procedure, or may only include the specialized surgical tools particular to the implant procedure such that the specialized tools must be supplemented by generic surgical instruments used for many different surgeries.

To begin one exemplary procedure, an incision is made and a surgeon percutaneously inserts a Jamshidi needle over the posterior spinal anatomy. The Jamshidi needle can hold the guide wire and thereby direct the guide wire into position. Correct guide wire placement is important because the surgeon can use the guide wire to direct where the implant and/or instruments are to be located. In another form, the surgeon can rely on tactile feedback to determine where the implants and various tools should be inserted, or the surgeon may employ fluoroscopic equipment to determine such placement visually. If the guide wire is used, it is driven to a predetermined depth into the target pedicle bone of the selected vertebral segment. After the guide wire is secured, the surrounding tissue is stretched using various dilation techniques. The surrounding tissue may also be incised to provide passage of the MIS system tools. Subsequent to tissue dilation and/or incision a docking port is inserted into the percutaneous opening.

The docking port is the minimally access window portal through which some steps of the surgery are performed. In one form, the docking port has an arm or handle such that it can be anchored during surgical procedures, such as to an iron intern. In another form, the docking port may have docking fasteners such that the docking port can be fixed to the bone during surgical procedures. After the docking port is secured into position, the surgeon can prepare the bone for receiving the anchor. A facing tool is sometimes used to resurface the bone to a more desired contour such as concaved, domed, flattened, or another beneficial shape. Before the anchor is inserted, an awl, or other instrument can be used to create a depression or opening on the bone surface at the location where the anchor will be set.

As briefly mentioned above, yoke manipulators are employed to assist insertion of the bone anchor with the yoke attached. Each yoke manipulator is positioned about the yoke before being inserted. The yoke manipulators have two portions, an inner sleeve that includes the portion that is arranged about the yoke and an outer sleeve or restraint that is slid down the inner sleeve to secure the manipulator around the yoke. Having the yoke manipulators and the yokes secured relative to one another allows the surgeon to correctly align the yokes after they have been inserted into the wound. Correct alignment is important because the connecting member is eventually positioned within each yoke. After the yoke manipulator has been secured to the yoke, the yoke manipulators and bone anchors are advanced down the docking port. A screw driver can also be advanced with the yoke manipulator. The screw driver rotates the anchor into position on the pedicle bone. At this point in the procedure, the docking port may be removed, although the yoke manipulator typically remains within the incision, to facilitate insertion of the connecting member. Before insertion of the connecting member, the surgeon typically repeats the procedure to insert the other bone anchor(s).

After the bone anchors, yokes, and yoke manipulators are inserted and the manipulators are aligned, the connecting member may be inserted. At least one of the yoke manipulators includes a pair of slots, one on each side of the manipulator and an opening toward the yoke, to allow for passage of the connecting member. One other yoke manipulator has at least one slot opening toward the yoke allowing for insertion of the connecting member into the yoke. The connecting member is fed between the slots of the yoke manipulators by a rod inserter. The yoke manipulators along with the rod inserter can facilitate placement of the connecting member into a position spanning the yokes, without requiring another opening or incision into the body other than the openings used to attach the anchors. After the connecting member is positioned within the yokes, a closure cap is inserted into the yoke and rotated such that the connecting member is secured into a pre-lock position such that the connecting member and yokes can move relative to one another. The yoke manipulators and bone anchors can be moved together or apart from one another along the connecting member. After positioning of the bone anchors, the caps are moved to the final-lock position. The yoke manipulators may then be removed from the bone anchors along with any other tools and instruments, such as the docking ports if not previously removed. After removal of the tools, the surgeon closes the wound. The MIS system allows for insertion of an implant without unnecessary trauma to the body, and more particularly to the tissue surrounding the implant. Further, the system provides the surgeon with guidance during the procedure without being unduly rigid.

In one form of the procedure, the surgeon first makes the incision into the skin. Such an incision could be made by a number of incising or cutting instruments. Thereafter, the surgeon proceeds by percutaneously inserting a Jamshidi needle. The Jamshidi needle and a guide wire are typically coupled together to facilitate insertion of the guide wire. The handle of the Jamshidi needle includes a click wheel. After the guide wire is inserted into the Jamshidi needle, the click wheel is advanced until a guide wire is held firmly into position. Proper implant placement is required for a successful procedure and the surgeon must correctly identify the pedicle anatomy to which the device will be attached. Therefore, the surgeon can use the Jamshidi needle over the posterior spinal anatomy to provide tactile feedback for determining guide wire placement. In another form, a fluoroscopic imaging device is used to assist the surgeon in placing the device in the proper position. Various radio-imagery may be utilized to monitor the procedure in addition to assuring proper placement of tools and components. Using imaging equipment prevents placing the tools incorrectly or driving the instruments or implants in the wrong location, or too deeply into the body tissue, as this could harm vital body tissue, nerves, etc.

After it is positioned, the guide wire is driven to a predetermined depth to firmly secure the guide wire for the remainder of the procedure. A portion of the guide wire typically extends out of the tip of the Jamshidi needle. To secure the guide wire, the handle of the Jamshidi needle is typically tapped with a mallet or other tool to thereby drive the portion of the guide wire extending from the tip of the Jamshidi needle into the bone. After the guide wire has been tapped into the bone and secured, the Jamshidi needle is removed from the incision by releasing the click wheel and leaving the guide wire secured to the bone. While the above procedure is one way the guide wire may be positioned, a number of other procedures exist. Further, use of the guide wire varies by surgeon and while some surgeons prefer to use the guide wire throughout the procedure, others prefer not to use the guide wire at all, and still others prefer to use the guide wire during only a portion of the procedure. For example, some surgeons may employ the guide wire until the bone anchors are to be inserted. Whereas, other surgeons will use the guide wire during more steps of the procedure, including during insertion of bone anchors, which may require the use of cannulated anchors that can be slid down the guide wire.

The guide wire is typically secured where the bone anchors will be attached. The guide wire is preferred to have a self-cutting and self-tapping thread, however, the thread type and insertion means vary by surgeon preference. Alternatively, the guide wire may have a non-threaded sharpened end for advancement through soft tissue and piercing the bone. Such a guide wire is preferably constructed of biocompatible metals or alloys such as stainless steel, titanium, or nitinol.

Following placement of the guide wire, the tissue surrounding the guide wire is stretched or dilated. To stretch the tissue, a number of open ended cylinders or series dilators can be used. The series dilators are tubes with one end having a sloped nose that can slowly stretch the tissue from around the guide wire. The tubes advanced into the incision incrementally increase in diameter. Thus, as each tube is inserted into the incision, the tissue surrounding the guide wire is expanding. To simplify the dilation procedure, a dilation tool such as the dilation tool disclosed in U.S. patent application Ser. No. 11/466,262, filed on Aug. 22, 2006, may be employed.

In another form, an obturator or a set of obturators can be used to dilate the tissue surrounding the surgical site. When a set of obturators is employed, the diameter of each subsequently employed obturator increases. As with many of the tools, the obturators may be used in conjunction with a guide wire if the tool is cannulated. If cannulated, the opening of the obturator is advanced down the guide wire and into the incision. The obturators have a sloped nose that when pushed into the incision will stretch the surrounding tissue to accommodate the increasing diameter of the obturator. A shaft of the obturator may be the same, reduced, or enlarged in diameter, compared to the nose. The obturator preferably includes transitional sloped or arcuate portions to ease retraction of the obturator. The obturator may also include a flange, a boss, threads, or locking pins to secure the obturator into position. In addition, the end of the obturator opposite the nose may include a handle or other structure suited for gripping the instrument to control movement of the instrument into the opening.

In yet another form, the tissue surrounding the guide wire is incised, instead of stretched, to provide access for the MIS system tools and fixation device. A scalpel or cutting instrument may expand the previous incision to accommodate the remaining MIS system procedure. A cannulated cutting tool that includes a handle, a cylindrical body, and fins may be used to increase the size of an opening. The fins may cut precise openings in the tissue surrounding the guide wire.

After the surrounding tissue has been stretched or incised sufficiently to accommodate the MIS system tooling, a docking port or sleeve 64 may be slid down the series dilators, the telescoping tissue dilator, or other tool located within the incision. Sliding the docking port 64 into the incision retains the surrounding tissue about the docking port 64, which now serves as an opening or window in the tissue, large enough to accommodate the tools used during portions of the MIS procedure. In another form, the docking port 64 may be advanced into the tissue with an obturator. If the obturator is cannulated, the obturator and docking port 64 are slid down the guide wire.

The docking port 64 is typically the access window through which a portion of the MIS system procedure is conducted; however, the surgeon may choose to insert the bone anchors 20 without the docking port 64. The docking port 64, illustrated in FIGS. 3-6, includes a handle 66, a cylindrical body 68, and an angled end 70. The handle 66 may include channels 72 to increase grip. An articulating arm, such as an iron intern, may attach to the handle 66 of the docking port 64 to secure the docking port 64 in position. Before the docking port 64 is secured into position for the insertion of the bone anchors 20, the angled end 70 of the docking port 64 is inserted into the incision. The angled end 70 is contoured to fit adjacent the spine. A first edge 74 is sized to fit toward the center of the patient and a second edge 76 is sized to face toward the side of the patient. More particularly, the first edge 74 is positioned adjacent to the transverse process. The edges 74, 76 come together at tip 78 which is slightly off-set from the center of the cylindrical body to facilitate a better fit with the spine. In one preferred form, the inner diameter of the docking port 64 is about 0.646 inches, the outer diameter is about 0.721 inches, the distance from the center of the cylindrical body 68 to the tip of the handle 66 is about 2.622 inches, and the length of the cylindrical body 68 is 5.326 inches. Further, the docking port 64 is made of biocompatible material. In one preferred form, the material is polyetheretherketone or PEEK. This allows the docking port 64 to provide a working channel, to electrically shield the bone anchor 20, and further, if the docking port 64 is PEEK, and therefore radiolucent, the docking port 64 will not interference with fluoroscopy.

After the docking port 64 is positioned adjacent to the vertebrae and secured into position, a number of various instruments can prepare the implant site. For example, to prepare the implant site, the surgeon may need to remove an osteophyte overlying the area where the anchor 20 will be seated. A surgeon can remove such interfering structures using a facing tool. The facing tool can be used to smooth or refine the bone surface, thereby creating a flattened area suitable for seating implants. The facing tool may also be cannulated to accommodate the guide wire or may not be cannulated, having other structure to facilitate position of the tool within the docking port 64.

In one embodiment, the facing tool includes a generally flat cutting surface with cutting edges that remove boney material. The cutting edges remove bone as the tool is rotated and a recess or a bone chip reservoir that provides a space where the removed material may accumulate. In addition to a flat cutting surface, the cutting surface may also have another contour such as convex or concave. The facing tool typically includes a handle to grip the tool and a depth stop, typically a stop collar that engages the docking port 64 or other instruments. The depth stop helps prevent the tool from being advance too far into the bone. In addition, the facing tool includes a positioning member or centering portion. The centering portion of the facing tool is sized to be received inside the docking port 64. Centering the facing tool ensures correct placement of the smoothed site and further prevents the cutting surface and cutting edges from wearing against the docking port 64.

In another form, an awl may prepare the implant site by perforating the cortex of the bone overlying the pedicle. A cannulated awl may be used over the guide wire by sliding the cannulated awl down the guide wire into the docking port 64 and toward the implant site. If the guide wire is not employed, the awl can be visually placed at the implant site or the awl may include a centering portion that guides the awl to the implant site. The awl is driven into the bone by tapping on the end projecting out from the docking port 64 with a mallet. After the cortex of the bone is breached and a depression or opening is made, the awl can be removed from the docking port 64. If the surgeon chooses, the depression can be created by rotating the awl instead of tapping on the end.

In another form, a pedicle finder or another drilling tool can be used to prepare the implant site. The pedicle finder is advanced down the docking port 64 toward the bone. Once positioned adjacent the bone, the pedicle finder can create a pilot hole for the bone anchor 20. The surgeon must take care not to make the hole too deep. Whether or not the surgeon taps a pilot hole often depends on the type of bone anchor 20 and the surgeon's preference.

Whether a pilot hole is tapped by the pedicle finder or a depression is made by the awl, the surgeon may also wish to use a probe to assess the position of the hole or depression to ensure that it has not veered into an unintended or unsafe location. Some surgeons have found that verifying the hole or depression position can be difficult when employing a guide wire because the instruments and the bone anchors 20 are constrained to the guide wire. As suggested earlier, the guide wire can be removed before insertion of the bone anchor 20 and is preferred by many surgeons because an improperly placed guide wire can cause incorrect implant placement, which can have potentially harmful results.

After the implant site has been prepared, the surgeon may now insert the anchor 20 into position. A number of methods and instruments are available for delivering the bone anchor 20 and yoke 22 to the surgical site. Each bone anchor 20 is mated to one yoke 22 and the two are advanced into position together. The yoke 22 and the bone anchor 20 may be a fixedly or polyaxially connected. The methods and instruments can be used in varying combinations. The tools used to seat the bone anchors 20 are typically advanced through the docking port 64.

Figure 7:
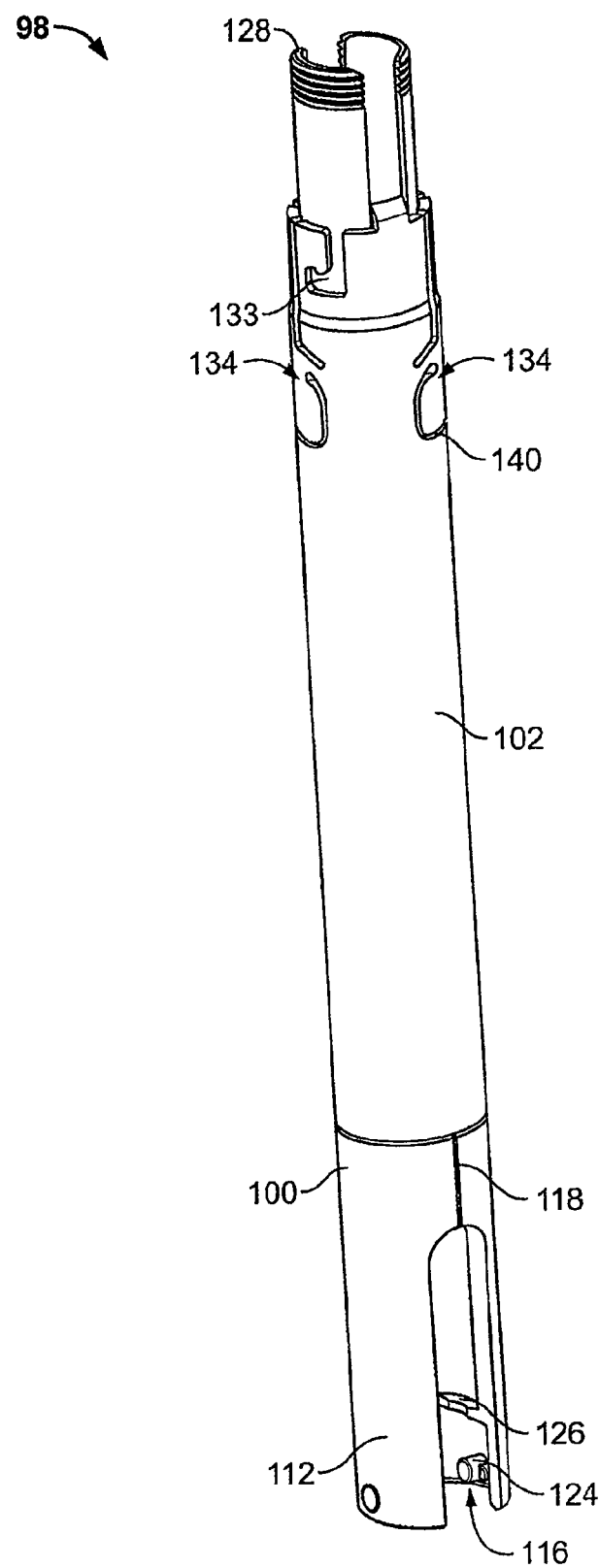
FIG. 7 is a perspective view of a short slot yoke manipulator.
Figure 8:
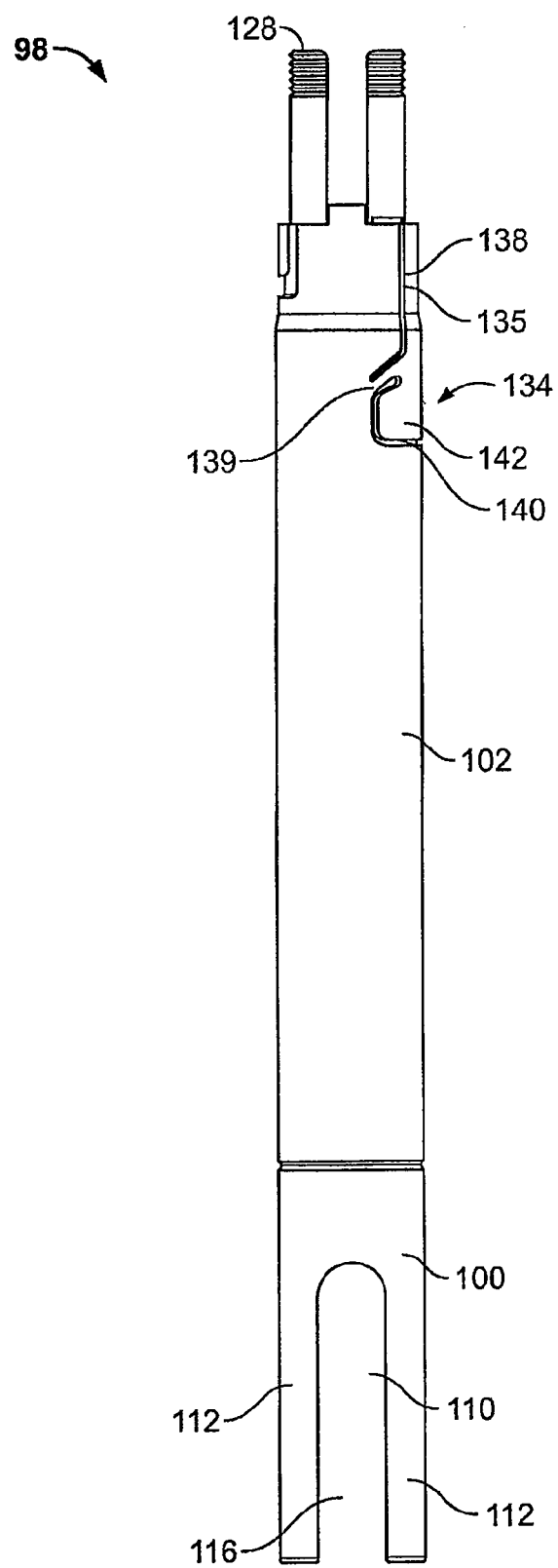
FIG. 8 is a front view of the yoke manipulator of FIG. 7.
Figure 9:
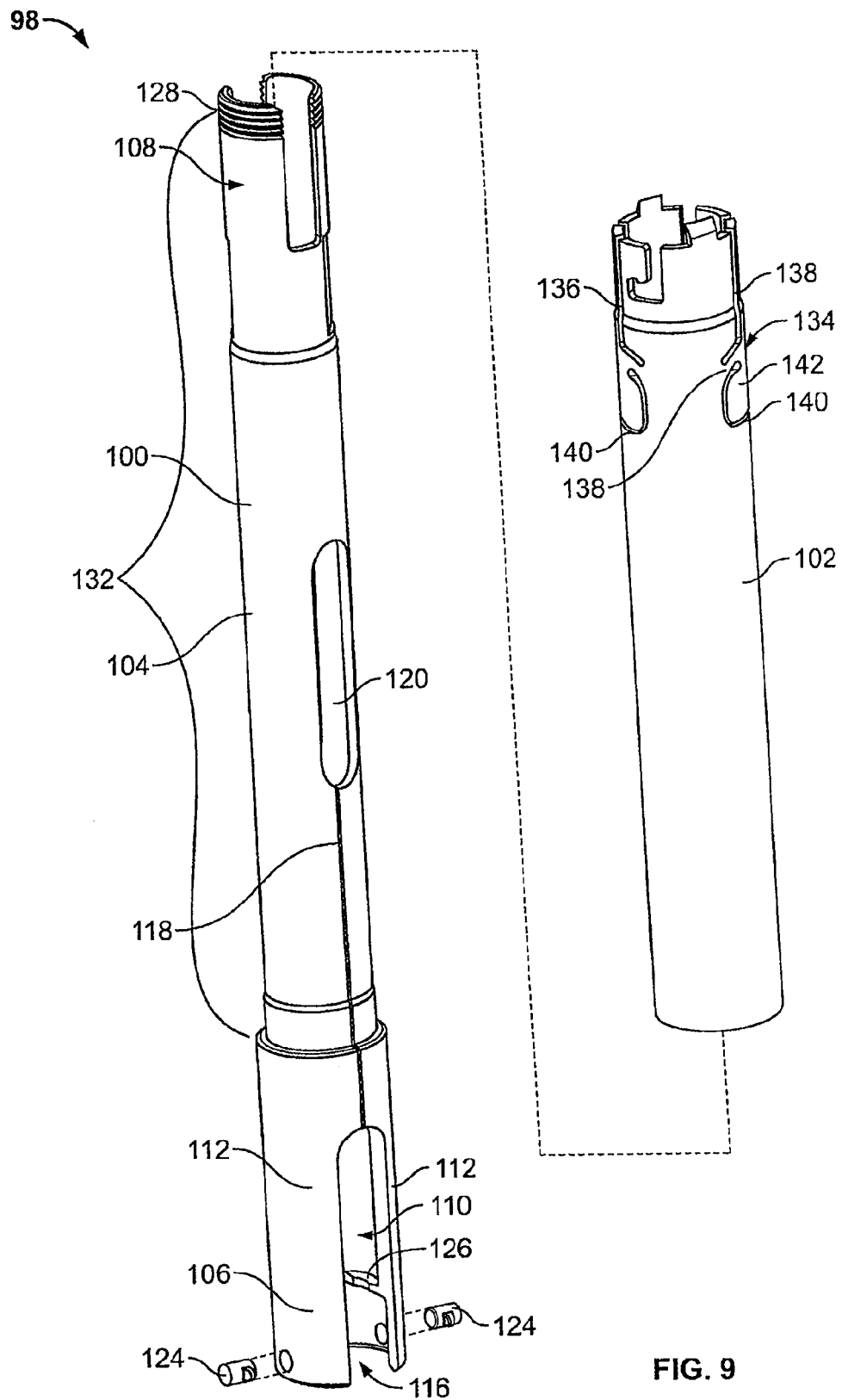
FIG. 9 is an exploded view of the yoke manipulator of FIG. 7.
Figure 10:
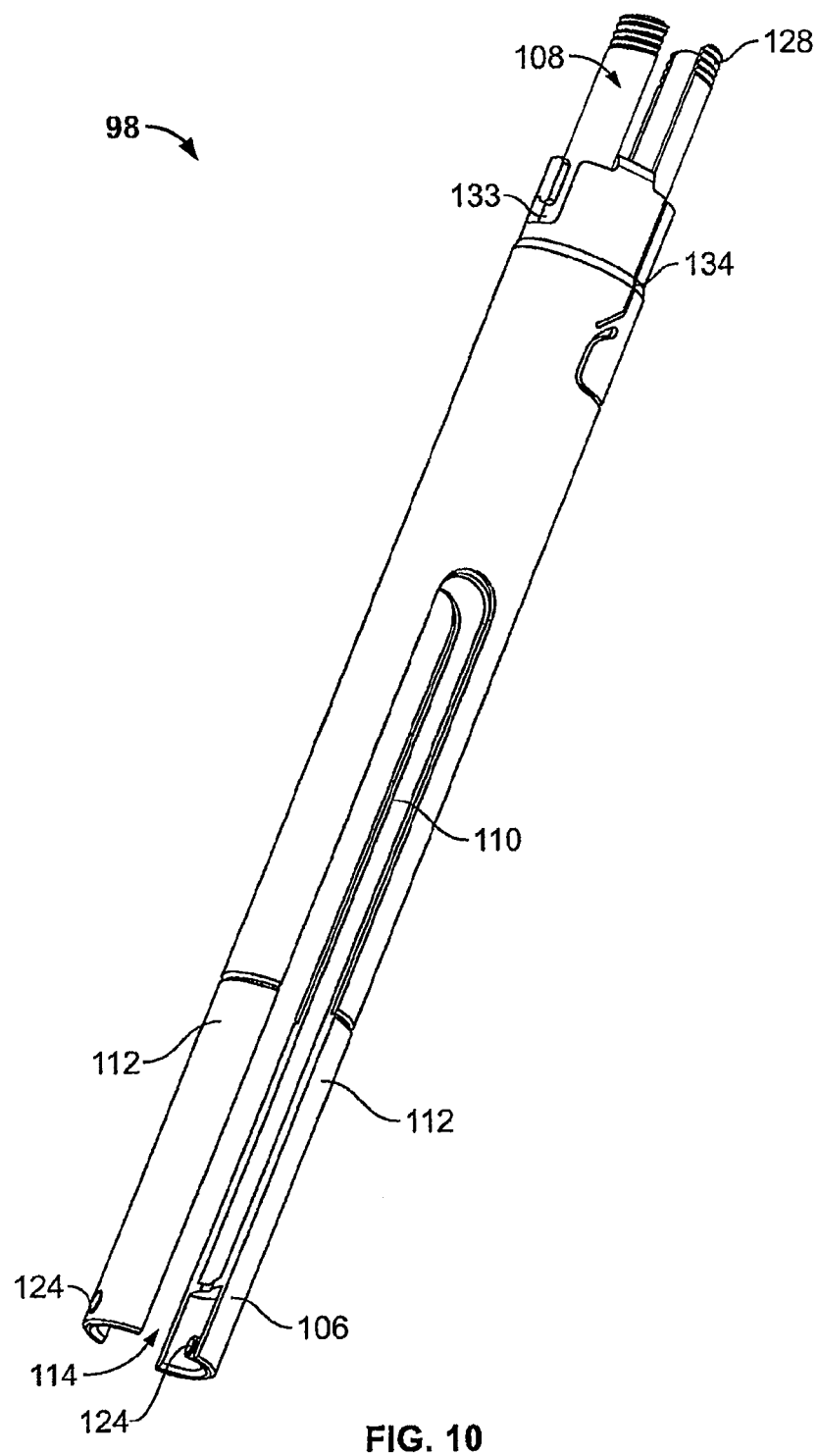
FIG. 10 is a perspective view of a long slot yoke manipulator.
Figure 12:
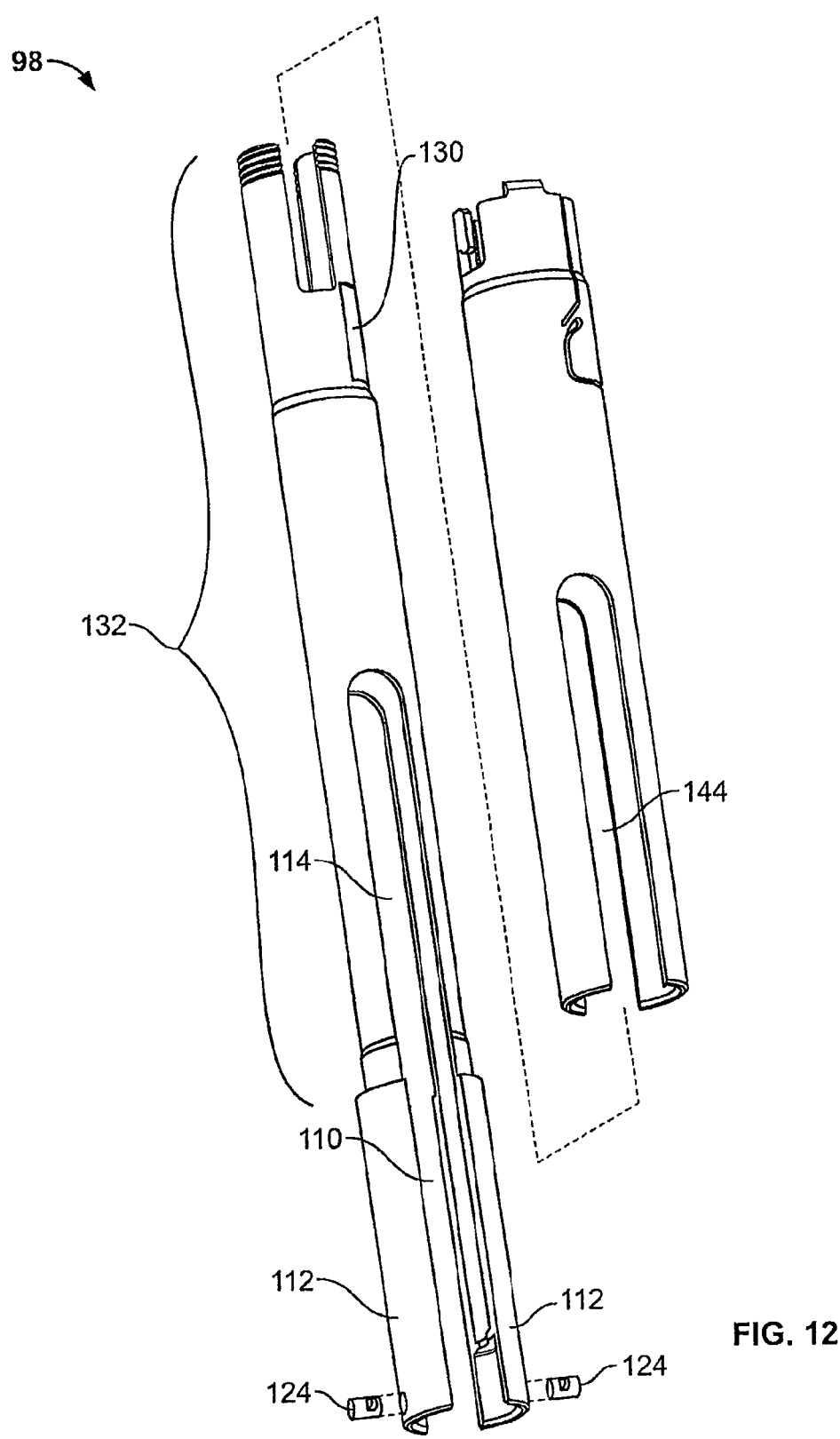
FIG. 12 is an exploded view of the yoke manipulator of FIG. 10.

In one form, the bone anchor 20 is delivered to the surgical site with a yoke manipulator 98. As shown in FIGS. 9 and 12, the yoke manipulator 98 is comprised of two cylindrical sleeves 100 and 102. The inner cylindrical sleeve 100 includes a main shaft body 104 having a first end 106 that is inserted into the incision and a second end 108. The first end 106 includes two shaft slots 110 that create two shaft arms or prongs 112. The two shaft slots 110 can vary in length. FIGS. 10-12 illustrate a long slot 114 that begins at the first end 106 and extends down the shaft pass the midpoint of the sleeve 100. FIGS. 7-9 illustrate a short slot 116. The manipulators 98 having short slots 116 also typically include a channel 118 leading to an internal slot 120. The material used for the manipulator 98 can impact the length of the slots 110 that can be made. The manipulators 98 may have a number of slot lengths. In another form, instead of using a long slot 114 and a short slot 116, a medium length slot 110 may also be used and further both slots 110 may be the same length. The slots 110 allow for some movement of the prongs 112. In addition, the slots 110 provide for clearance for manipulation of the connecting member 26, as described below. The prongs 112 are typically placed around a portion of the yoke 22. After the prongs 112 are positioned around the yoke 22, the outer cylindrical sleeve 102 is slid into position over the inner cylindrical sleeve 100 thereby securing the yoke 22 and bone anchor 20 relative to the yoke manipulator 98.

The portions of the prong 112 that surround a portion of the yoke 22 typically include a boss, recess, flange, or other retainer to engage a complementary structure on the yoke 22. In one embodiment depicted in FIGS. 7-12, each of the prongs 112 includes a boss or pin 124 located on the inside surface of the prongs 112 and located relatively close to the end of the inner cylindrical sleeve 100. The pins 124 help prevent the yoke 22 and anchor 20 from prematurely separating from the manipulator 98. In one form, as shown in FIGS. 9 and 12, the pins 124 include a centrally located cylinder shape flanked by two semi-ovals. The somewhat irregular shape can create a more secure connection between the yoke and the inner cylindrical sleeve 100. The inside surface of the prongs 112 further may include a radially inward extending flange 126 to provide a stop limiting axial movement of the yoke 22 within the sleeve. On the second end 108, the inner sleeve 100 includes a connecting structure 128, such as threads, flanges, slots, or bosses, to connect other tools or instruments such as a screw drive assembly and a guide bar, among others. In addition, the second end 108 includes a mating structure such as a flat 130, to mate with structure on the outer sleeve 102.

The inner sleeve 100 has a recessed section 132 that accommodates the outer cylindrical sleeve 102. The recessed section 132 begins at the second end 108 and extends down the shaft body 104 toward the prongs 112. The outer cylindrical sleeve 102 serves as a restraint on the movement of the inner sleeve 100, more particularly the prongs 112 that are secured about the yoke 22. As suggested above, the outer sleeve 102 prevents or limits the movement of the prongs 112 when the sleeve 102 is mated with the inner sleeve 100. The outer sleeve 102 includes a positioner 133 such as a slot, flange, boss or recess for engagement of an instrument. In addition, this positioner 133 can mate the outer sleeve 102 with other instruments. After the outer sleeve 102 is slid over the inner sleeve 100, the two sleeves mate together by a spring 134 of the outer sleeve 102. When the spring 134 is depressed, elastic deformation of the outer sleeve 102 allows the sleeve 102 to be removed from around the inner sleeve 100 by raising a finger portion 135 of the spring 134 away from a flat 130 of the inner sleeve 100. In one form, the spring 134 is comprised of three separate channels 136, 138, 140 in the outer sleeve 102. As shown in FIGS. 8-9, the channels or slits 136 and 138 define a finger 135 and the generally U-shaped slit 140 defines a tab 142. A gap 139 is located between the channel 140 and the slit 136, 138. The tab 142 functions as a lever, and when the tab 142 is depressed the finger 135 raises and disengages from the flat 130 of inner sleeve 100.

As shown in FIGS. 10-12, the outer sleeve 102 that mates with the longer slot 114 manipulator may also have a slot 144 similar to the slot 110 in the inner sleeve 100. The slots 110, 144 allow for passage of the connecting member 26 during the implant procedure. In a preferred form, one yoke manipulator 98 is used for each bone anchor 20. Therefore, if the procedure requires two anchors 20, then two yoke manipulators 98 are used and if the fixation device has three bone anchors 20, then three yoke manipulators 98 are employed. Since the slots 110 and 144 allow for passage of the connecting member 26, the manipulators 98 and slots 110, 144 are preferably aligned. Structure facilitating alignment of the manipulators 98 can be on the inner and outer sleeves 100, 102.

After the bone anchors 20 are positioned adjacent to the bone, the bone anchors 20 are typically driven into the bone by rotating a screw driver. The screw driver is sized to fit within the yoke manipulator 98. The screw driver includes a shaft, with a positioning structure preferably in the form of a pin, boss, flange, or other structure complementary to the yoke manipulator 98. In addition, the screw driver includes a head with a set of prongs that mate with the anchor 20 such that when the screw driver is rotated, the anchor 20 advances into the bone. The screw driver may also include a removable capture, such as a sleeve with internal threads, for mating the screw driver and the manipulator 98, and thus the prongs are more easily engaged with the head of the bone anchor 20. In one form, the capture is comprised of threads, but another connection, such as a bayonet style connection can be used. Opposite the prongs, the screw driver includes an end that can mate with a removable handle, ratchet, or other attachment. Further, the shaft of the screw driver may include a guide portion that centers the screw driver within the yoke manipulator 98. The screw driver can be inserted into the incision with the yoke manipulator 98 or can be advanced down the yoke manipulator 98 after the anchor 20 has been positioned in the pilot hole. After the bone anchor 20 has been seated in the bone, the screw driver is removed from the yoke manipulator 98.

After the anchors have been driven into the bone, the spinal rod or connecting member 26 is inserted to span between the yokes 22. During the insertion of the connecting member 26, the manipulators 98 and slots 110 and 112 are aligned relative to one another. Alignment of the manipulators ensures that the yokes 22 are aligned such that the connecting member 26 can be positioned within the yokes 22. The alignment is typically accomplished with a strut or guide bar 160. However, the connecting member 26 could be inserted without the use of a guide bar 160. The guide bar 160 has structure that, when mated with the yoke manipulators 98, facilitates alignment of the yoke manipulators 98 relative to one another.

Figure 13:
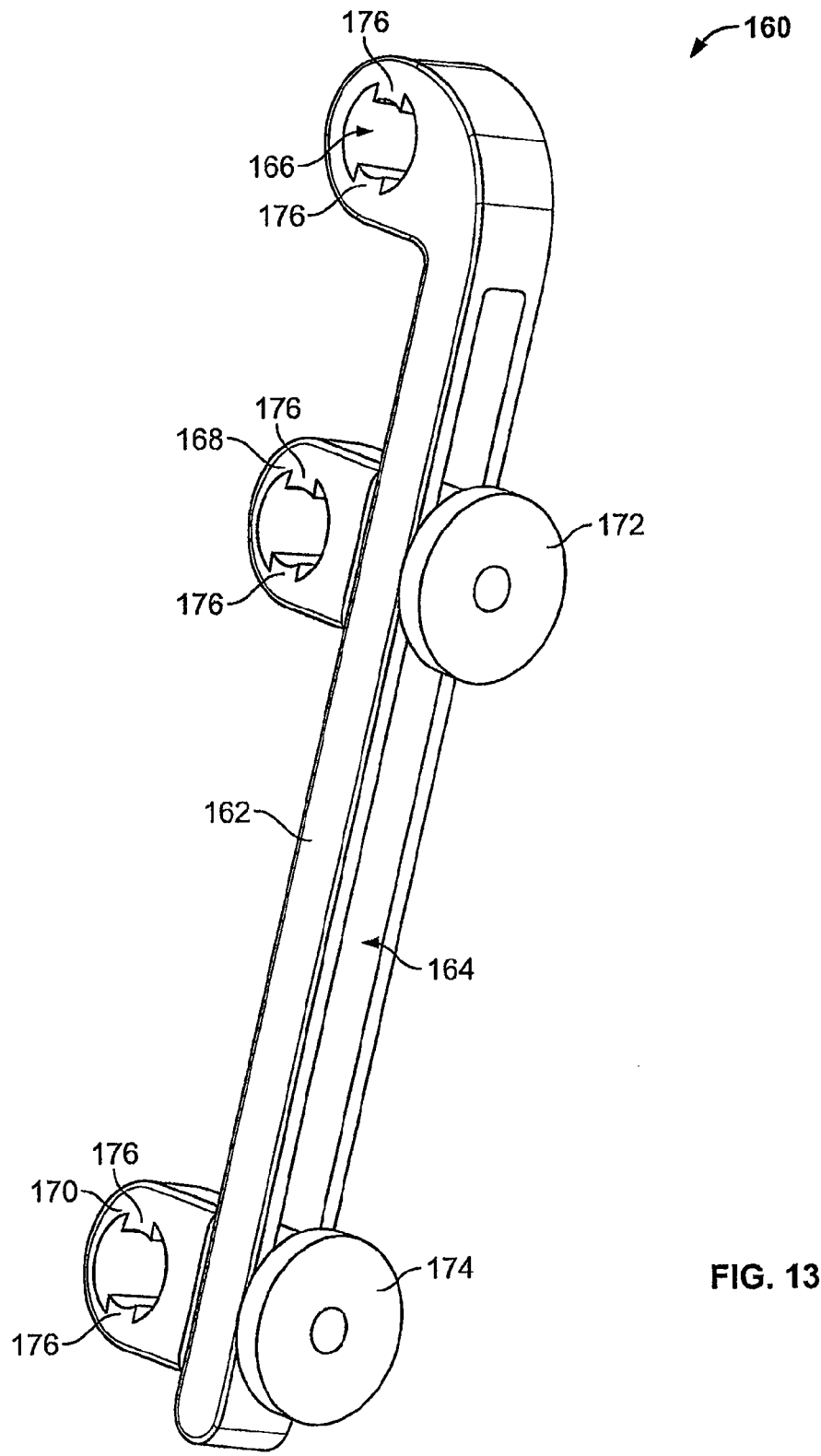
FIG. 13 is a perspective view of a guide bar.
Figure 14:
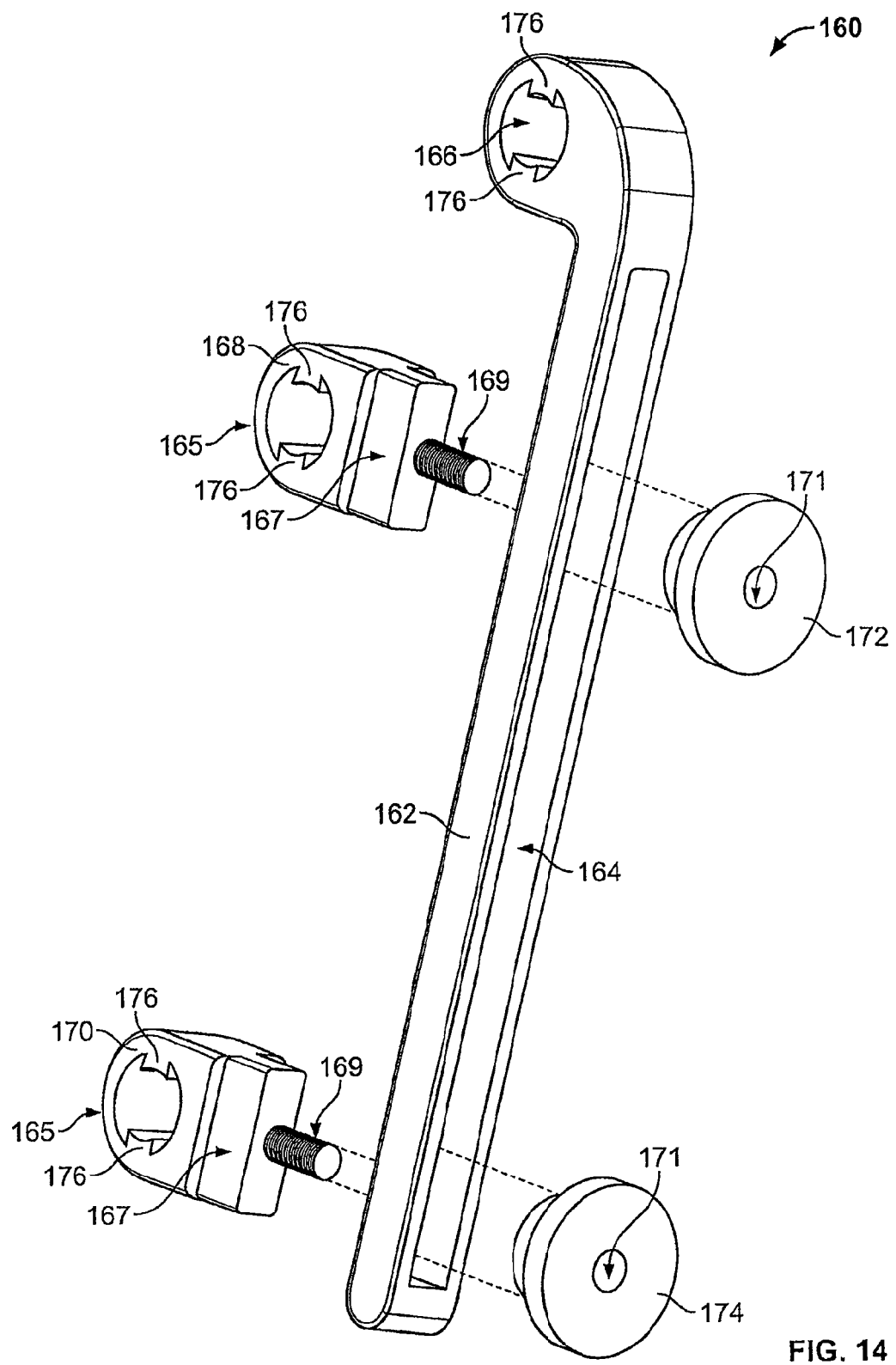
FIG. 14 is an exploded view of the guide bar of FIG. 13.

As shown in FIGS. 13 and 14, the guide 160 typically includes a guide body 162 having a horizontal slot 164 and an end opening 166. Within the horizontal slot 164 are located sliding attachment brackets 168 and 170 oriented within a slide body 165, which can be secured into position by set nuts 172 and 174. The slide body 165 includes a reduced portion 167 that fits within the horizontal slot 164. Attached to the reduced portion 167 of the slide 165 is a threaded portion 169. The threaded portions 169 engage threaded openings 171 in the set nuts 172, 174. The openings 168, 170 are movable with respect to opening 166 to accommodate the spinal anatomy of different patients. The opening 166 and attachment brackets 168, 170 are generally circular with two projections 176 to secure the connection between the guide 160 and the yoke manipulators 98 that are mated with the guide 160. The projections 176 can fit within the connecting structure 128 on the second end 108 of the manipulator 98 illustrated in FIGS. 7-12. Therefore, the physician can align the slots on the first end 106 of the inner sleeve 100 by aligning the connecting structure 128 on the second end 108. In one preferred embodiment, the guide body 162 includes etch marks so that the physician can determine what length connection member 26 is required. To adjust the position of the attachment brackets 168, 170, the nuts 172, 174 are unscrewed and then the attachment brackets 168, 170 can move within the horizontal slot 164.

Figure 15:
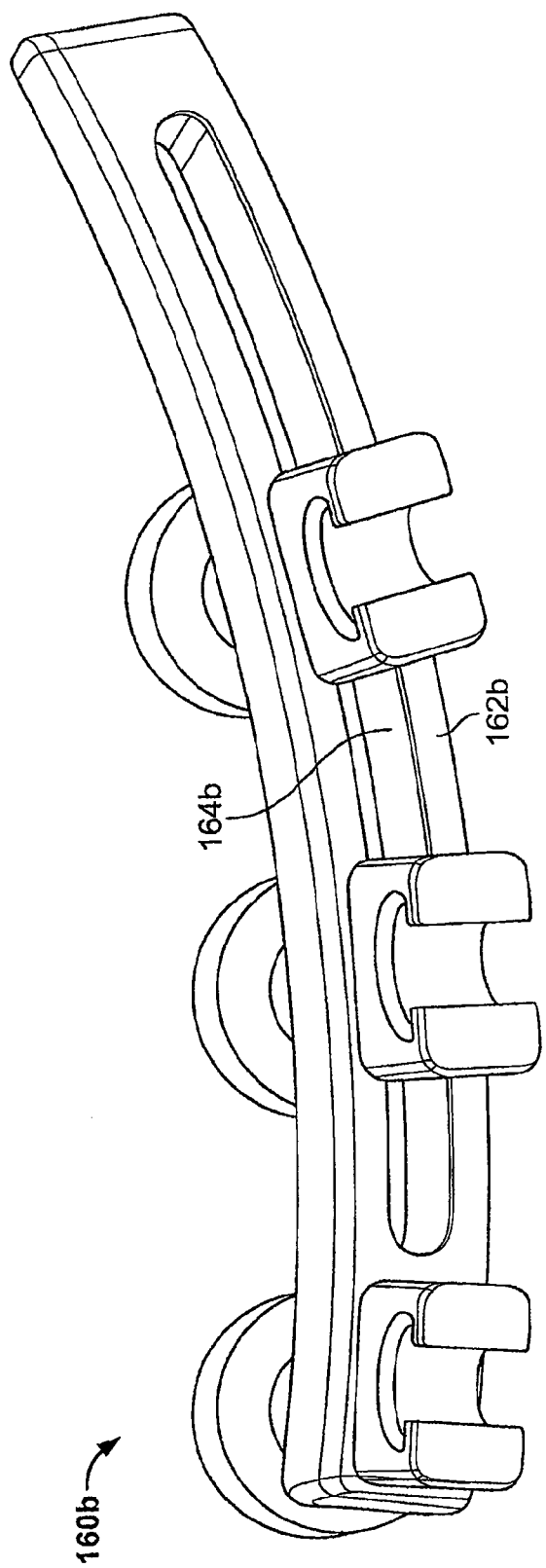
FIG. 15 is a perspective view of another guide bar.
Figure 16:
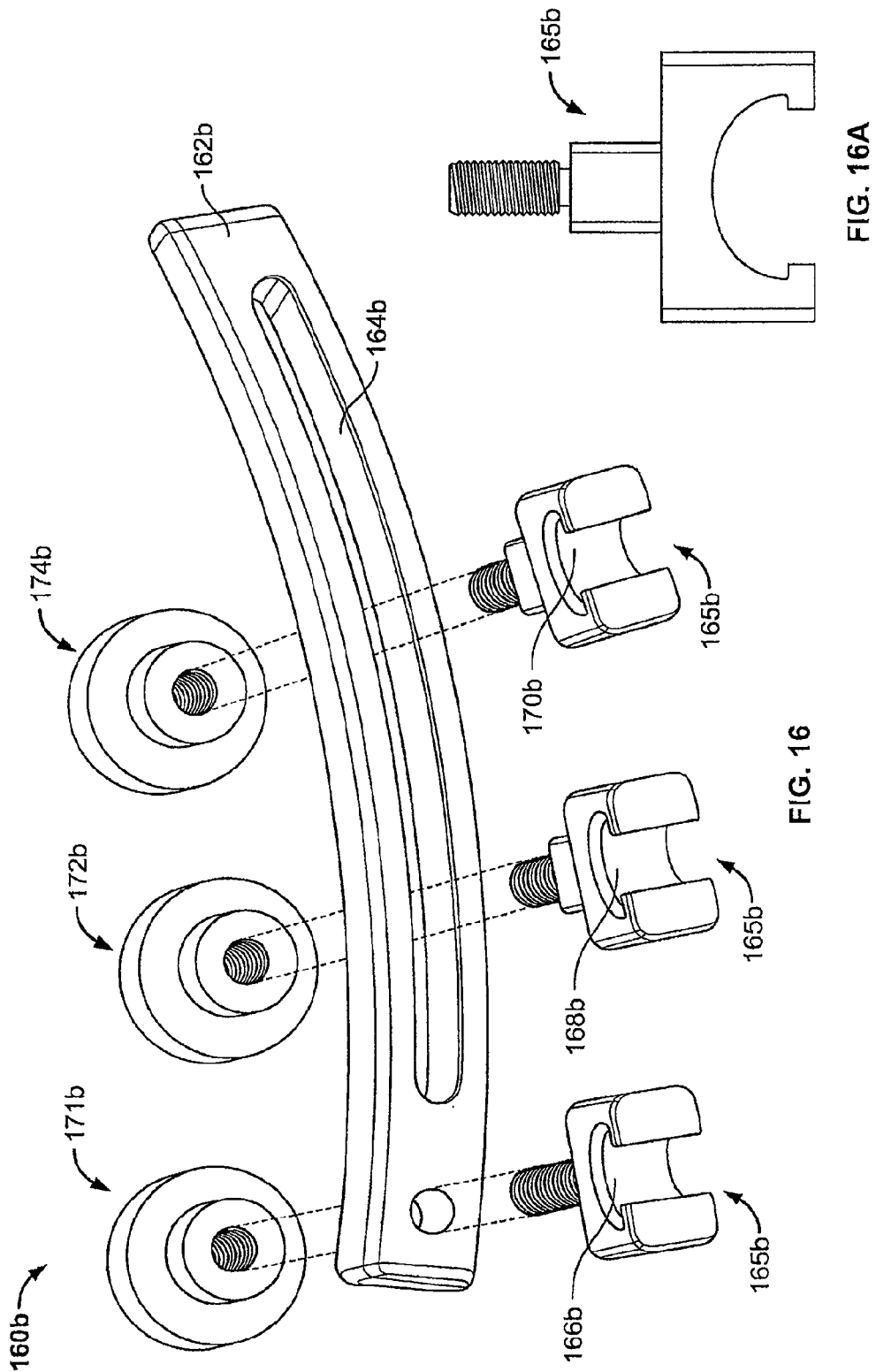
FIG. 16 is an exploded view of the guide bar of FIG. 15.
Figure 17:
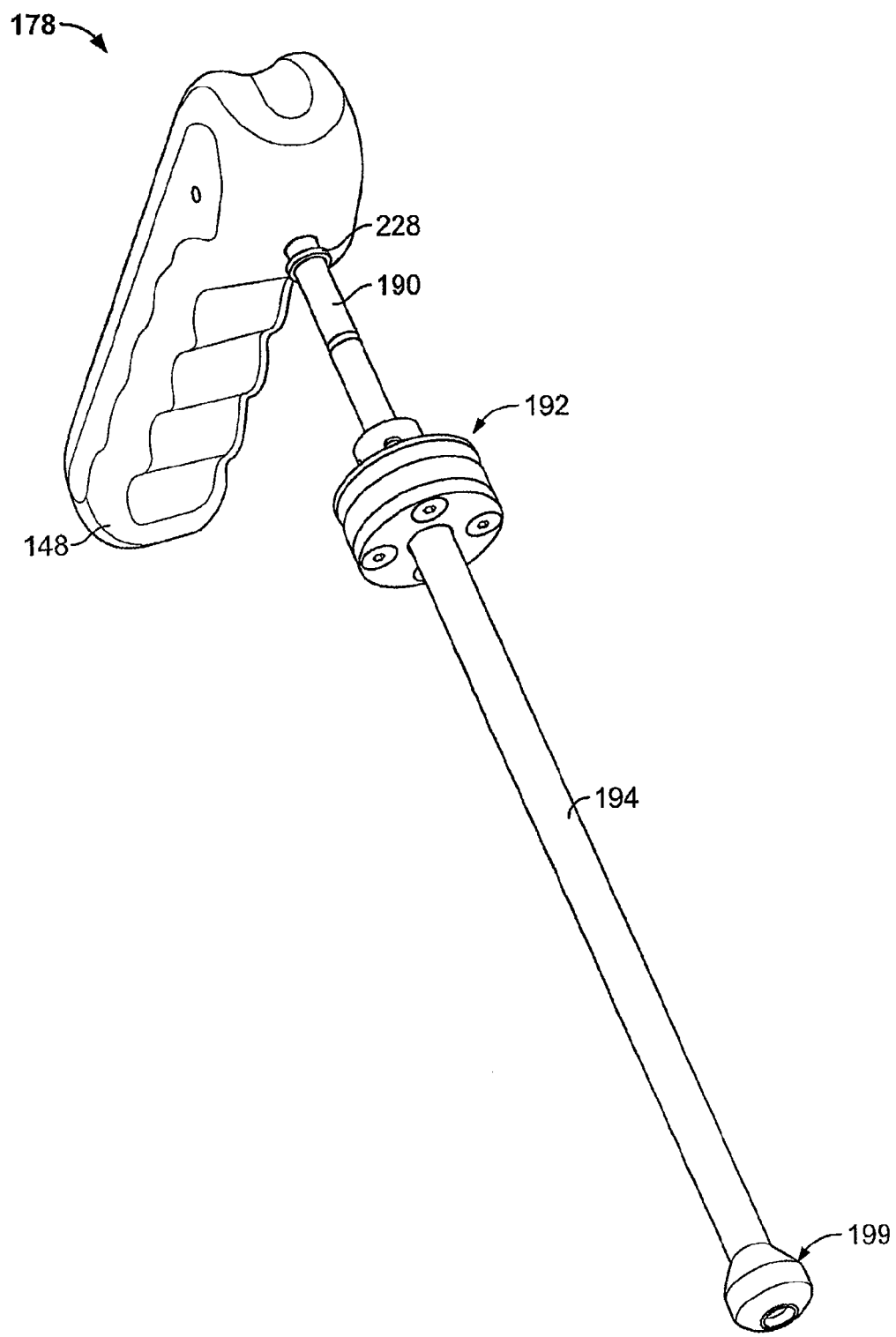
FIG. 17 is a perspective view of a rod inserter having an outer sleeve in a first stage of rod insertion.
Figure 18:
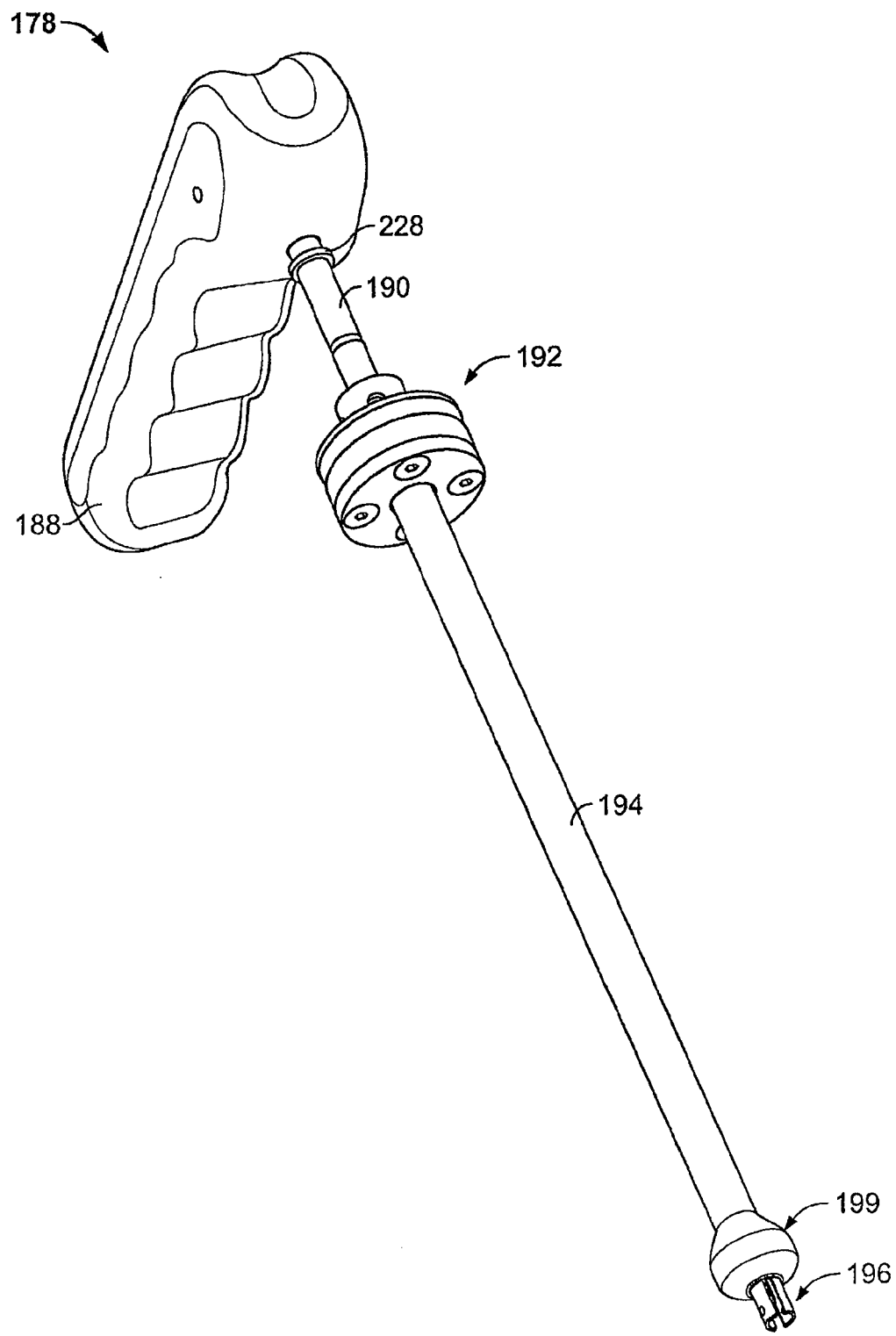
FIG. 18 is a perspective view of the rod inserter of FIG. 17 having the outer sleeve in a second stage of rod insertion.
Figure 19:
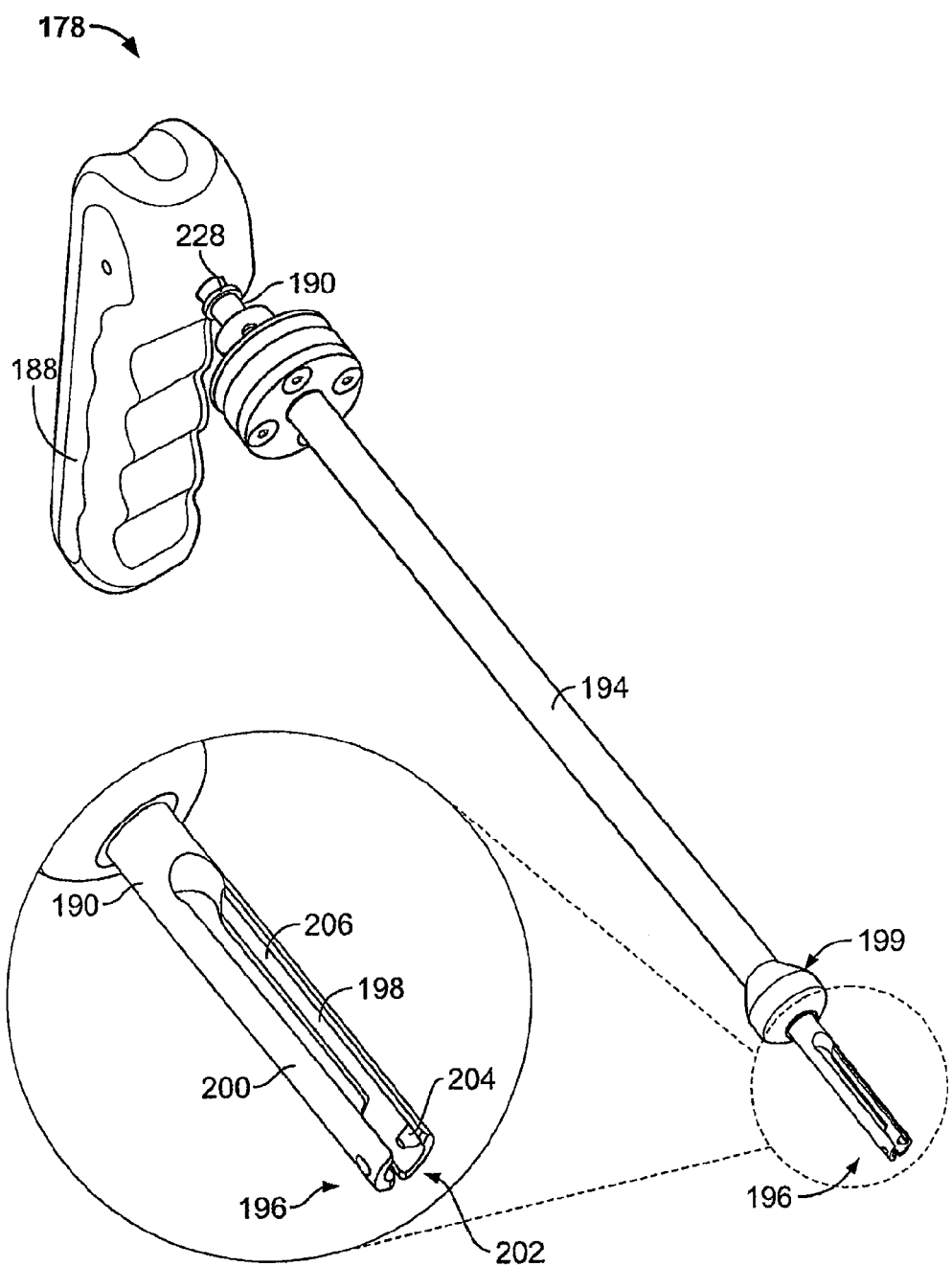
FIG. 19 is a detailed perspective view of the rod inserter of FIG. 17 having the outer sleeve in a third stage of rod insertion.
Figure 20:
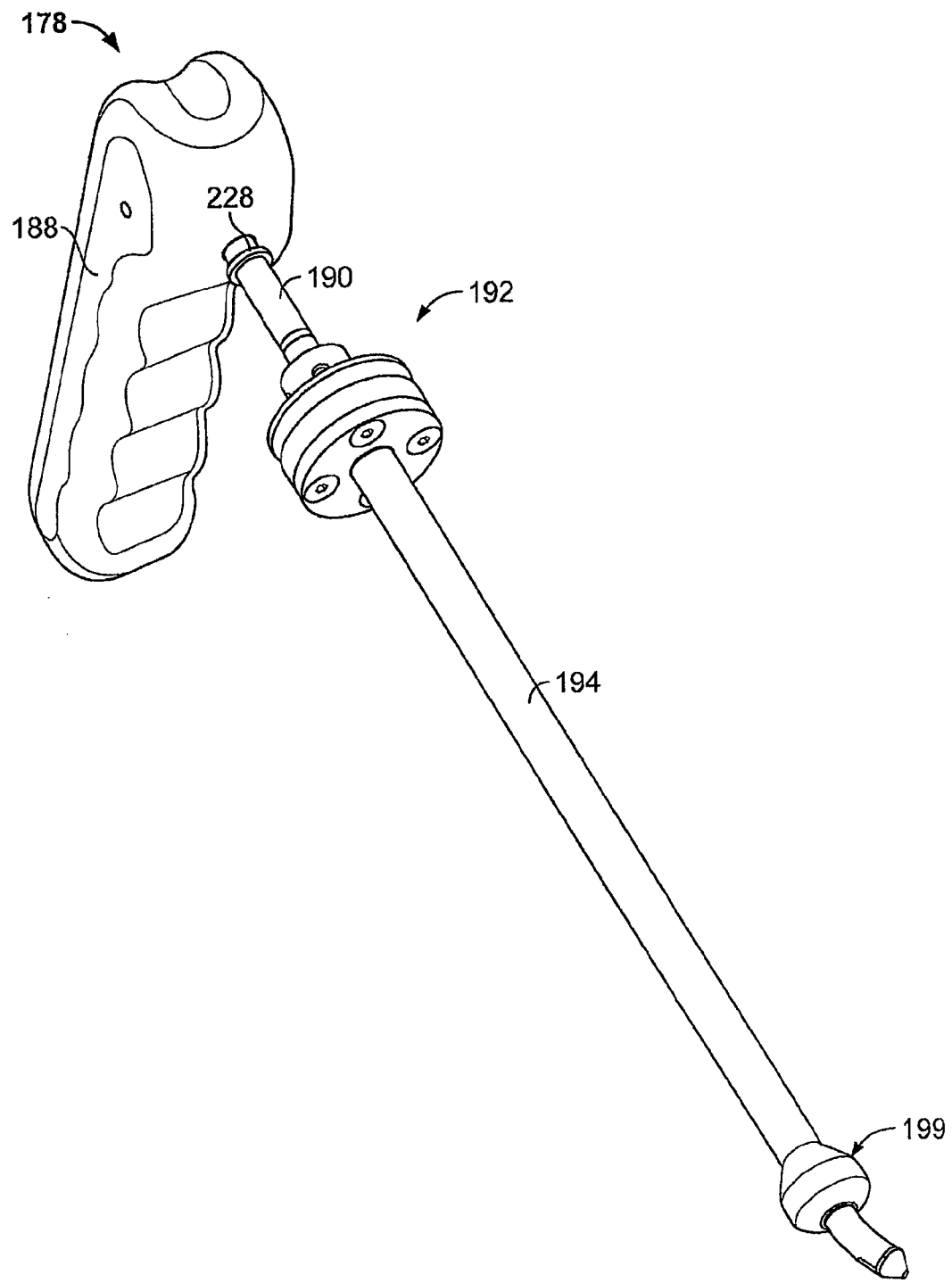
FIG. 20 is a perspective view of the rod inserter of FIG. 17 having the outer sleeve in a first stage and a connecting member mounted thereto.
Figure 21:
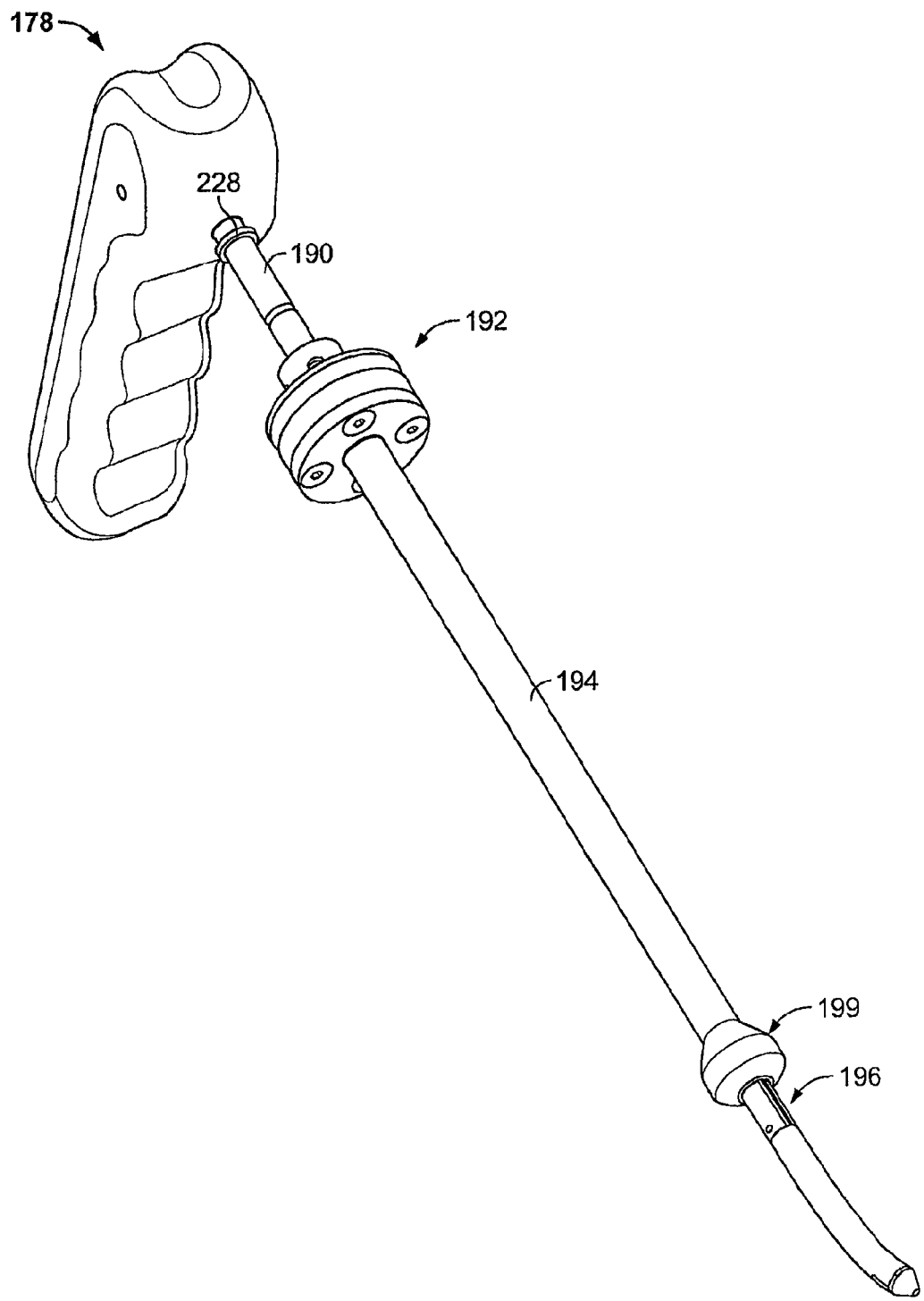
FIG. 21 is a perspective view of the rod inserter of FIG. 17 having the outer sleeve in a second stage and a connecting member mounted thereto.

In another form, illustrated in FIGS. 15 and 16, a guide 160b may have a curved guide body 162b with a curved slot 164b. The curvature of the guide 160b correlates to the curvature of the spine and connecting member 26 to be implanted along the spine. Using the curved guide 160b can facilitate insertion of the connecting member 26 if the connecting member 26 that is implanted is curved. A pair of sliding attachment brackets 168b and 170b, oriented within a slide body 165b, can be secured into position by set nuts 172b, 174b. In addition, the slide body 165b with opening 166b is held into position with set nut 171b To insert the connecting member 26 into the yokes 22, a rod inserter 178 is typically used. The rod inserter may be used in conjunction with the guide 160 and yoke manipulators 98. If desired, a path through the surrounding tissue may be created by first using a muscle splitter to facilitate insertion of the connecting member 26. The features of the connecting member 26 may include a nose portion 180 with a rounded, chamfered, or reduced diameter tip, a body 182 having a round constant diameter, and an attachment end 184. The connecting member 26 may be straight or bent depending on the profile of the patient and the surgeon's preference. The nose 180 is preferably shaped to ease the passage of the connecting member 26 through the soft tissue, the yoke manipulators 98, various other MIS system instrumentation, and into the yoke 22. The attachment end 184 is used to hold the member 26 and steer it into position within the yoke 22. The end 184 may include connecting structure 186 such as a bore, boss, flats, capture, groove, ridge, or other distinct structure that would serve to securely hold the member 26 to the rod inserter 178 during the insertion procedure. As shown in FIG. 2, the attachment end 184 includes a flat surface 183 transverse to the body 182 of the connecting member, and a projection 185. The projection 185 includes the connecting structure 186 shown as a bore, and may also be shaped to limit the movement of the connecting member 26 when it is connected to the rod inserter 178. For example, the projection 185 may be offset from the center of the connecting member 26 or the projection 185 or connecting structure 186 may be a number of different shapes or sizes.

To begin the insertion procedure, the connecting member 26 is secured to the rod inserter 178. The rod inserter 178 functions to hold and guide the connecting member 26 into position within the yoke 22. As shown in FIGS. 17-22, the rod inserter 178 includes a handle 188, an inner shaft 190, a shift assembly 192, and a locking sleeve 194. The inner shaft 190 includes an attachment end 196 that attaches the connecting member 26. The attachment end includes two slots 198. Preferably the prongs 200 flex such that the two prongs can be arranged about a portion of the connecting member 26. Each of the prongs 200 preferably includes connecting structure 202 that securely grips corresponding structure 186 on the connecting member 26. The connecting structure 202 can include a recess or boss 204, shown in FIG. 19 on the inside surface of the prongs 200. This boss 204 can facilitate a secure connection between the connecting member 26 and the rod inserter 178. In addition, the prongs 200 include a flat or shelf 206 to limit the rotational movement of the connecting member 26 during the insertion procedure as described below. This flat 206 can limit the movement by contacting the projection 185 or other structure of the connecting member 26. Opposite the attachment end, the rod inserter includes the handle 188, the handle may be fixed by a fixation pin 195, or threads, compression fit, bonded or otherwise affixed to the inner shaft 190. The handle 188 is typically mounted substantially perpendicular to the inner shaft 190 and is preferably sized and shaped for optimal manual control.

The rod inserter 178 goes through several stages during the insertion procedure. During one stage, the locking sleeve 194 is slid down the inner shaft 190 into the fully extended configuration. The fully extended configuration positions the locking sleeve 194 to surround the inner shaft 190 and the prongs 200. The connecting member 26 is held between the prongs 200 and when the locking sleeve 194 is slid down the inner shaft 190 into the fully extended configuration, the connecting member 26 is secured between the prongs 200. Such an arrangement limits the movement of the connecting member 26 with respect to the rod inserter 178. During a second stage, the locking sleeve 194 is moved to expose the entire connecting member 26 allowing the connecting member 26 to pivot relative to the rod inserter 178. The connecting member 26 remains attached to the rod inserter 178 via the connecting structure 202. The connecting structure 202 keeps the connecting member 26 attached to the rod inserter 178 during the second stage by preventing the prongs 200 from splaying outward away from the connecting member 26. When the prongs 200 splay outward the connecting structure 202 of the rod inserter 178 disengages with the connecting structure 186 of the connecting member 26. Therefore, during a third stage, the locking sleeve 194 is moved to sufficiently expose the slots 198 such that the prongs 200 can splay and disengage with the connecting member 26.

During use of the rod inserter 178, the movement of the locking sleeve 194 is controlled by the shift assembly 192. The shift assembly 192 locks the sleeve 194 into position. To do this, the shift assembly includes a ball and detent mechanism 208 that provides a releasable lock for securing the sleeve 194 into position. The inner shaft 190 includes recesses 210 that engage ball detents 212 in the shift assembly 192. Since there are three stages the rod inserter 178 undergoes during insertion of the connecting member 26, there are three separate locking sleeve 194 positions. In this regard, the inner shaft 190 includes three recesses 210 that engage the detent balls 212 in the shift assembly 192. The position of the recesses 210 correlate to the three locking sleeve 194 positions and to the different insertion stages.

In one embodiment of the shift assembly 192, as shown in FIGS. 17-23, the assembly 192 includes a spring housing 214 with a spring 216, a ball housing 218, and a cover plate 220. The spring housing 214 is located away from the ball housing 218, which is adjacent to the cover plate 220. The spring housing 214 is secured or welded to the locking sleeve 194. The locking sleeve 194 includes radially inward facing angled cutouts 222. The ball detents 212 reside within the angled cutouts 222 and a stepped-opening 224 in the ball housing 214. When the sleeve 194 is secured in one of the three positions, the angled cutouts 222 align with recesses 210 on the inner shaft 190. To move the sleeve 194 from one of the three locked positions, the ball housing 218 and plate 220 are moved toward the spring housing 214. The housings 214 and 218 are biased away from one another by compression spring 216. When the ball housing 218 and plate 220 are moved the ball detents 212 are able to move into the larger aperture of the stepped-opening 224. Having the ball detents 212 in the larger aperture allows the detents 212 to disengage from the recess 210 on the inner shaft 190 such that the inner shaft 190 and the locking sleeve 194 can move relative to one another. The plate 220 bounds the ball detents 212 in the ball housing 218 and the plate 220 is secured to the housing 218 by screws 226. In addition to the recesses 210, the inner shaft 194 may optionally also include a hard stop 228, or the handle 188 may be used as a stop.

During the various stages of rod insertion, the rod inserter 178 and the connecting member 26 have three relative configurations: rigid attachment where the locking sleeve 194 surrounds a substantial portion of the prongs 200 limiting or blocking the pivoting movement of the connecting member 26, pivoting or articulating attachment where the pivot connection between the inner shaft 190 and the connecting member 26 is unblocked and pivoting is permitted, and disengagement from attachment where the locking sleeve 194 is moved up the inner shaft 190 such that the prongs 200 splay away from one another and release from the connecting member 26. To move the locking sleeve 194 from one position to another, a selectively engageable lock, such as the shift assembly 192, may be used to prevent undesired shifting of the locking sleeve 194 from the rigid attachment to the pivoting attachment. When the connecting member is rigidly attached to the rod inserter 178, the locking sleeve 194 covers the pivot connection or the pivot axis is blocked to restrict the pivoting of the spinal rod or connecting member 26 about the pivot axis. When the locking sleeve 194 is moved upward toward the handle 188 and uncovers the pivot connection, the connecting member 26 is free to pivot about the pivot connection. To limit the rotational movement of the connecting member 26 to movement in one direction, a stop may be provided on the inner shaft.

Figure 22:
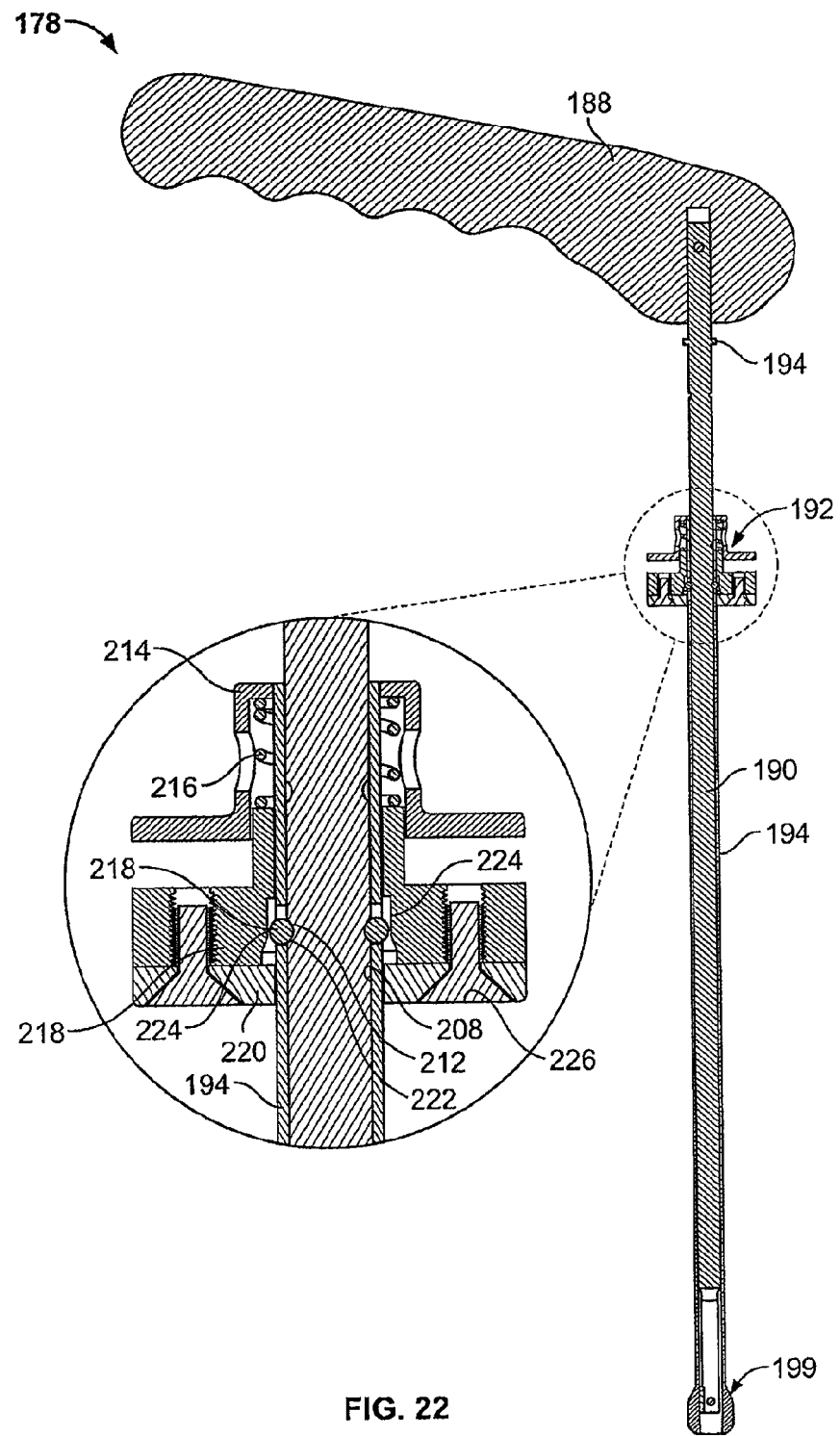
FIG. 22 is a cross-sectional view of the rod inserter of FIG. 17 having the outer sleeve in the first stage of rod insertion.
Figure 23:
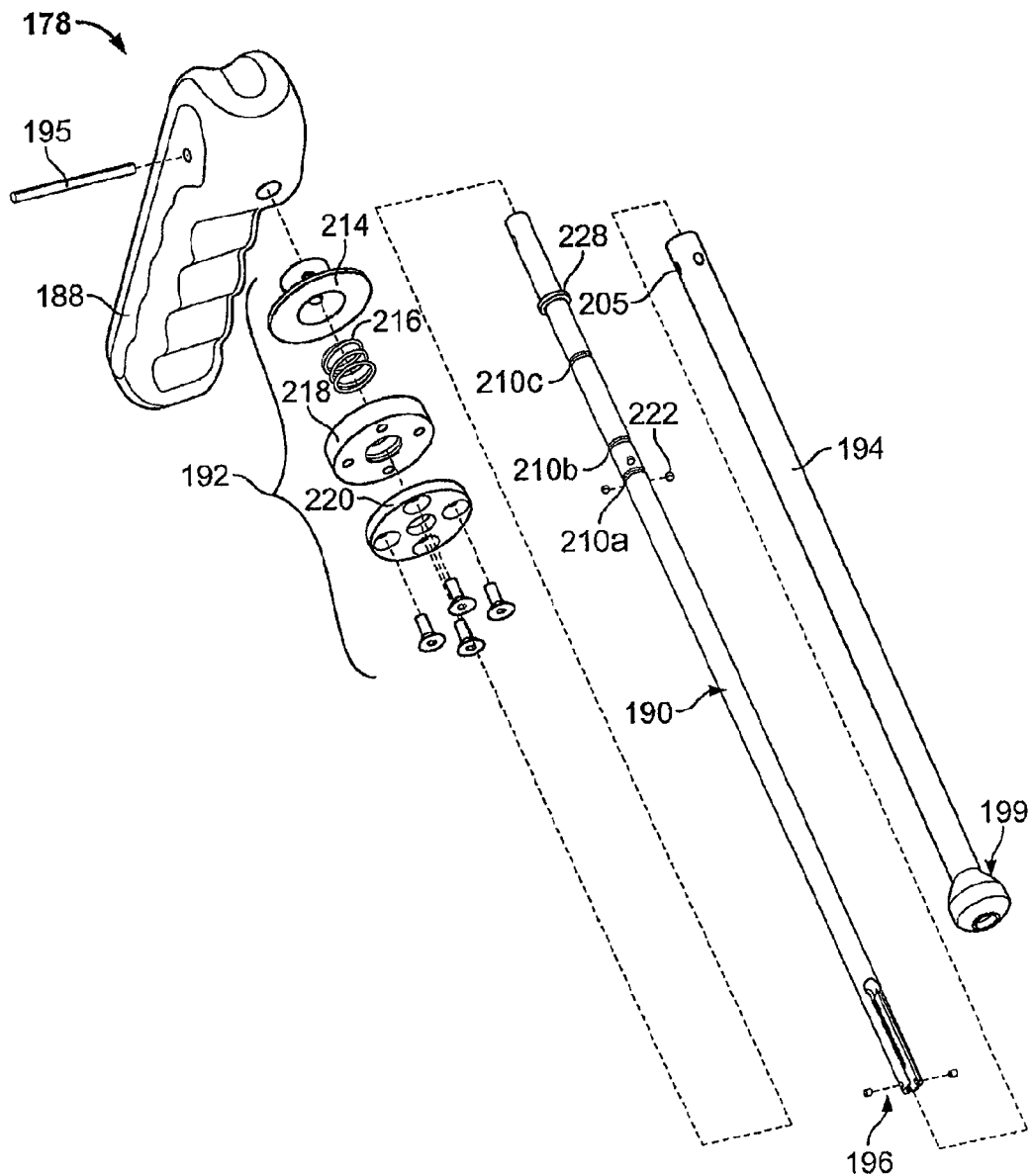
FIG. 23 is an exploded view of the rod inserter of FIG. 17.
Figure 24:
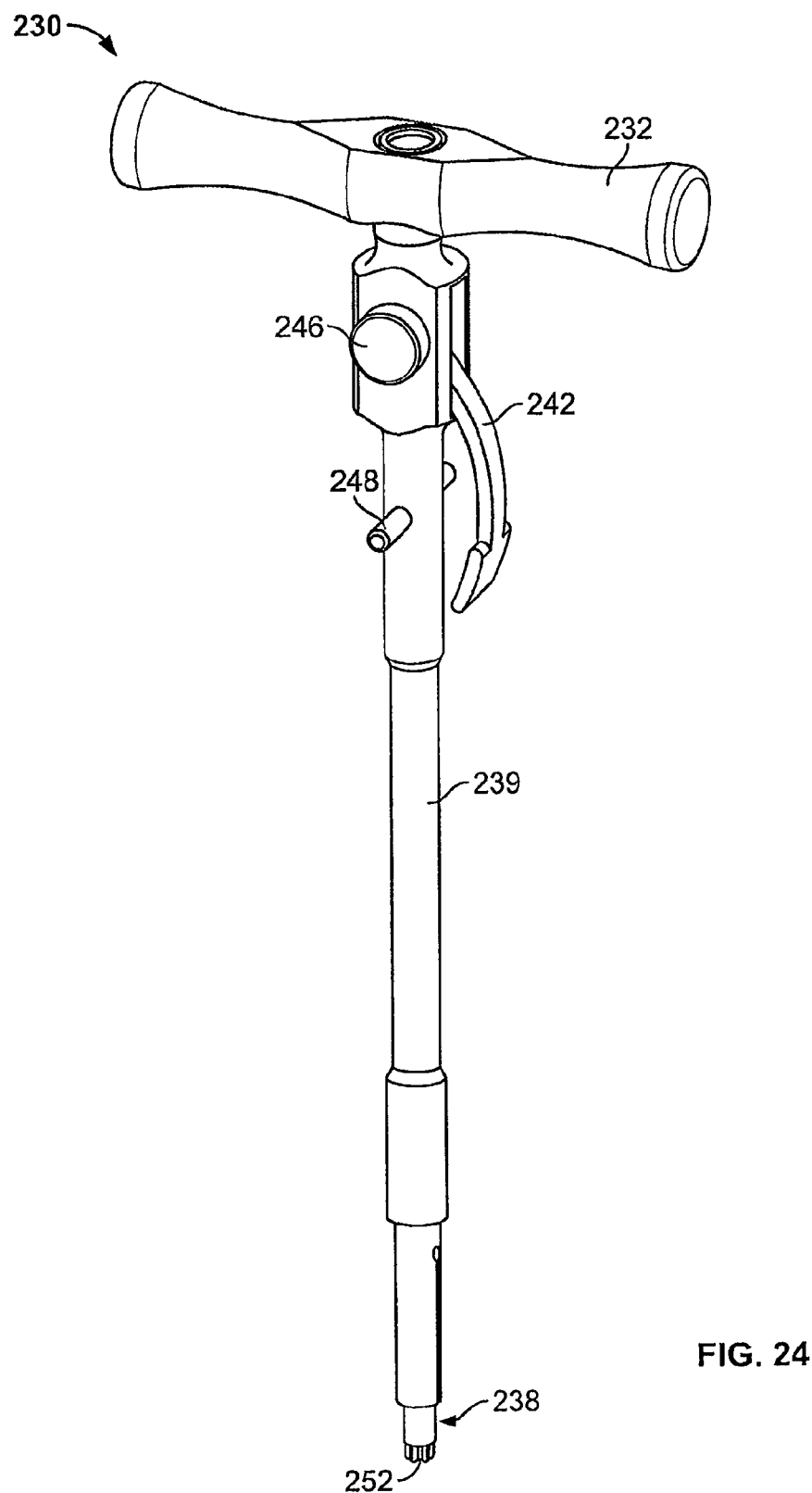
FIG. 24 is a perspective view of a cap inserter having a lever in the lowered position.
Figure 25:
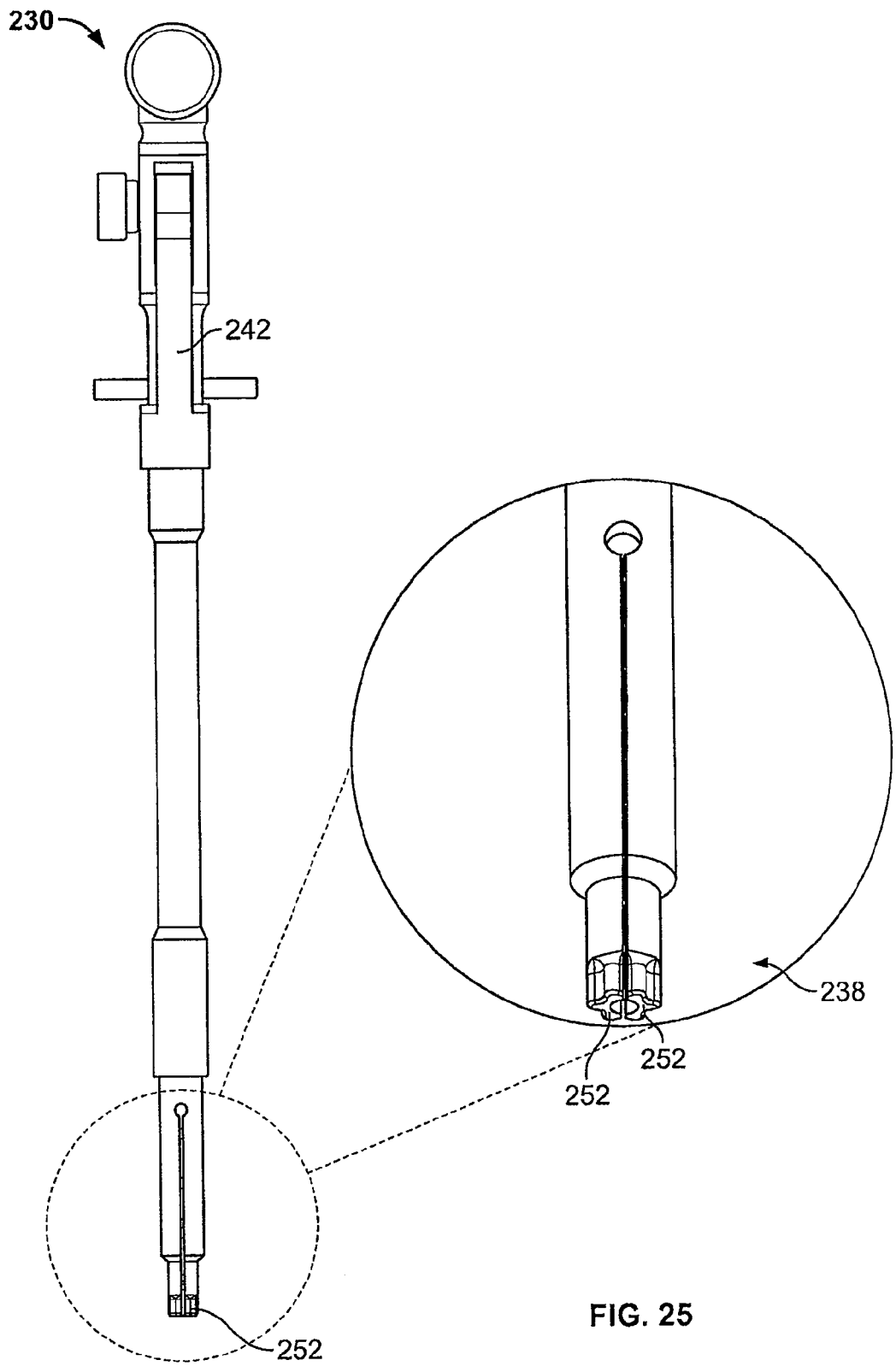
FIG. 25 is a side elevation view of the cap inserter of FIG. 24.

Turning to more of the detail of the shift assembly 192, and more particularly the shift assembly 192 positioning during the rod insertion procedure, the selectively engageable lock includes at least one locking member or detent 212 that is positionable in the aperture 222 of the locking sleeve 194 and one of the recesses 210 at the inner shaft 190. As shown in FIG. 23, the inner shaft 190 has three recesses 210a, 210b, and 210c. The shift assembly 192 as shown in FIG. 22, has an internal slot or stepped-opening 224 facing the locking sleeve 1094, the stepped-opening 224 having a narrow portion and a wide portion with an inclined ramp extending therebetween. When the locking member or detent 212 is positioned in the narrow portion of the stepped-opening 224 adjacent one of the recesses 210, shifting of the locking sleeve 194 is limited or prevented. Depending on which recess 2101a, 210b, 210c, the rod inserter 178 will be secured into a different configuration. When the detent 212 is positioned between the opening 222 of the locking sleeve 194 and the recess 210a, the locking sleeve 194 is positioned such that the pivoting movement of the connecting member 26 is limited or blocked. When the detents 212 are engaging the blocking recess 210a, the locking sleeve 194 is positioned to prevent pivoting. The unblocking recess 210b is located between the blocking recesses 210a and the release recess 210c. When the detents 212 of the shift assembly 192 are positioned in the unblocking recesses 210b, the locking sleeve 194 allows the connecting member 26 to pivot about the pivot connection but not disengage from the rod inserter 178. When the detents 212 are positioned in the release recesses 210c, the prongs 200 splay outwardly allow the connecting member 26 to disengage from the inner shaft 190. To move the shift assembly 192 from one recess 210 to another recess 210, a portion of the shift assembly 192 that is biased toward the pivot axis is moved from the biased position such that the detents 212 previously captured between the narrow portion of the stepped-opening 224 and the recess 210 are able to move into the wide portion of the stepped-opening 224 such that the locking member or detent 212 disengages from the recess 210a, 210b, 210c.

After the connecting member 26 is inserted into the yokes 22, the caps 24 are positioned and pre-locked within the yokes 22. There are a number of ways to seat and pre-lock the caps 24. Seating the caps 24 can vary in difficulty, depending on the patient's spinal structure, the number of caps, and the order with which the caps are seated. In one preferred embodiment, a cap inserter 230 is used to position and pre-lock the cap 24. The cap 24 locks the connecting member 26 into position. The cap 24 can be configured in a number of positions. In one embodiment, the pre-lock configuration rotates the cap 24 such that the cap 24 is within the yoke 22, but the connecting member 26 can be axially moved relative to the yoke 22. In one form, the pre-lock is about 45 degrees of rotation between the cap 24 and the yoke 22. The cap inserter 230 may be limited to 45 degrees of rotation by a set of pins 248 that engage a counter torque tube 352 described herein. The final lock configurations of the cap 24 position the cap 24 within the yoke and prevent the connecting member 26 from moving relative to the yoke 22.

Figure 27:
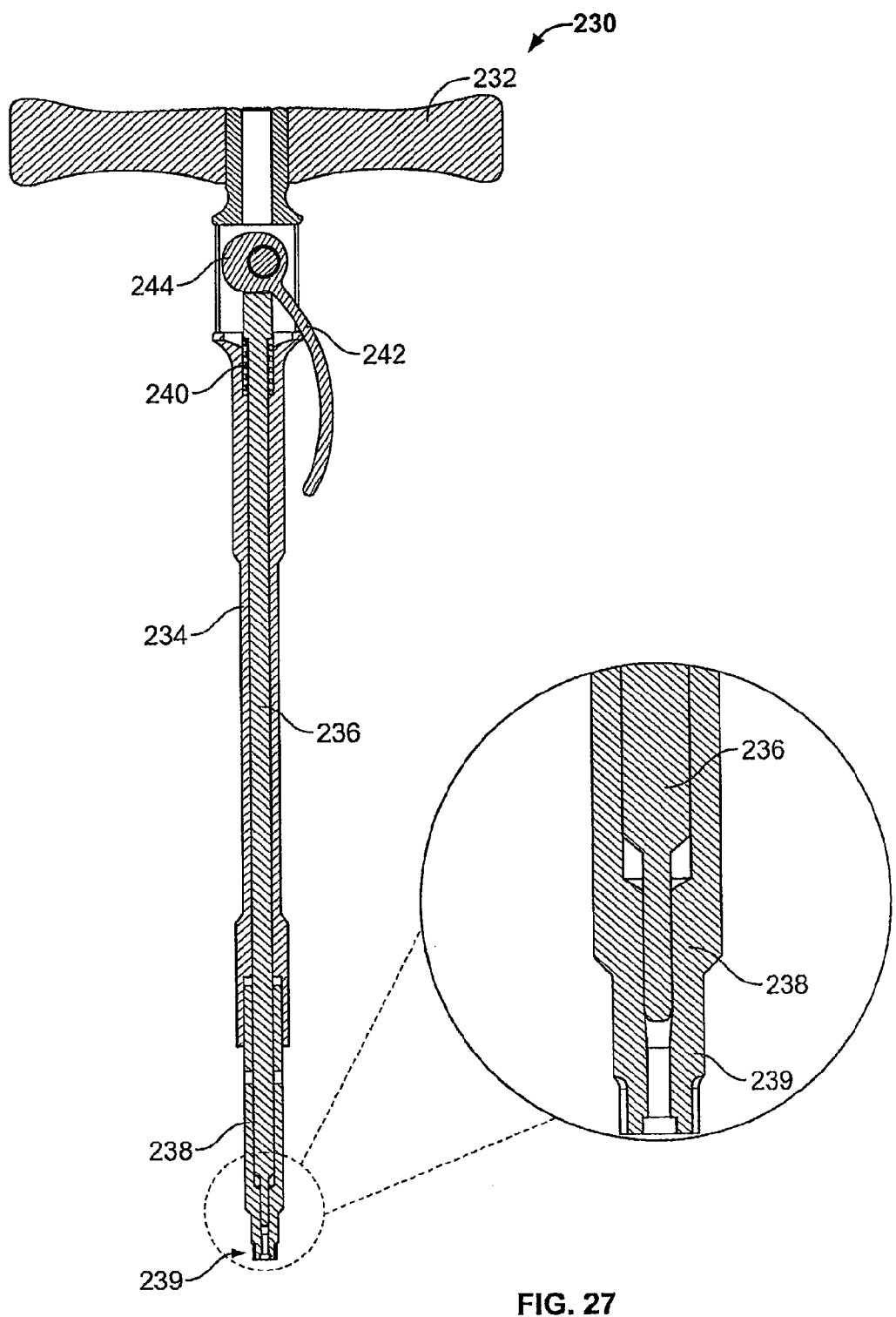
FIG. 27 is a detailed cross-sectional view of the cap inserter of FIG. 24.
Figure 28:
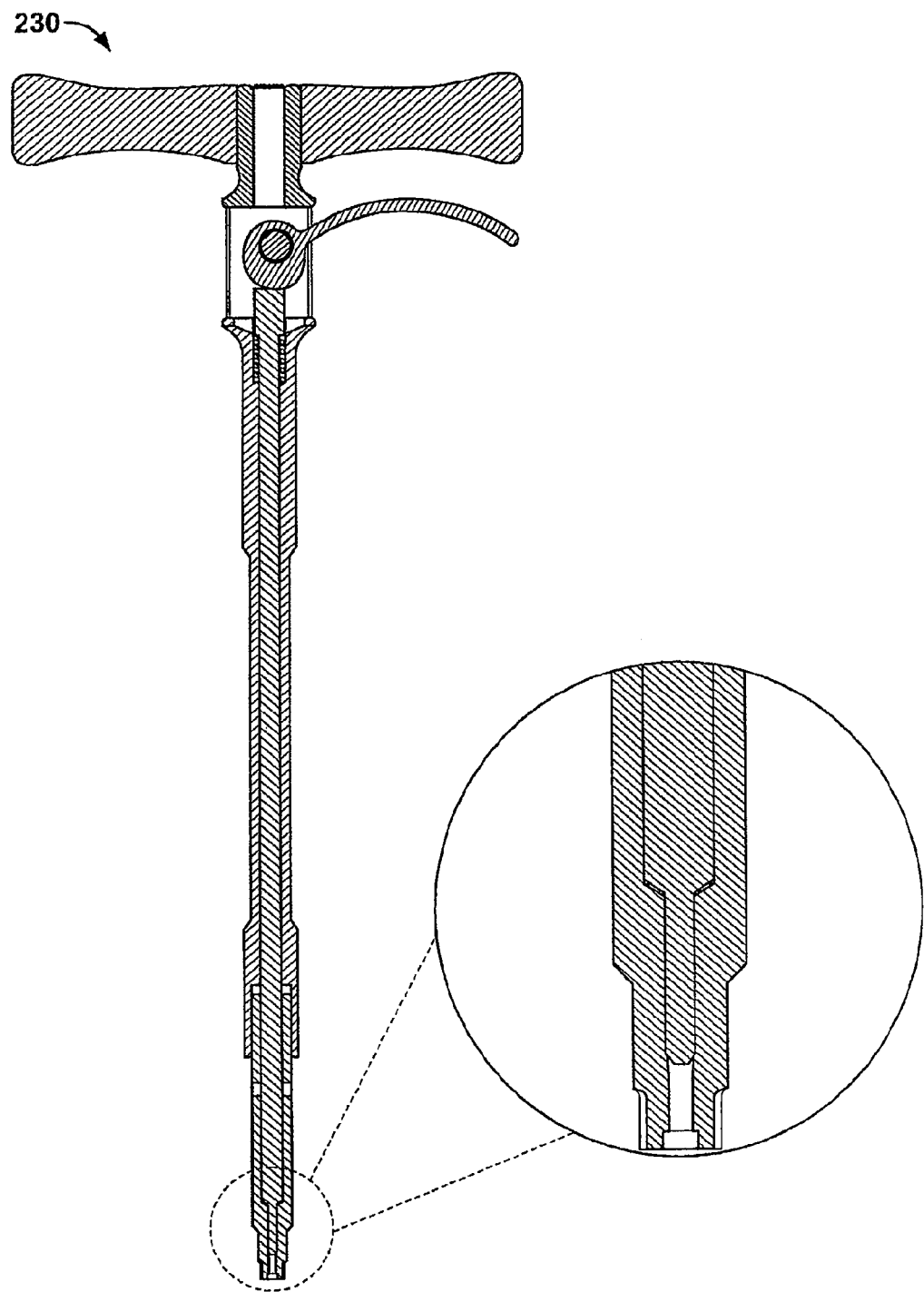
FIG. 28 is a detailed cross-sectional view of the cap inserter of FIG. 24 having the lever in the raised position.
Figure 29:
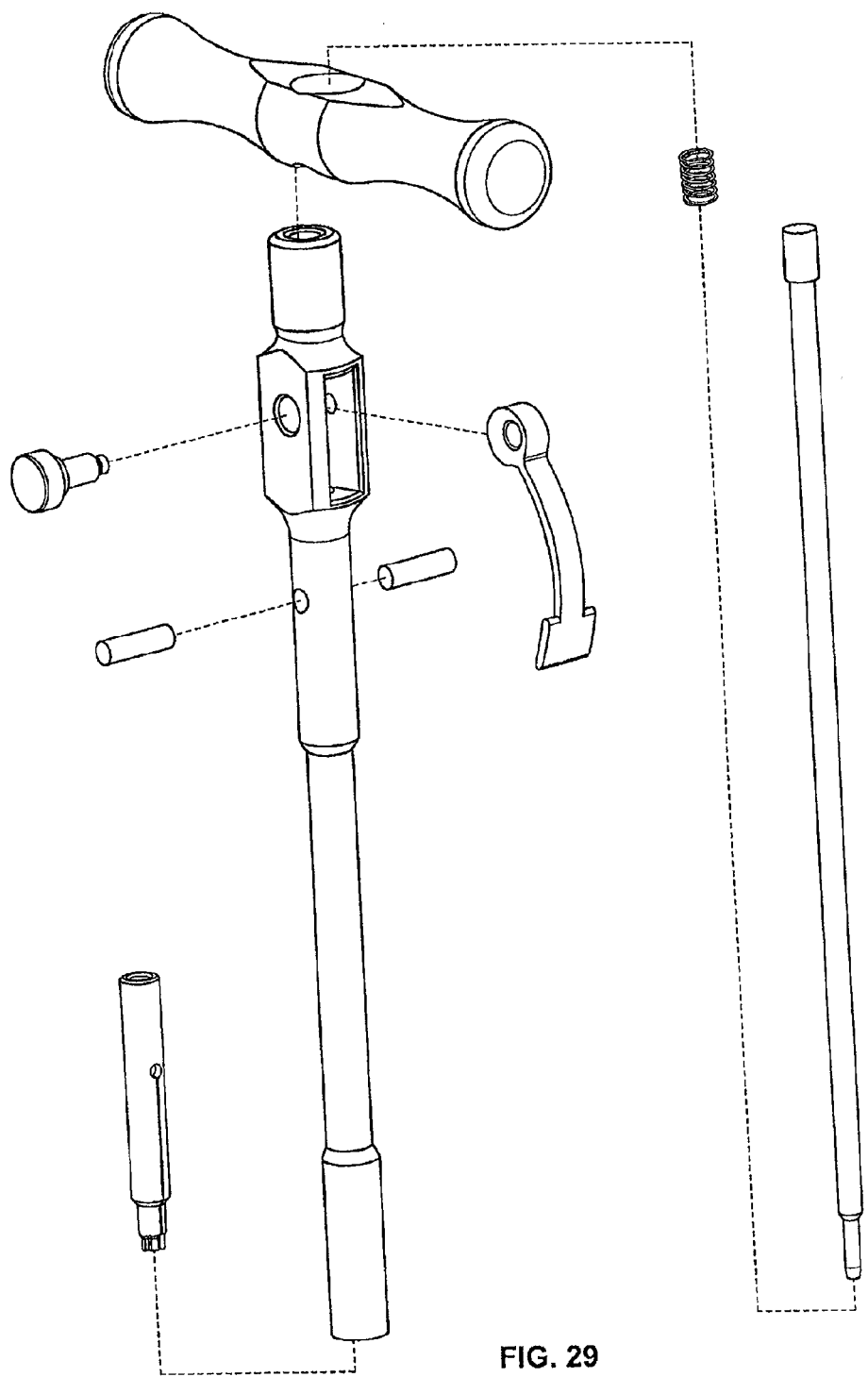
FIG. 29 is an exploded view of the cap inserter of FIG. 24, as configured in accordance with the various embodiments of the invention.
Figure 30:
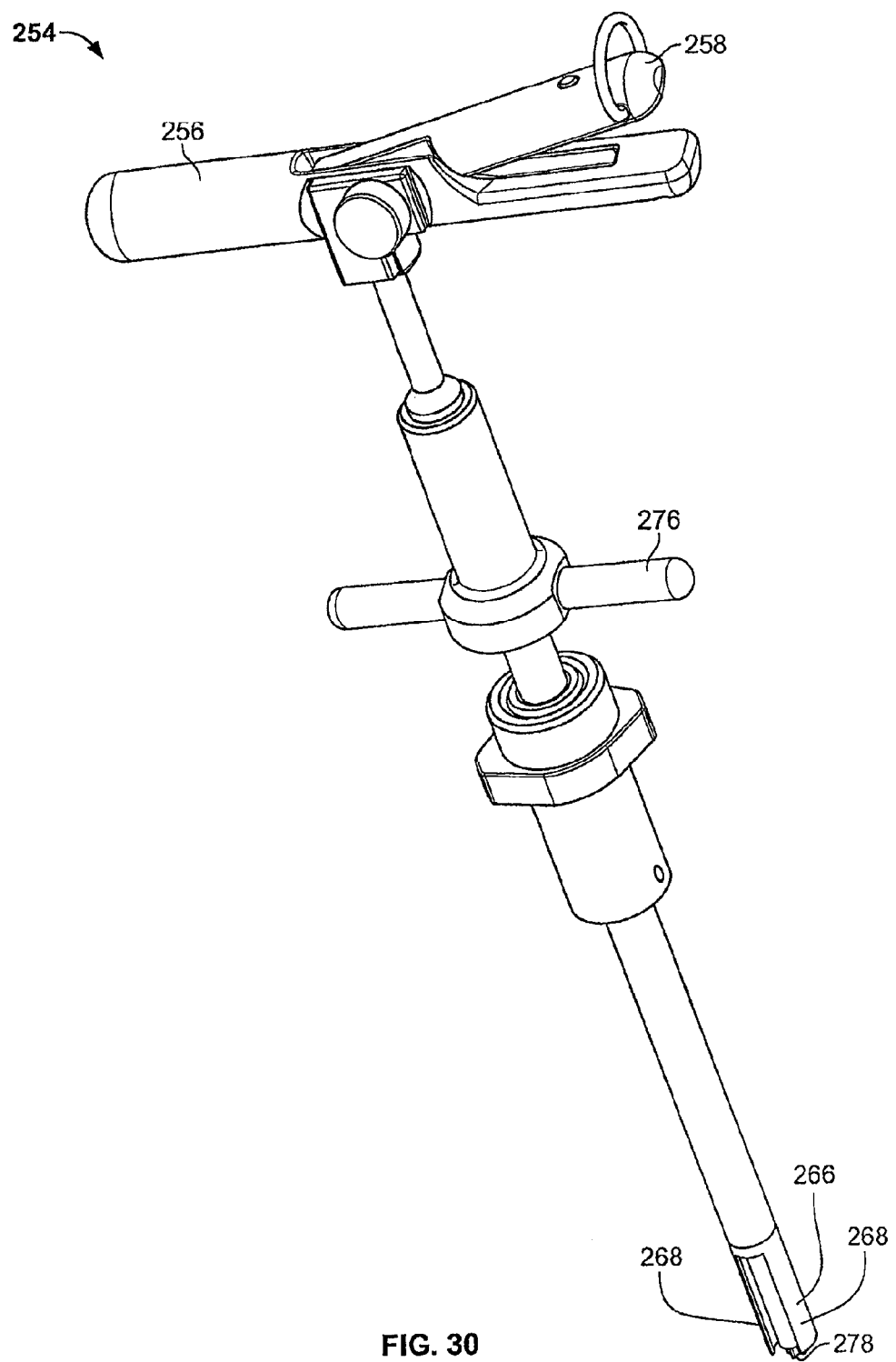
FIG. 30 is a perspective view of a rod persuader.

The cap inserter 230 includes a handle 232, a shaft body 234, cap inserter rod 236, shaft tip 238, spring 240, lever 242 with camming mechanism 244, thumb screw 246 and grip rods 248. As shown in FIG. 27, the cap inserter rod 236 is housed within the shaft body 234 and the shaft tip 238 is attached to an end of the shaft body 234. The spring 240 biases the inserter rod 236 to an upward position. When the lever 242 is rotated up, the camming mechanism 244 pushes the cap inserter rod 236 down such that an end 239 of the shaft tip 238 is splayed outward. The shaft tip 238 includes split star portions 252. The star shape prevents the cap inserter 230 from rotating relative to the cap 24. Thus, when the cap inserter 230 and the cap 24 are engaged with one another, the movement of the cap inserter 230 is transferred to the cap 24. When the inserter rod 236 splays the split star portions 252, the shaft tip 238 engages a star portion of the cap 24. Therefore, the cap 24 is secured to the cap inserter 230. The cap inserter 230 with the secured cap 24 is fed down the manipulator 98. After the cap 24 is positioned within the yoke 22, the cap inserter 230 is rotated 45 degrees to position the cap 24 in the pre-lock position.

The cap inserter 230 can be disassembled for cleaning. To assemble the inserter 230, the spring 240 is placed around the inserter rod 236 and the inserter rod 236 is fed down the shaft body 234. The shaft tip 239 is press fit, threadingly connected, welded, or otherwise attached to the shaft body 234. The lever 242 is secured into position by the thumb screw 246, which is positioned within an opening within the lever 242. The thumb screw 246 may be threaded or otherwise connected to the shaft body 234.

In another form, a rod persuader 254 can be used to position and pre-lock the cap 24. The persuader is typically used to attach subsequent caps 24 to the respective yokes 22 and seat the connecting member 26 after the initial cap 24 has been positioned. The rod persuader 254 includes an upper handle 256 with a lever 258, and a draw shaft 260 inside a drive shaft 262, both of which are inside a cannula 264 and an outer sleeve 266. The rod persuader 254 is operated in a number of steps.

Figure 31:
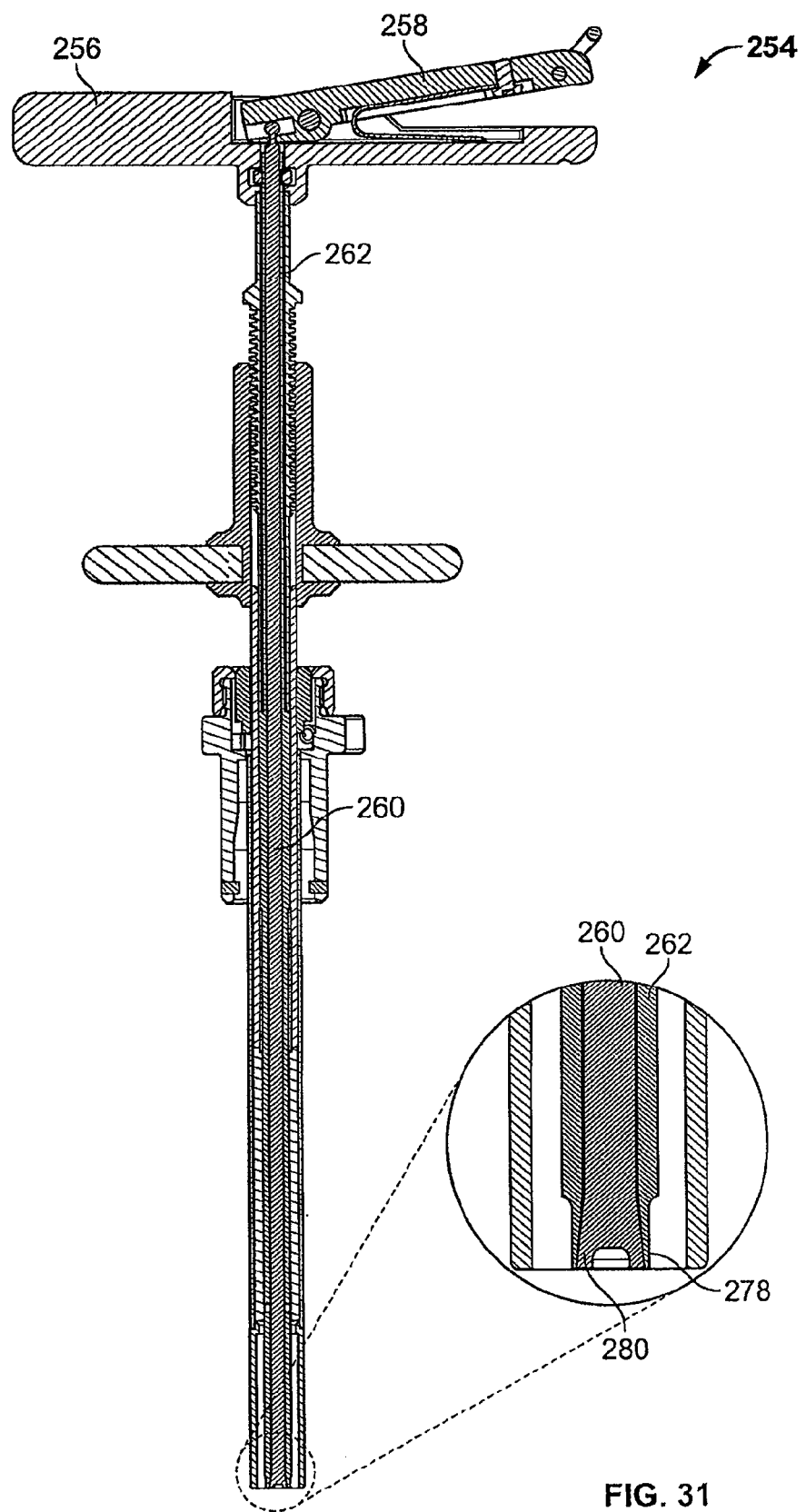
FIG. 31 is a detailed cross-sectional view of the rod persuader of FIG. 30 having a lever raised.
Figure 32:
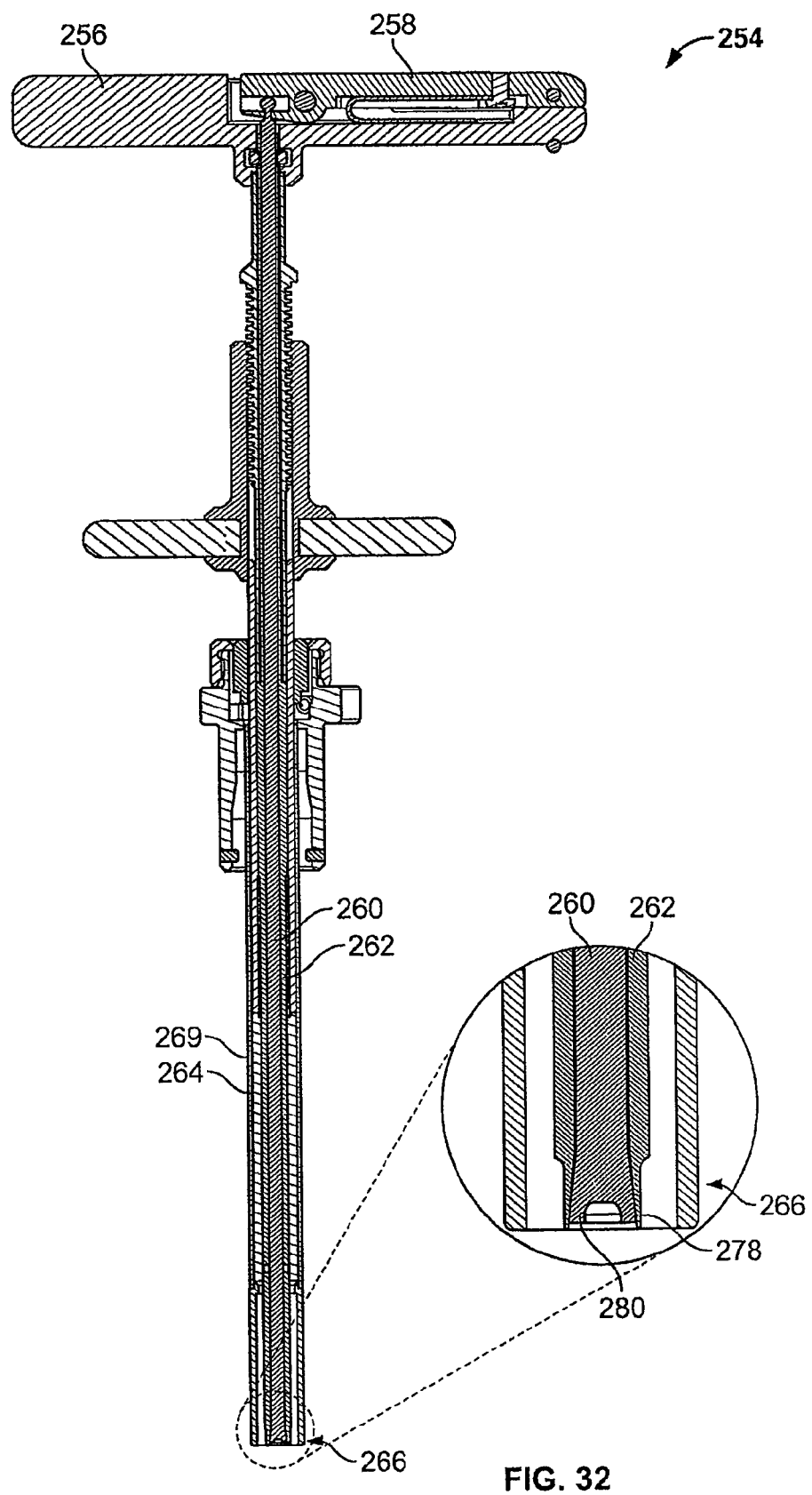
FIG. 32 is a detailed cross-sectional view of the rod persuader of FIG. 30 having the lever lowered and locked, as configured in accordance with the various embodiments of the invention.

First, the drive shaft 262 is fully extended, such that a portion of the drive shaft 262 is extended from a tip of the outer sleeve 266 of the cannula 264 so that the cap 24 can be attached to the rod persuader 254. The tip of the outer sleeve 266 is comprised of two prongs 268. The drive shaft 262 is driven downward by rotating the upper handle 256. As can be seen in the cross-sectional FIGS. 31-33, by rotating the upper handle 256, a plurality of threads 270 on a sleeve 262' located around the drive shaft 262 engage threads 272 on the drive assembly 274. The drive assembly 274 includes the lower handle 276.

After the drive shaft 262 is extended, the cap 24 must be attached to the rod persuader 254. Therefore, with the drive shaft 262 in the extended position, a star tip 278 of the drive shaft 262 can be splayed to engage the cap 24. The draw shaft 260, inside the drive shaft 262, has an expanded end 280 opposite a joint end 282. By raising the draw shaft 260, the two portions of the star tip 278 are splayed when the sloped inner surface of the drive shaft 262 is forced outward by the expanded end 280. The joint end 282 includes a ball 290 and a reduced diameter portion 292. To move the draw shaft 260, the lever 258 is lowered. The lever 258 is secured into the lowered position by rotating a ring lock 284 down around upper handle 256. The joint 282 pivots about the thumb screw 288 such that when the lever 258 is lowered, the joint end 282 raises to pull the draw shaft 262 upward. The lever 258 is biased to the raised position by a leaf spring 286.

Figure 33:
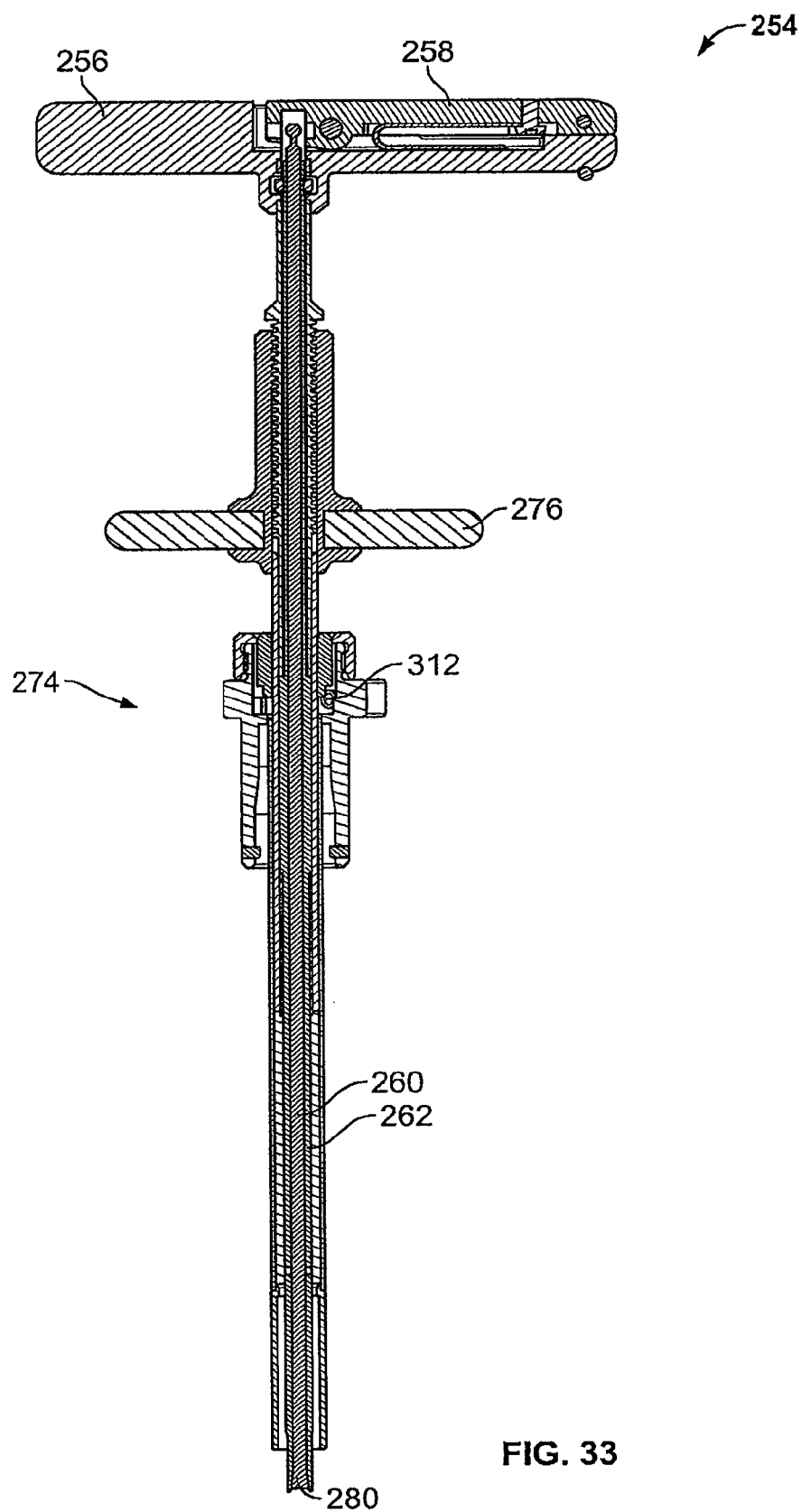
FIG. 33 is a cross-sectional view of the rod persuader of FIG. 30 having a drive shaft and a draw shaft in an extended position, as configured in accordance with the various embodiments of the invention.

The thumb screw 288 also attaches the lever 258 to the upper handle 256. The thumb screw 288 passes through an opening 294 in a plate 296. The plate 296 fits in an angled cut-out in the handle 256. When assembled, the thumb screw 288 also passes through openings 298, 300 and an opening 302 in the lever 258. The plate 296 includes a projection 304 that passes through an opening 306 in handle 256 and engages a reduced diameter portion 308 of the drive shaft 262. By engaging the reduced diameter portion, the movement of the handle 256 translates to the drive shaft 262. As shown in FIG. 33, the drive shaft 262 can be rotated down such that the tip 278 is exposed at the end of the cannula 264. The rotation of the drive shaft 262 is limited by a shelf 310 located on the outer sleeve 265 that engages the drive assembly 274.

After the cap 24 is attached to the persuader 254, the persuader 254 is advanced down the manipulator 98. The cap 24 is sometimes backed up into the tips 266, by rotation of the upper handle 256, for insertion into the manipulator 98. The upper handle 256 is rotated until the cap 24 is within the yoke 24. Then, the lower handle 276 can be rotated 45 degrees to move the cap into the pre-lock position. Rotating the lower handle 276 rotates the drive shaft 262 and star tip 278. In addition, after the upper handle 256 has been rotated such that the threads 270 and 272 are completely engaged, continuing to rotate the upper handle 256 may also produce the required rotation of the drive shaft 262.

Figure 34:
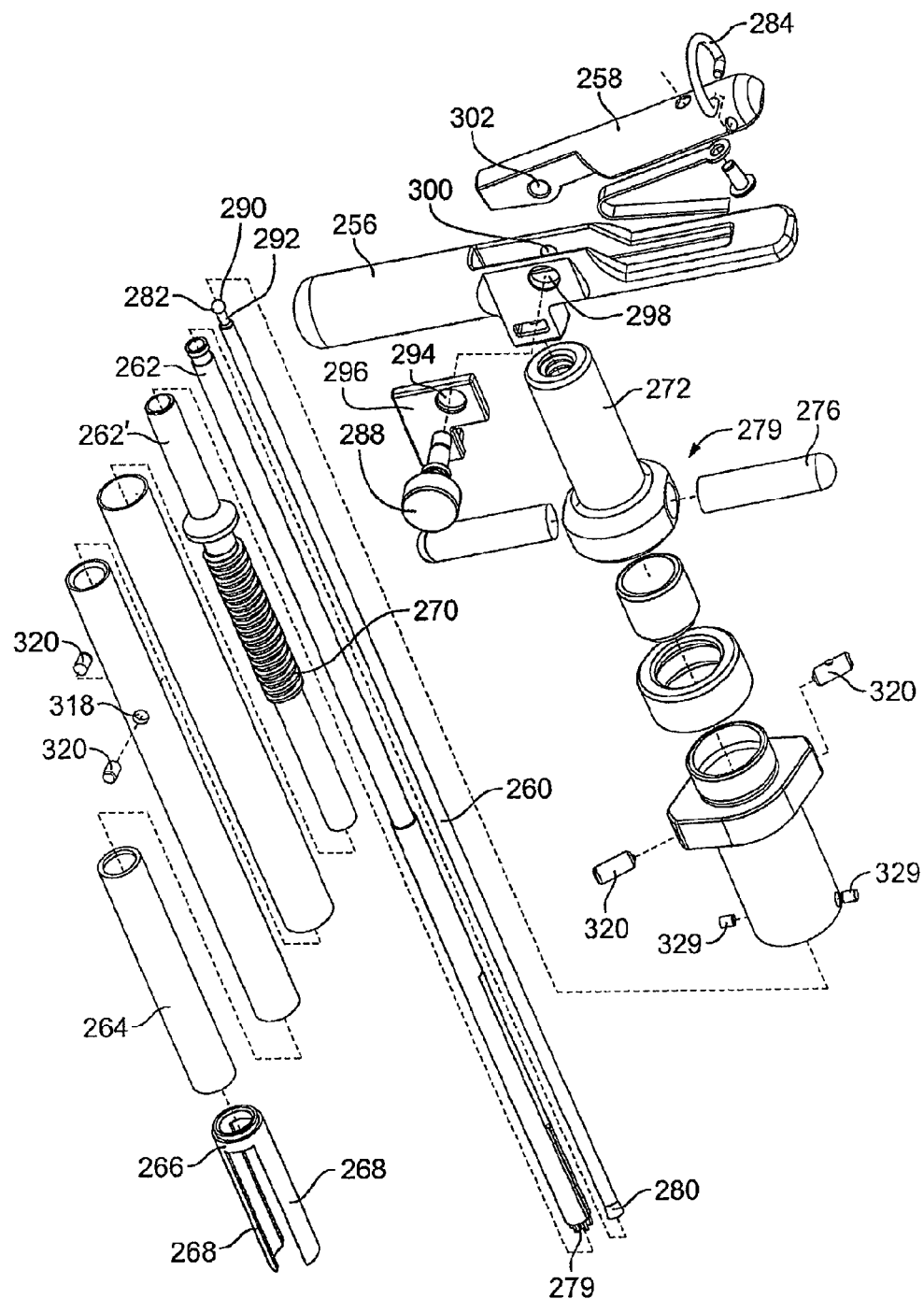
FIG. 34 is an exploded view of the rod persuader of FIG. 28, as configured in accordance with the various embodiments of the invention.
Figure 35:
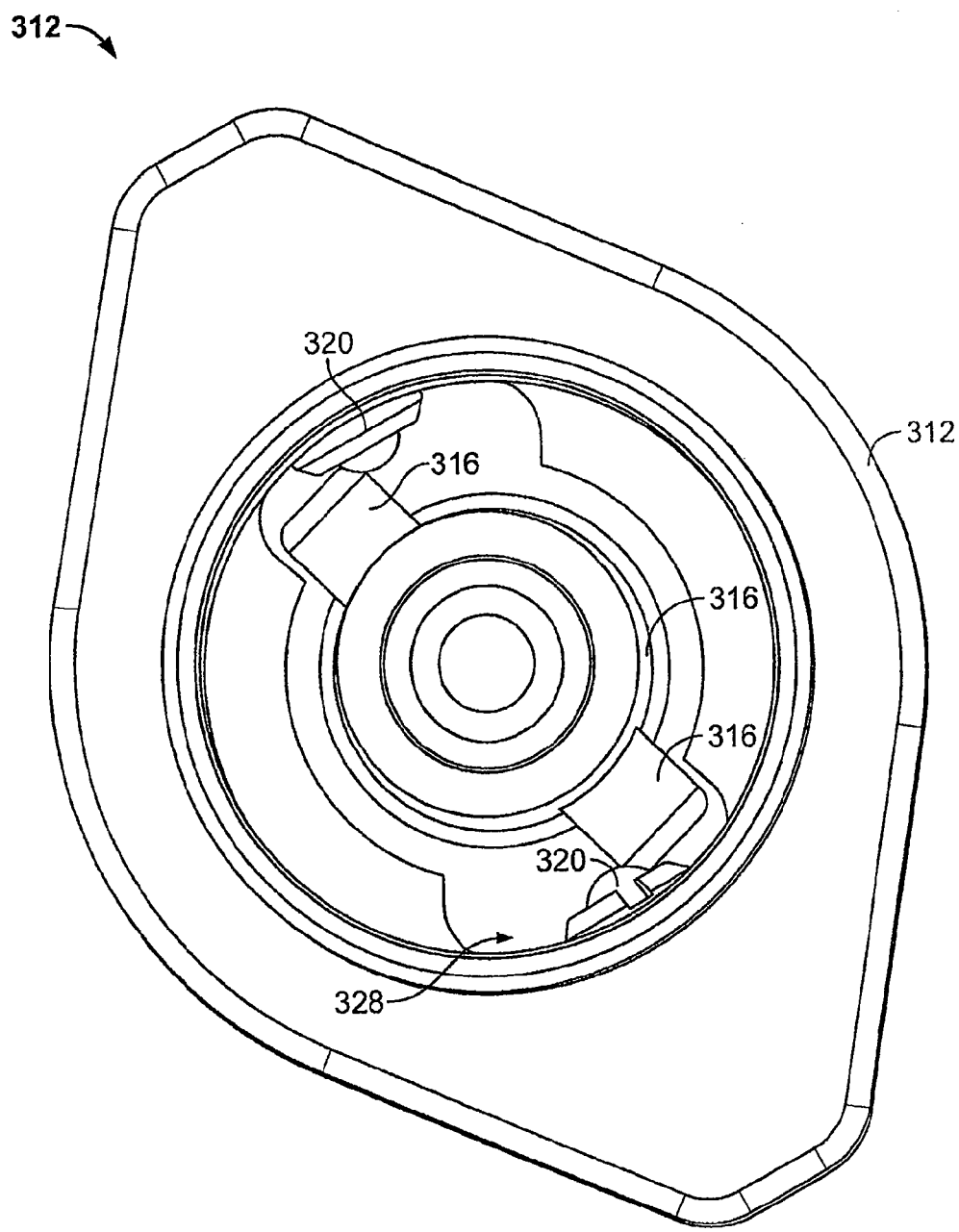
FIG. 35 is an enlarged view of a portion of the rod persuader of FIG. 30 taken along line 35 of FIG. 31, as configured in accordance with the various embodiments of the invention.

The rod persuader 254 includes structure to help rotate the cap 24 to the 45 degrees pre-lock position. Below the drive assembly 274, the persuader 254 includes a ball and detent mechanism 312 for walking the cap 24 into the yoke 22. The ball and detent mechanism 312 is located in housing 314 and is secured relative to the lower handle 276. A drive tube 316 surrounds a portion of the drive shaft 262. The drive tube 316 includes openings 318 that house at least one pin 320 that engage at least one plunger 322 located within openings 324 in the housing 314. The housing 314 also includes an aperture 326 with a groove 328 within which the pins 320 can move until abutting internal walls thereof, which function as a stop. As stated above, rotating either handle 256, 276 can rotate the star tip 278 and also rotates drive tube 316 and the pins 320. The ball and detent mechanism 312 provides the surgeon with tactile feedback such that the surgeon can feel when the drive tube 316 and the star tip 278 have been rotated 45 degrees. As suggested earlier, 45 degrees may be the pre-lock position for the caps 24. The housing 314 also includes a set of pins 329 that can mate with the yoke manipulators 98 connecting structure, shown as a bayonet connection in FIG. 34.

After the cap 24 is configured in the pre-lock position, the cap 24 is released from the persuader 254 by disengaging the ring lock 284 such that lever 258 raises and thus, the star tip 278 disengages from the cap 24. Then, the rod persuader 254 may be removed from the system.

Figure 36:
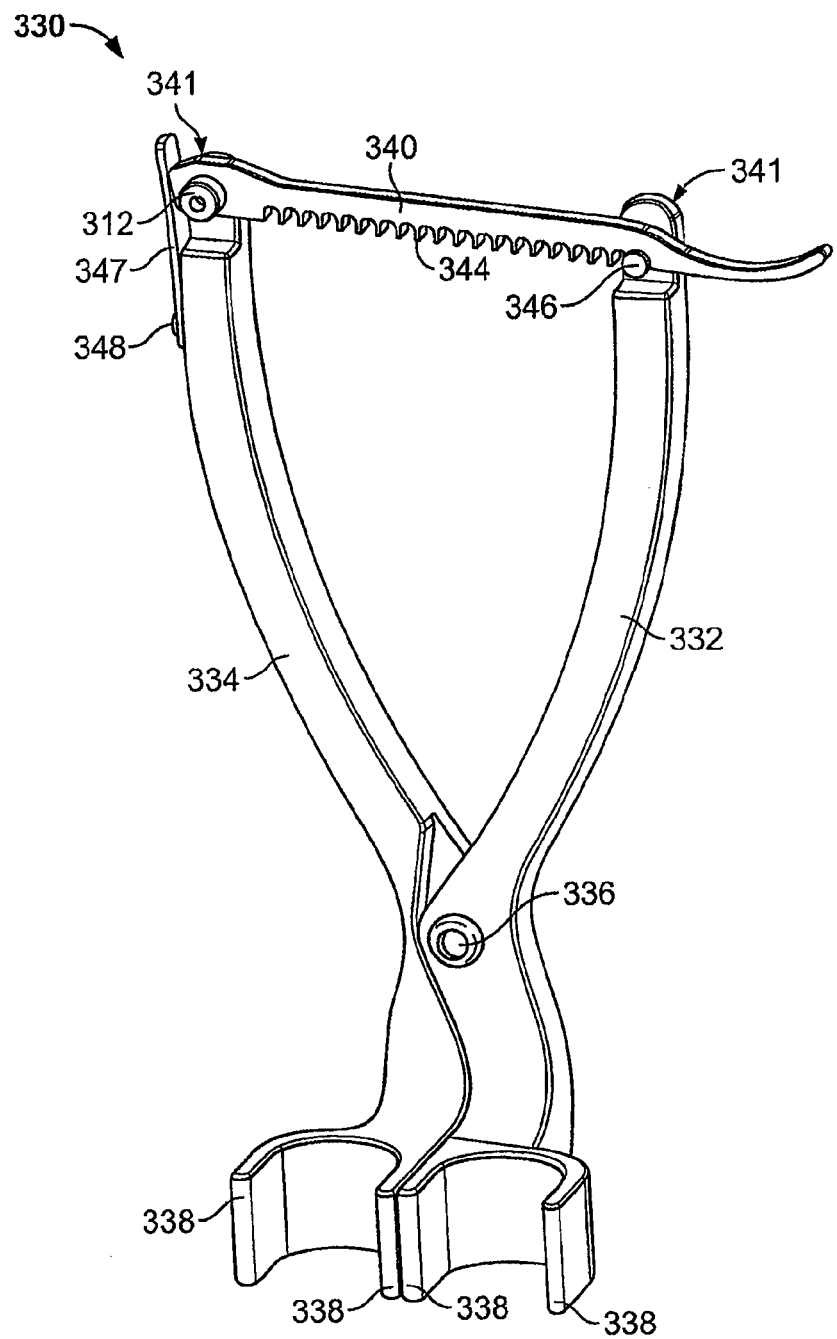
FIG. 36 is a perspective view of a compression-distraction tool, as configured in accordance with the various embodiments of the invention.

Before the caps 24 are moved to the final-lock position, a compression-distraction tool 330 can be used to adjust the distance between the vertebrae. Before the compression-distraction tool 330 is employed, the surgeon may wish to slide a counter torque tube 352 down the yoke manipulators 98 to facilitate a more secure engagement between the compression-distraction tool 330 and the bone anchors 20. As shown in FIG. 36, the compression-distraction tool 330 includes two handles 332, 334, pivotally connected together by a screw 336. Each of the handles has a set of engagement arms 338 that are placed around the counter torque tube 352 or yoke manipulators 98. The engagement arms 338 have flat surfaces that engage the flats 376 on the counter torque tube 352. Opposite the engagement arms 338, a ratchet end 341 of the compression-distraction tool 330 includes a rack member 340 that is pivotally attached to one handle by a screw 342. The rack member 340 includes spaced teeth 344 that engage a projection or latch pin 346 on the handle without the screw 342. The compression-distraction tool 330 further includes a spring 347 attached to one handle by a screw 348. The surgeon can slide the engagement arms 338 around the counter torque tube 352 or the yoke manipulators 98. The surgeon can move the handles 332, 334 apart thereby bringing the counter torque tubes 352 closer together or the handles 332, 334 can be spread farther apart, thereby moving the counter torque tube 352 closer together. By moving the yoke manipulators 98, the vertebras are moved closer or farther apart. Such movement is facilitated by having the pivot point of the compression—distraction tool 330 correlate with the radius of curvature of the connecting member 26.

After the final position of the bone anchors 20 are set with respect to the connecting member 24, the caps 24 may be moved to the final-lock position. A number of tools are available to set the caps 24 in the final-lock position. In one embodiment, the final-lock configuration for the cap 24 is generally just over 100 degrees in total. Therefore, the second stage of the locking rotates the cap 24 an additional 55 degrees from the pre-lock position. A final locker 350 is often used along with a counter torque tube 352. The counter torque tube 352 has connecting structure 378 that limits how much the final locker 350 can rotate. The dowels 366 of the final locker 350 can move within the connecting structure 378, but the structure 378 functions as a stop to prevent over-rotation and over-tightening of the cap 24. However, the rod persuader 254 or cap inserter 230 may also be used.

Figure 37:
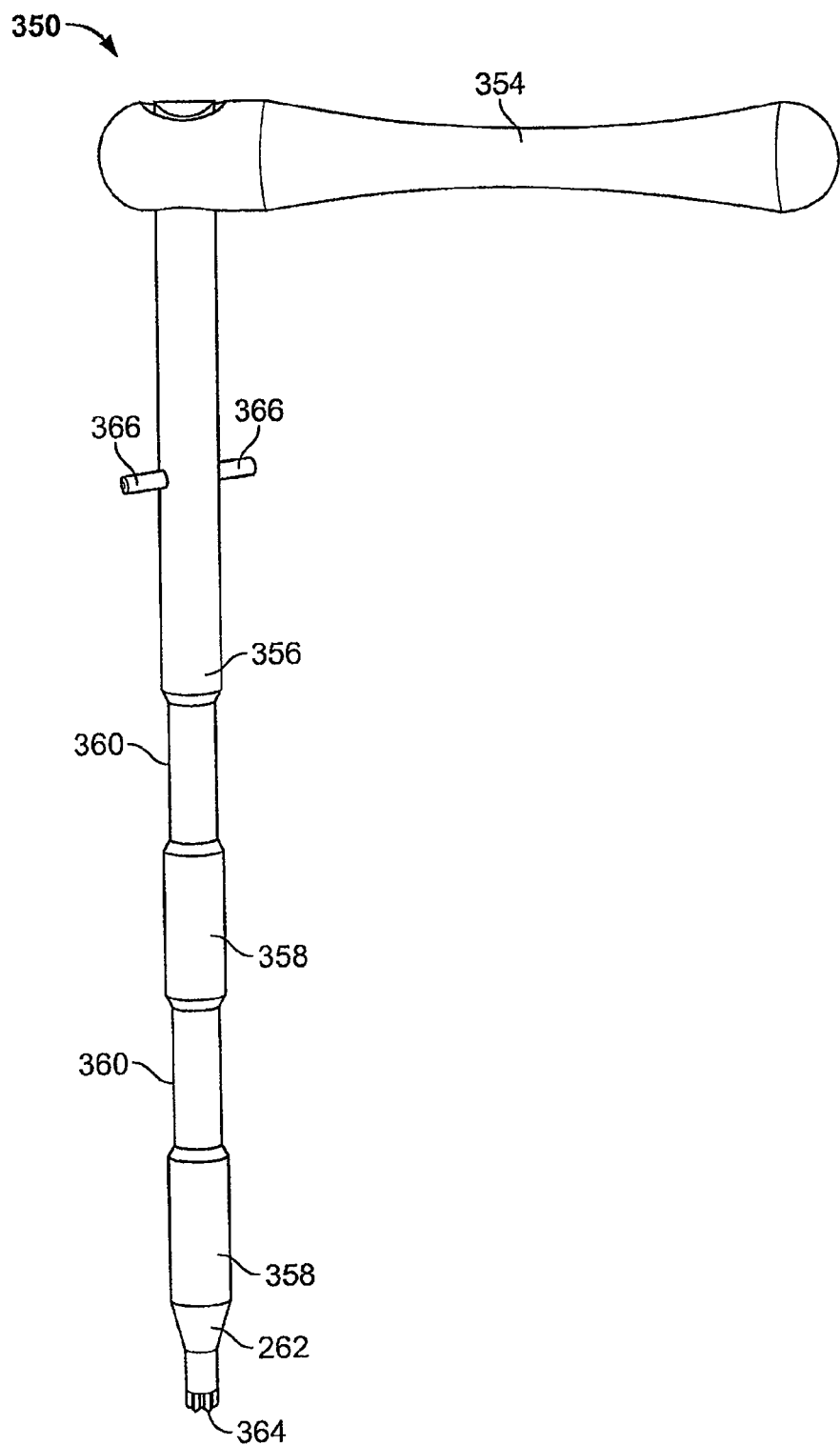
FIG. 37 is a front elevation view of a final locking instrument, as configured in accordance with the various embodiments of the invention.
Figure 38:
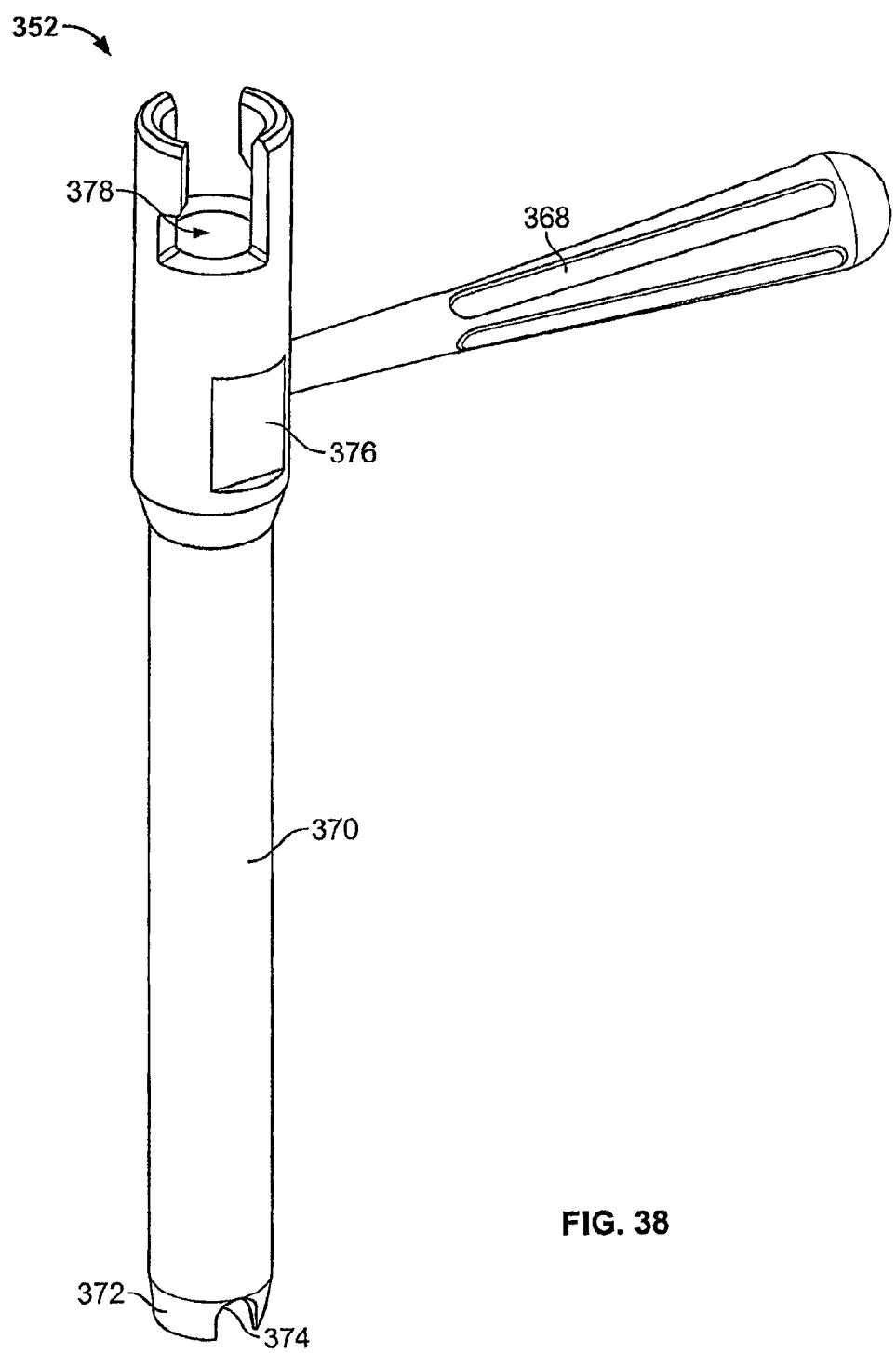
FIG. 38 is a perspective view of a counter torque tube, as configured in accordance with the various embodiments of the invention.
Figure 39:
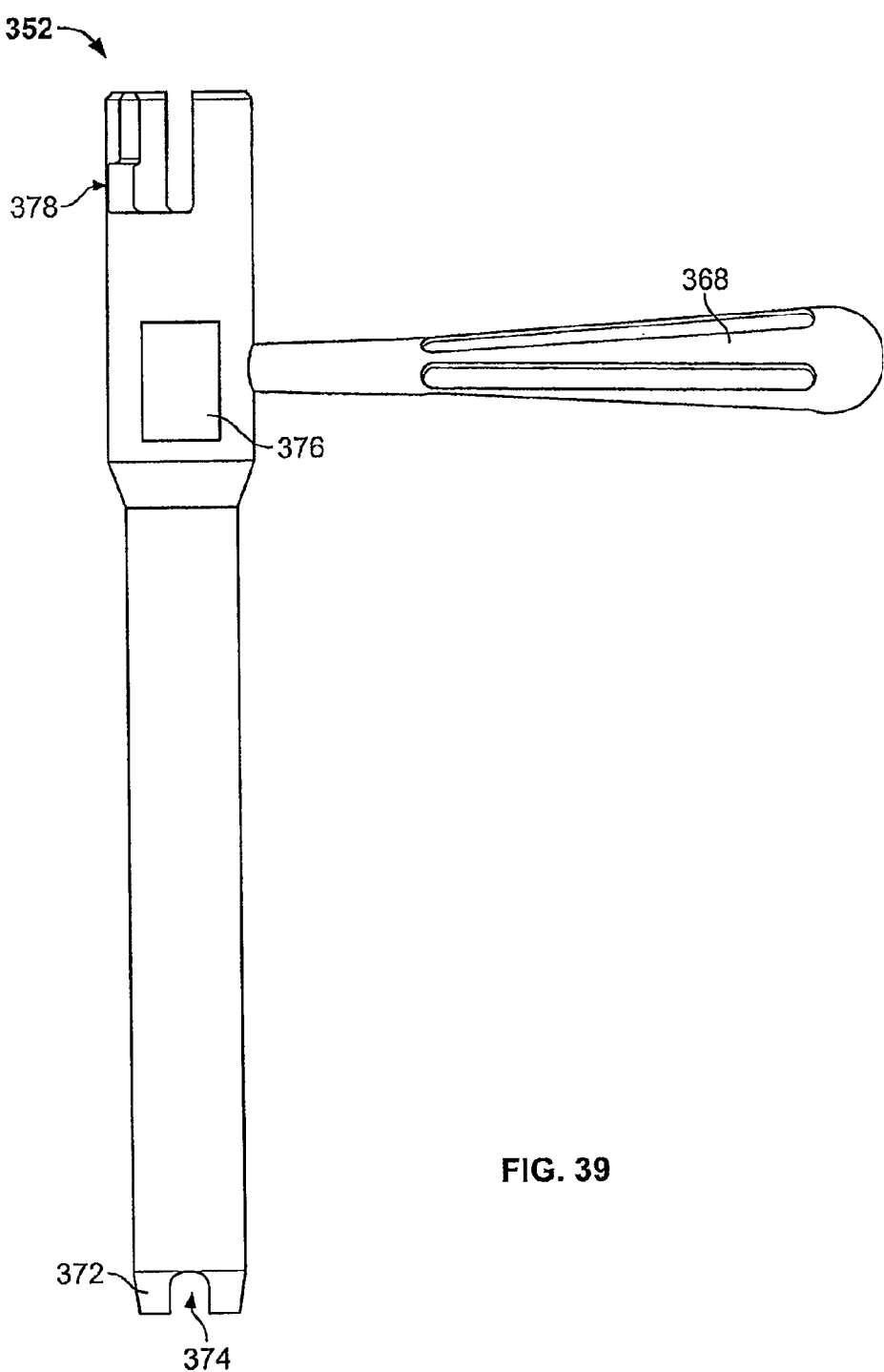
FIG. 39 is a side elevation view of the counter torque tube of FIG. 38, as configured in accordance with the various embodiments of the invention.

As shown in FIG. 37, the final locker 350 includes a handle 354, a shaft 356, centering portions 358, cutout portions 360, tapered portions 362, and an engagement end 364. The engagement end 364 is sized to fit within the cap 24 and engage the star shape to rotate the cap 24 into the final-lock position. The final locker 350 also includes pins 366. The centering portions 358 help guide the final locker 350 into the cap 24, while the cutout portions 360 limit the amount of friction experience between the final locker 350 and the counter torque tube 352. To ensure that the cap 24 can be rotated without the yoke 22 also rotating, the counter torque tube 352 can be placed within the docking port 64. The counter torque tube 352 includes a handle 368, a sleeve 370, tapered portion 372, curved cutouts 374, flats 376, and connecting structure 378. In addition, the counter torque tube 352 includes dowel pins 380 located on the inside of the sleeve 370. The dowel pins 380 can be used to orient the counter torque tube 352 with the yoke manipulator 98 that it slides around.

Figure 26:
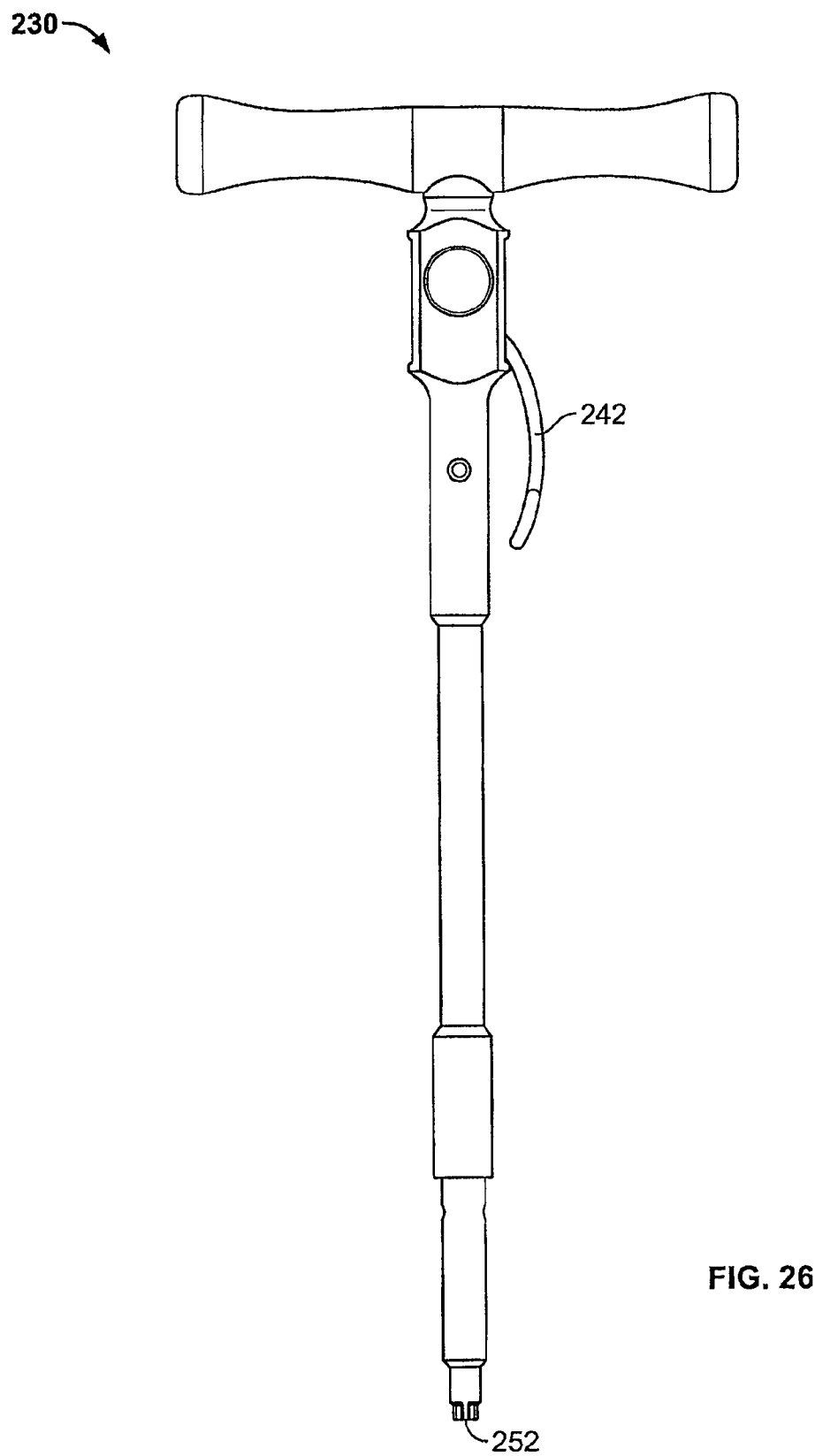
FIG. 26 is a front elevation view of the cap inserter of FIG. 24.
Figure 41:
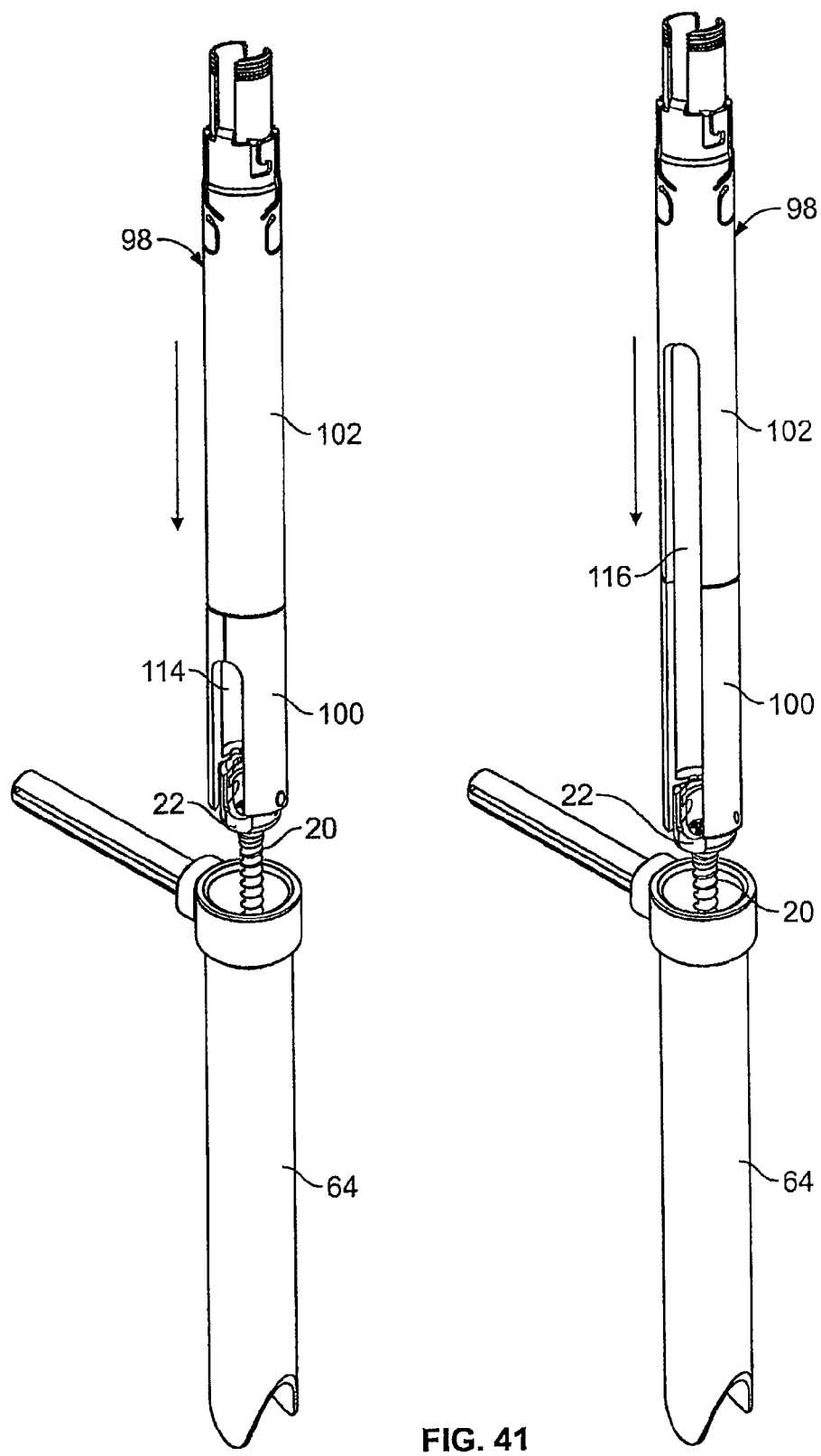
FIG. 41 is a perspective view of two yoke manipulators, two bone anchors with yokes mated therewith, and two docking ports.
Figure 42:
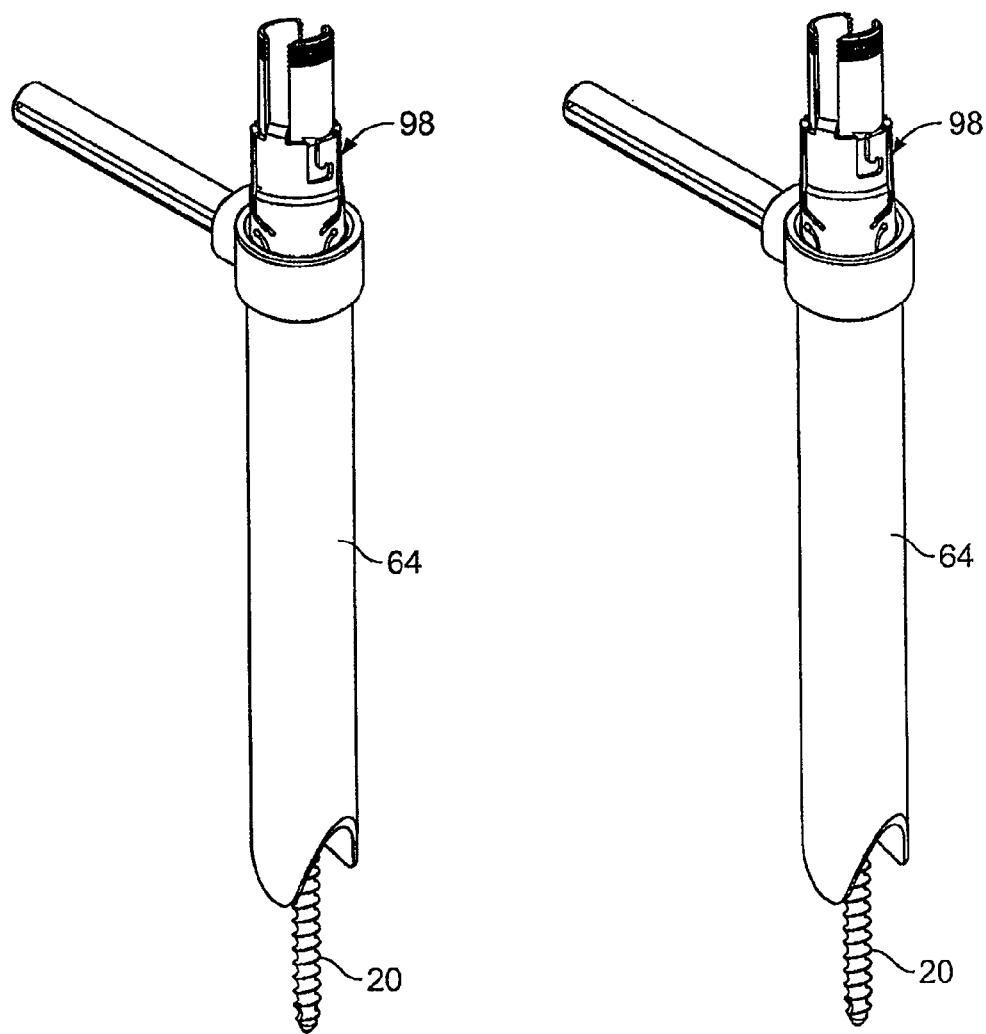
FIG. 42 is a perspective view of two yoke manipulators, two bone anchors with yokes mated therewith, and two docking ports after the bone anchors have been secured to the bone.
Figure 43:
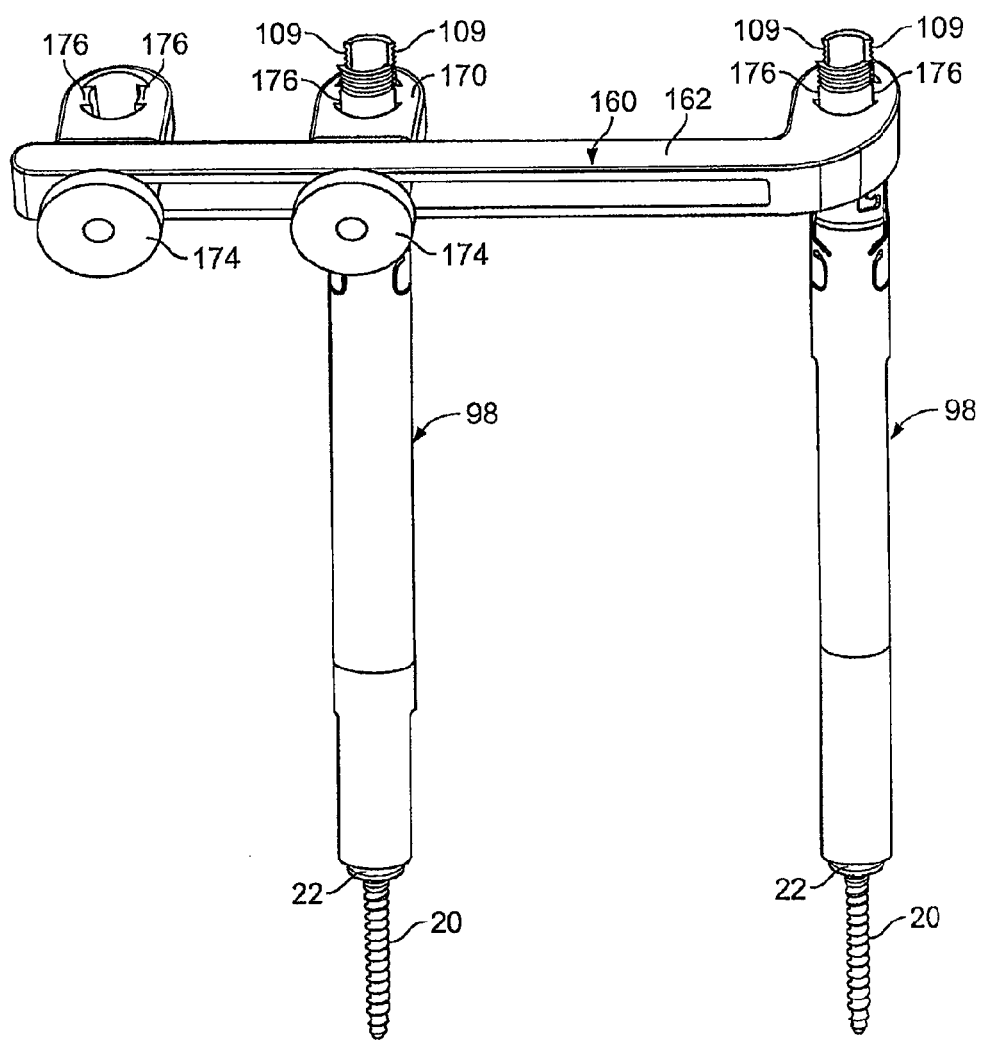
FIG. 43 is a perspective view of two yoke manipulators with the yokes and bone anchors mated therewith, and a guide bar.
Figure 44:
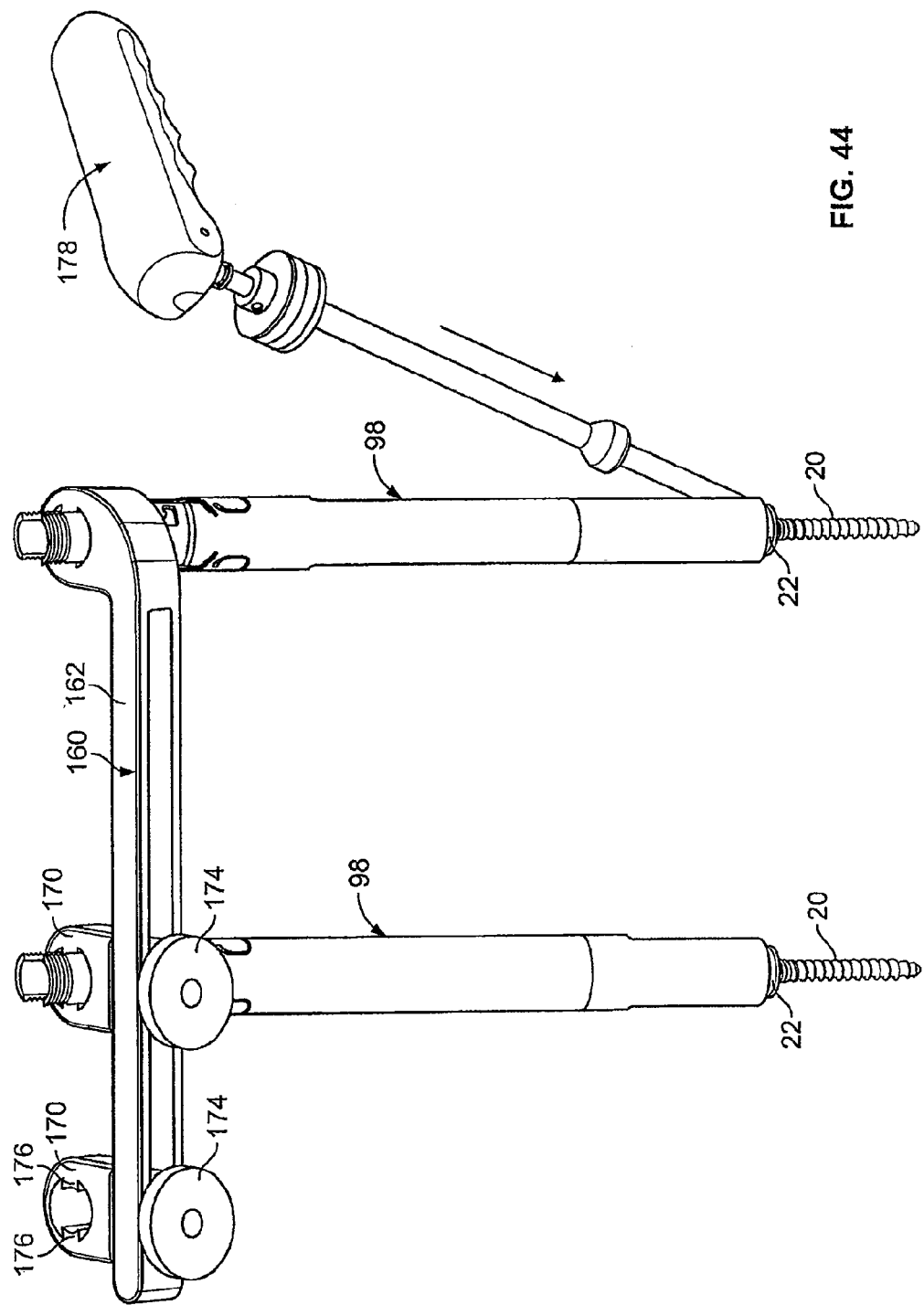
FIG. 44 is a perspective view of two yoke manipulators with the yokes and bone anchors mated therewith, a guide bar, and a rod inserter.
Figure 45:
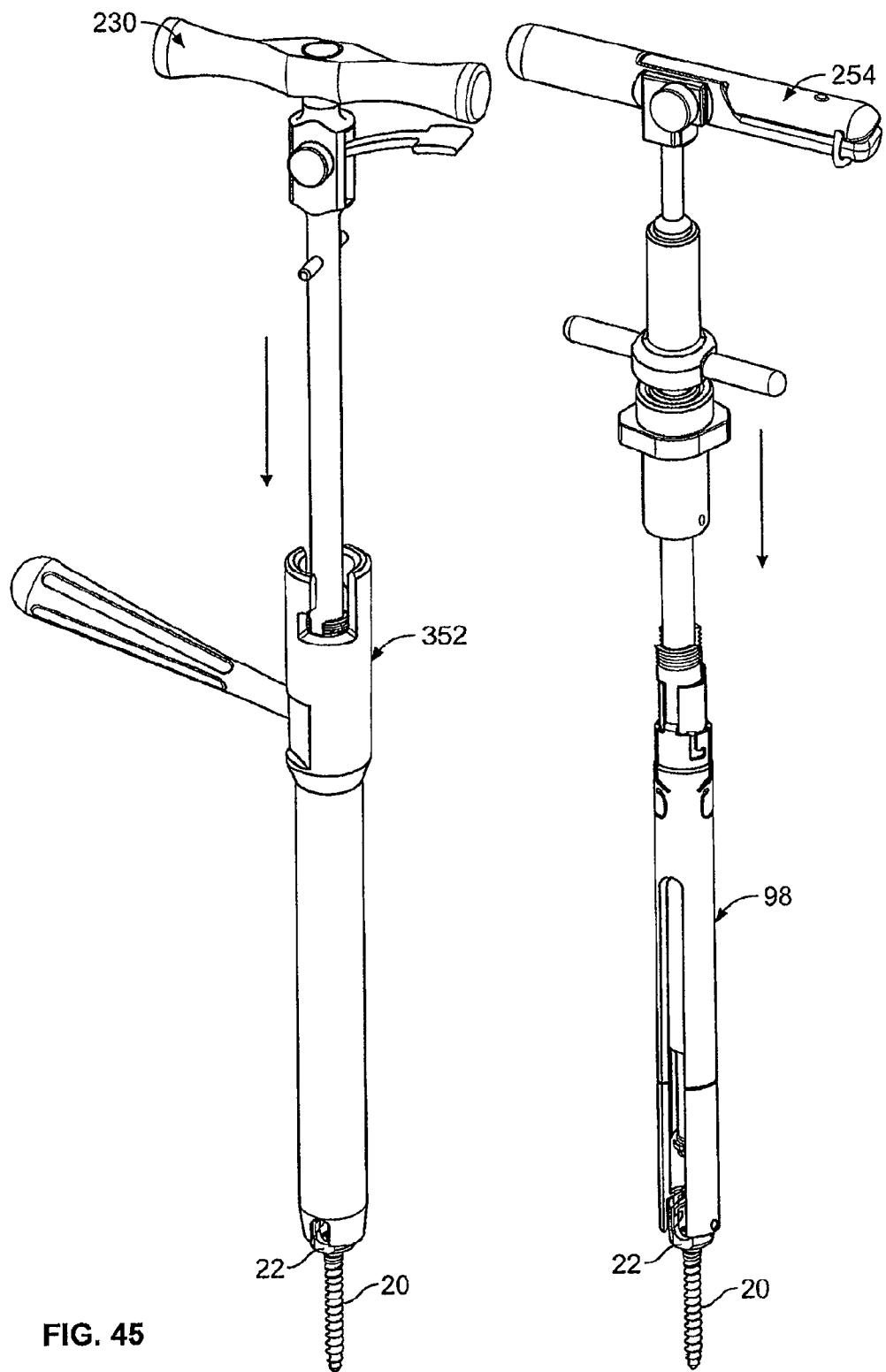
FIG. 45 is a perspective view of two yoke manipulators with the yokes and bone anchors mated therewith, a guide bar, a cap inserter and a rod persuader.
Figure 46:
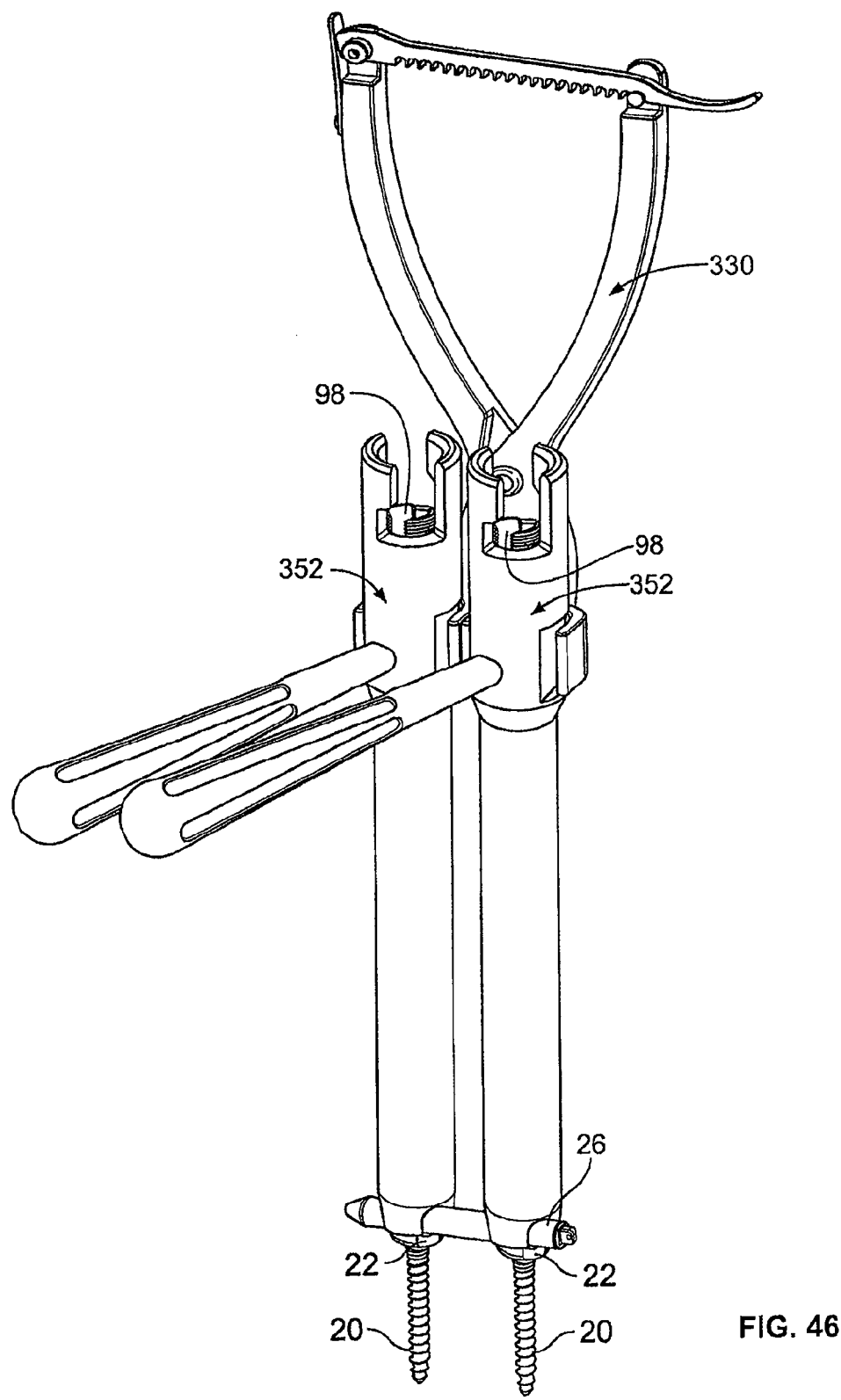
FIG. 46 is a perspective view of two yoke manipulators with the yokes and bone anchors mated therewith, two counter torque tubes, and a compression-distraction tool.
Figure 47:
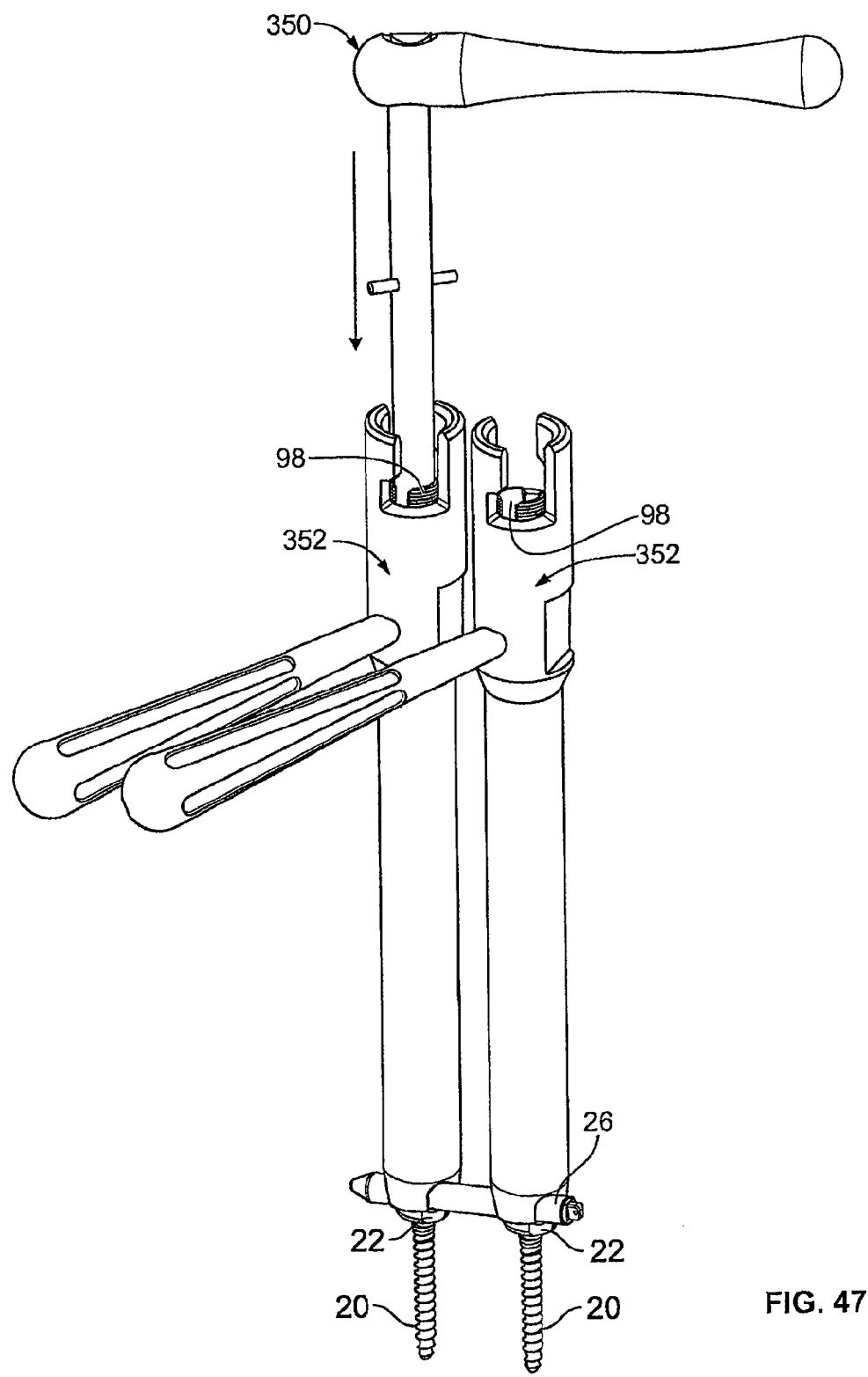
FIG. 47 is a perspective view of two yoke manipulators with the yokes and bone anchors mated therewith, and a final locker.

Demonstrative arrangements of the MIS system tools are depicted in FIGS. 41-47. As shown in FIG. 41, the yoke manipulators 98 are placed within the docking ports 64 having the bone anchors 20 and the yokes 22 attached thereto. To attach the yokes 22 to the yoke manipulators 98, an opening 113 on the yoke 22 is mated with the connecting structure 124 of the inner sleeve 100 of the yoke manipulator 98. After the yoke 22 and the inner sleeve 100 are mated, the outer sleeve 102 is slid down the inner sleeve 100 and the two are mated together. Mating the two sleeves 100, 102 together secures the engagement between the inner sleeve 100 and the yoke 22. As shown in FIG. 42, the yoke manipulators 98 are advanced through the docking port 64 where the bone anchors 20 are then rotated through the bone. After the bone anchors 20 have been seated in the bone, the guide 160 may be attached to the yoke manipulators 98, to ease insertion of the connecting member 26. As shown in FIG. 43, the projections 176 of the slide body 165 of the guide bar 160 mate with a pair of slots 109 on the second end 108 of the yoke manipulators 98. As discussed previously, the slide body 165 can move within the horizontal slot 164 such that the guide bar 160 can accommodate differently sized patients and can also be moved during the subsequent compression or distraction stage. As shown in FIG. 44, the rod inserter 178 is advanced down one manipulator 98, preferably the longer slot manipulator 98 if one is present. Then, the rod inserter 178 is advanced through the stages such that the connecting member 26 is seated within the yokes 22. After the connecting member 26 is seated within the yokes 22, the caps 24 are positioned within the yoke 22. As discussed previously, the caps 24 are delivered to the yokes 22 by the cap inserter 230 or rod persuader 254. The rod persuader 254 having a mechanical advantage such that the caps 24 inserter second in time can be more easily seated. The caps 24 are delivered to the yokes 22 by splaying the insertion end of the tool and creating a secure engagement between the insertion tool and the cap 24. After the caps 24 are positioned within the yokes 22, the caps 24 are rotated to the pre-lock configuration. This allows the bone anchors 20 and yokes 22 to move relative to the connecting member 26. After the caps are in the pre-lock position, the compression-distraction tool 330 can be used to move the bone anchors 20 together as shown in FIG. 26 or apart from one another. Finally, the final locking tool 350 is used to move the caps 24 to from the pre-lock position to the final lock position. After the caps 24 are in position, the tools can be removed from the system.

In one example of the procedure, the patient is placed in the prone position on an operating table. For operative fluoroscopy to be most successful, the table may be radiolucent. A guide wire can be placed using a Jamshidi needle and fluoroscopy equipment to establish the position and orientation of the guide wire on the pedicle. The Jamshidi needle is advanced slightly further than the planned length of the bone anchor 20. If the bone resists, the Jamshidi needle may be driven into position by pushing on the handle and using a twisting motion. The shoulder of the tool will permit over-advancement of the tool into the bone. If the bone completely resists the attempts to manually penetrate the bone, the Jamshidi can be used as a drill guide. After penetrating the bone, the guide wire may be placed into the bore of the Jamshidi needle and gently tapped into the bone. The Jamshidi needle is removed and the guide wire is left in position.

Subsequent to the positioning of the guide wire, the tissue surrounding the guide wire is dilated. The dilation tools can be selected from various options. For example, if the series dilators are used, four dilators are used to create a path through the fascia and muscle to establish a working portal. The smallest diameter tube enters the tissue first, followed by increasingly larger diameters, until all four tubes are employed. Preferably the tubes are pushed down far enough for each of the tips to contact bone.

After the tissue is stretched, the docking sleeve or port 64 can be positioned around in situ tissue dilators with the acute angle of the tip facing the spinous process, and the obtuse angle of the tip facing the transverse process. In one form, the docking port 64 may have an orientation direction etched on the outside of the tube to aid in placement. The docking port 64 should be advanced until it rests against the facet and transverse process, and can restrict soft tissues from encroaching. The series dilation tools or other dilation tools used can be removed from the system, leaving the guide wire in place.

The pedicle where the bone anchor 20 is seated is next prepared. After which, the bone anchor 20 is placed and aligned. The prongs 112 of the yoke manipulators 98 are splayed to place around the yoke 22 such that the pins 24 engage openings 113. Then, the outer sleeve 102 is slid down the inner sleeve 100 to secure the yoke 22 to the yoke manipulator 98. The screw driver is then fed down the yoke manipulator 98 and mated with the bone anchor 20. The screw driver may include a separate handle that is attached to the driver before the driver is inserted into the yoke manipulator 98. Then the bone anchor 20, yoke 22, yoke manipulator 98 and screw driver are advanced to the bone. The bone anchor 20 is placed at the attachment site. The slots 114 and 116 of the yoke manipulators 98 can be oriented in the cephalad/caudal direction. To ensure correct depth placement of the bone anchors 20, the depth can be radiographically examined. In addition, the yoke manipulator 98 may include a ring. If the ring is driven below the top of the docking port 98, then the bone anchors 20 may have been driven too far. After the bone anchors 20 are driven into position, the screw driver is removed from the system. The other bone anchors 20 are driven into the bone in the same manner described above.

The yokes 22 are then aligned such that they can receive the connecting member 26. The guide bar 160 or 160*b* may be attached to the yoke manipulator 98. The attachment brackets 172, 174 or 171*b*, 172*b*, and 174*b* are moved until the yoke manipulators 98 are parallel or in another desired alignment. Then each of the sliding bodies is tightened into position.

After the yoke manipulators 98 are positioned, the connecting member 26 is inserted. To being, the connecting member 26 is attached to the rod inserter 178. To do this, the locking sleeve 194 is slid backwards such that the connecting member 26 can be placed within the prongs 200. The pins 204 are aligned with the bore 186 of the connecting member 26. Then the locking sleeve 194 is moved forward to secure the connecting member 26 to the rod inserter 178.

The connecting member 26 insertion is primarily controlled by the surgeon. The surgeon aims the rod inserter 178 between the slots 114, 116 in the yoke manipulators. The nose 180 of the connecting member 26 is placed in the caudal-most slot of the yoke manipulators 98. The connecting member 26 is pushed then down to the level of the yoke 22. If the connecting member 26 is too high, the surgeon may need to compress excess soft tissue.

The connecting member 26 is pushed into both yokes 22. The position within the yokes 22 can be verified by looking down the yoke manipulators 98. The position can also be verified radiographically. The nose 180 of the member 26 preferably extends past the yoke 22 such that the full diameter body 182 of the connecting member 26 is within the yoke 22.

After the connecting member 26 is positioned within the yokes 22, the counter torque tube is deployed over one yoke manipulator 98. The pins 380 of the counter torque tube 352 are aligned with slots on the second end 108 of the yoke manipulator 98. Then the cap 24 is inserted using the cap inserter 230 and counter torque tube 352. Two cross pins 248 on the cap inserter 230 can indicate depth and orientation. The counter torque tube 253 also may include etchings to ensure proper depth and positioning. Typically, the cap inserter 230 is turned clockwise to seat the cap 24 and therefore, it may be beneficial to begin the procedure as far counter-clockwise as the tools will allow. The surgeon typically may use tactile feed back to feel the cap 24 seat atop the connecting member 26. The cap inserter 230 is released from the cap 24 and pulled straight up to avoid loosening the cap. The rod persuader 254 is used in a similar manner to seat subsequent caps 24. The cap 24 can be loaded by latching the ring 284 and then the cap 254 is advanced down toward the yoke 22.

After the caps 24 are seated, the distance between the bone anchors 20 can be adjusted using the compression-distraction tool 330. After the bone anchors 20 are positioned, the caps 24 are tightened to the final-lock position. After final locking, the tools are removed and the incision closed.

The MIS system may include a number of alternative or additional tools such that a surgeon can further customize the implantation procedure. As previously indicated, the implant and the implant procedure are chosen based on the condition of the patient, the anatomy of the patient, and the preferences of the surgeon. Thus, by providing additional options for implant insertion, the surgeon can chose tools and devices that are more suited to a particular patient or are more suited to the surgeon's preferences.

As shown in FIG. 2, the connecting member 26 includes the body portion 182 and an attachment end 184 that may have a reduced portion or other structure for securing the connecting member 26 to the rod inserter 178. Positioning the attachment end 187 in the yoke 22 can be problematic the cap 24 may not properly secure the connecting member 26 within the yoke 22. The preferred positioning having the attachment end 184 outside of the yoke 22 of the pedicle screw assembly 21. In addition to positioning of the attachment end 184 outside of the yoke 22, the nose or tip 180 of the connecting member 26 should be kept in the far yoke 22.

The rod inserter 178 may include a bulbous portion 199 to limit how closely the rod inserter 178 can be to the yoke manipulator 98 and also how far the tool can advance into the wound. Depending on a surgeon's particular preference, such further advancement may provide needed flexibility.

One of the alternative instruments that may address some of these concerns is the rod insertion tool 1078, illustrated in FIGS. 48A-48D, which, like the rod inserter 178, may be used to guide and position the spinal rod or connecting member 26 into the yokes 22. The rod insertion tools 178, 1078 can be used in conjunction with the yoke manipulators 98 to position the body 182 of the connecting member 26, which has a generally constant diameter body 182, within the yokes 22. The rod inserter 1078 of FIGS. 48A-48D differs from the rod inserter 178 of FIGS. 17-23 in that it includes an adjustment sleeve 1091 and a latch 1102.

Figure 48A:
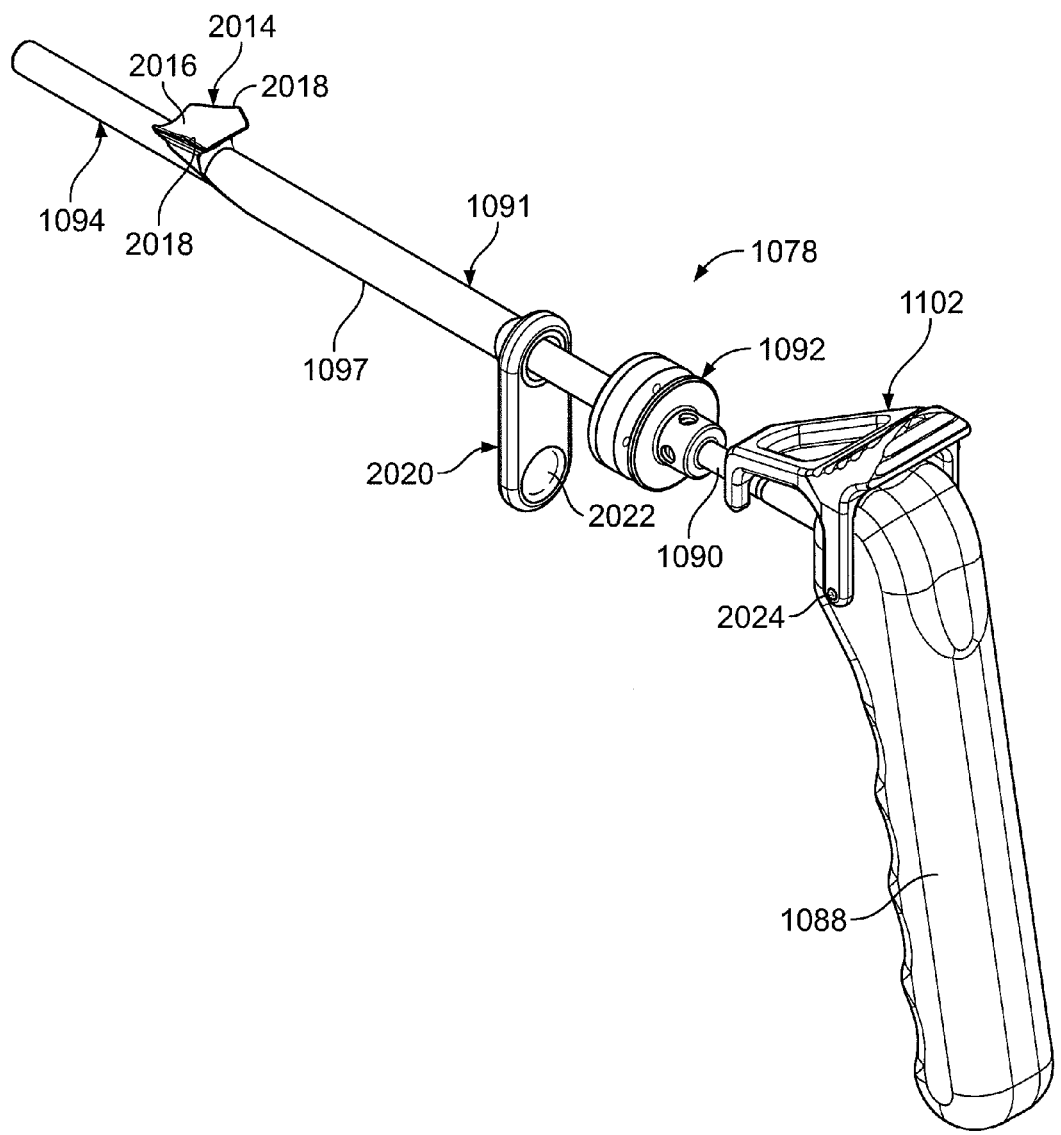
FIG. 48A is a perspective view of an alternative rod inserter having an adjustment sleeve for verifying the positioning of the inserted rod.
Figure 48B:
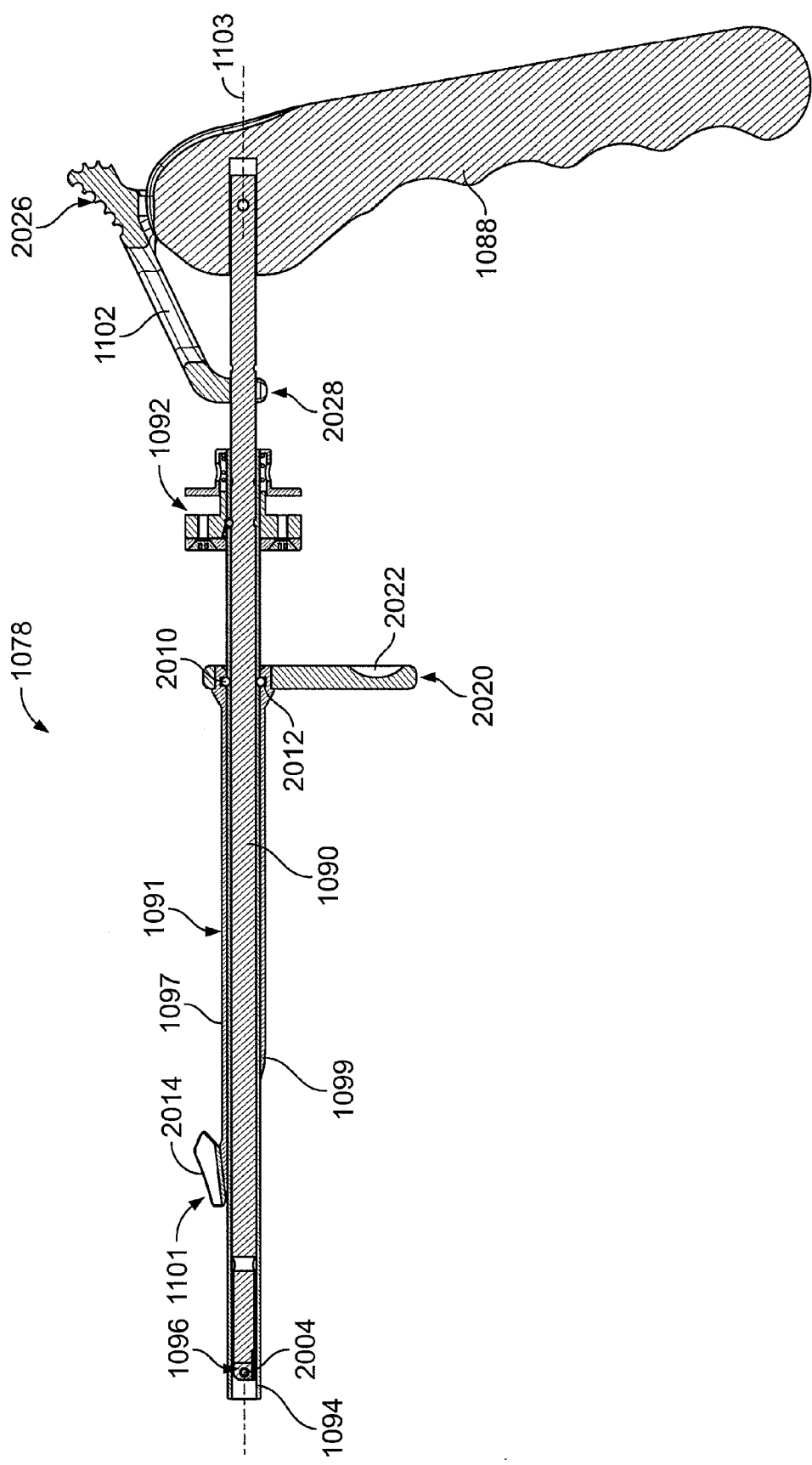
FIG. 48B is a cross-sectional view of the rod inserter of FIG. 48A showing the coaxial arrangement of an inner shaft, a locking sleeve, and the adjustment sleeve.

In the embodiment illustrated in FIGS. 48A-B, the adjustment sleeve 1091 that may be employed to verify positioning of the connecting member 26 and correct its placement if necessary. Specifically, the adjustment sleeve 1091 may be used to pull the attachment end 184 of the connecting member 26 outside of the yoke 22. The adjustment sleeve 1091 of FIG. 48A includes structure, described below, that generally keeps the surgeon from pulling the tip 180 of the connecting member 26 out of the yokes 22 by over-rotating the inserter 1078 such that the inserter 1078 is directly adjacent to the yoke manipulator 98.

The adjustment sleeve 1091 is positioned over the outer locking sleeve 1094 and has a friction member 2010 so that the adjustment sleeve 1091 remains where it is positioned after being released by the surgeon. In one preferred embodiment, the friction member 2010, as shown in FIG. 48B, is a resilient O-ring member, such as a silicon O-ring, positioned between the outer locking sleeve 1094 and a groove 2012 inside the adjusting sleeve 1091 to project radially inward therefrom and to frictionally engage with the outer locking sleeve 1094. The adjustment sleeve 1091 further includes a shaft 1097 having an insertion end 1099 that is slanted such that only a projecting portion 1101 of the end 1099 is inserted into the patient. The slanted edge 1099 extends obliquely to the tool axis 1103 to minimize having the edge 1099 catch on tissue as the tool is inserted into the wound.

The insertion end 1099 of the adjustment sleeve 1091 also includes a wedge 2014 that facilitates correct placement of the rod member 26 in the yokes 22. When the adjusting sleeve 1091 is pushed down toward the wound, the wedge 2014 becomes positioned between the rod inserter 1078 and the yoke manipulator 98. Thus, the connecting member 26 will be pulled out such that the attachment end 184 thereof is not within the yoke 22. The wedge 2014 also can prevent misplacement of the rod inserter 1078 directly adjacent the manipulator 98 to thereby keep the surgeon from pulling the tip 180 out of the far yoke 22. The wedge 2014 has a central portion 2016 that is connected to the sleeve 1091 and two projecting sides 2018 that curve outward from the sleeve 1091 to form a seat where the yoke manipulator 98 received thereagainst. The adjusting sleeve 1091 and wedge 2014 are employed after the connecting member 26 has been generally positioned between the yokes 22 and the wedge 2014 creates a distance between the yoke manipulator 98 and rod inserter 1078 such that the attachment end 184 of the connecting member 26 is not within the near or proximate yoke 22 so that the closure cap 24 will be seated atop the body 182 of the connecting member 26. Opposite the insertion end 1099, the sleeve 1091 includes a radially or laterally extending tab 2020 which can be used to move the adjustment sleeve 1091 about the outer locking sleeve 1094 of the rod inserter 1078. The tab 2020 has a depression 2022 to provide a gripping surface.

Figure 49A:
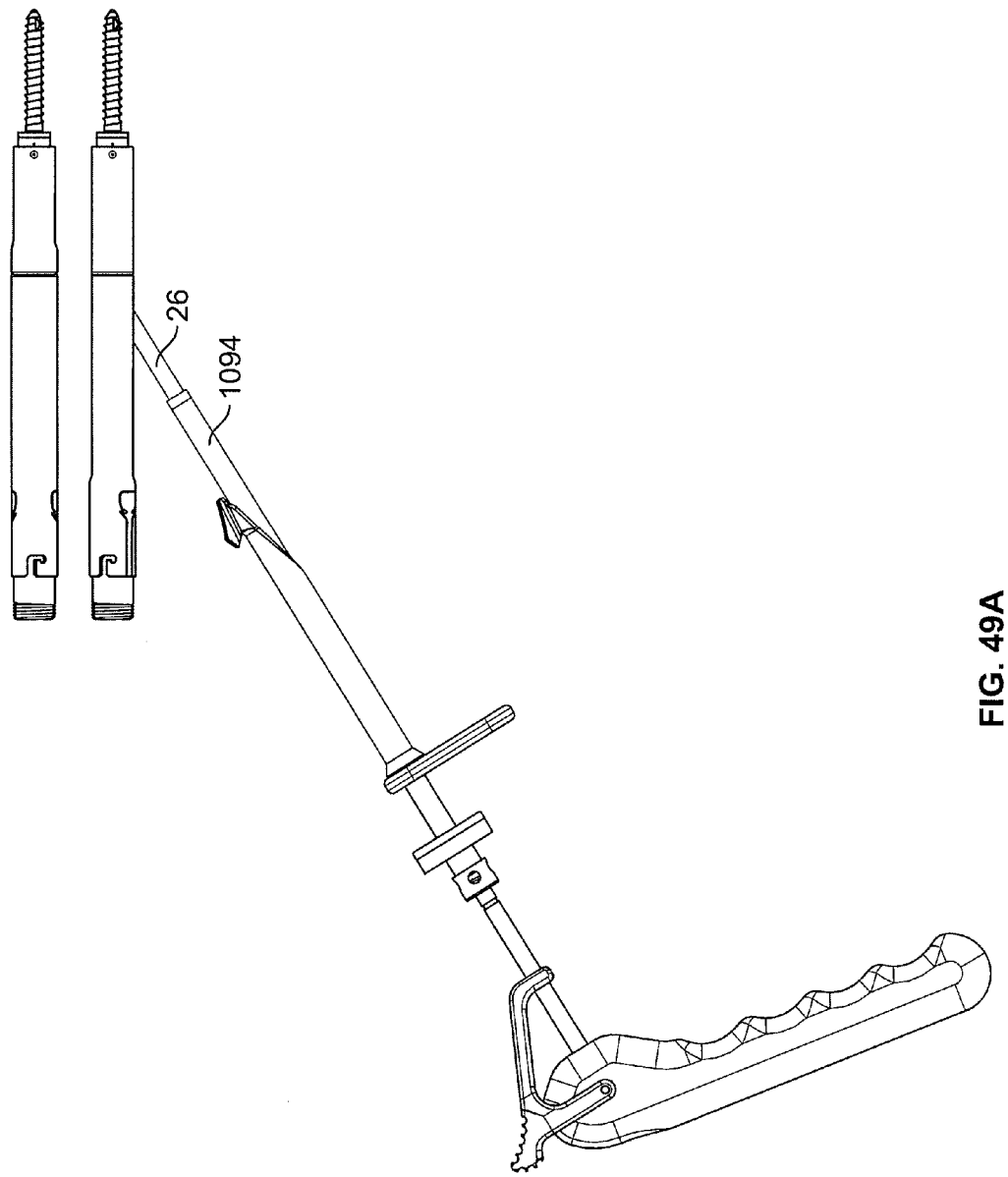
FIG. 49A is a side view of the rod inserter of FIG. 48A, the yoke manipulators of FIGS. 7-12, and the pedicle screw assemblies of FIG. 1 at an initial stage of the rod insertion procedure.
Figure 49B:
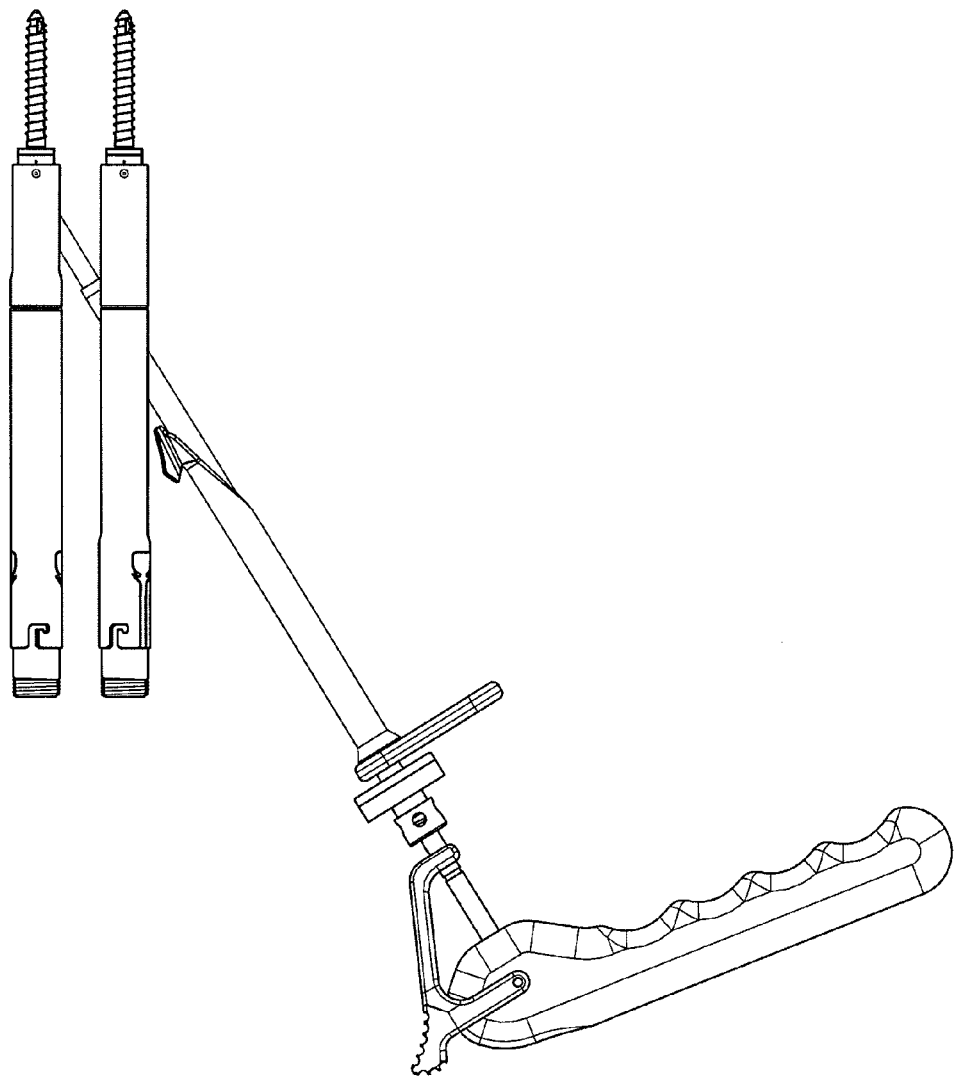
FIG. 49B is a side elevation view of the tools of FIG. 49A in a first intermediate stage of the rod insertion procedure.
Figure 49C:
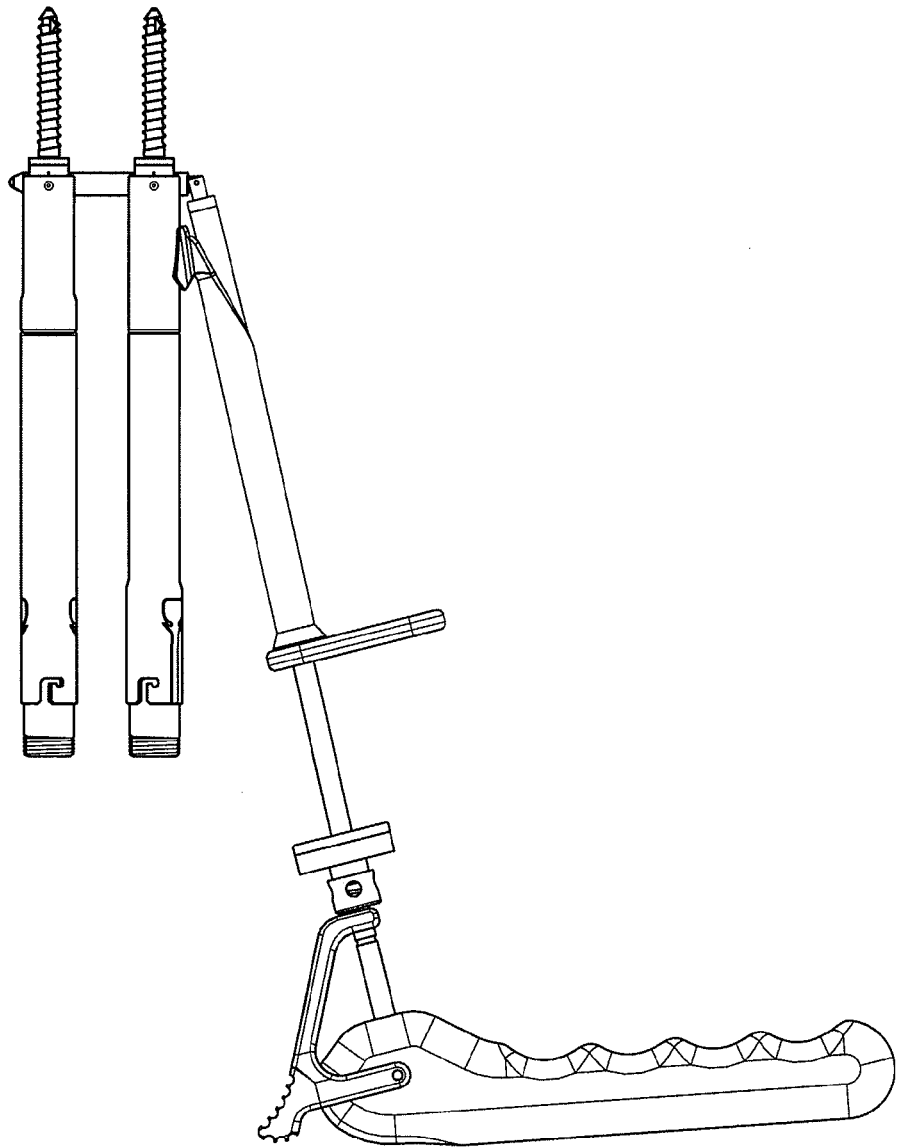
FIG. 49C is a side elevation view of the tools of FIG. 49A in a second intermediate stage of the rod insertion procedure with the nose of the connecting member in the yoke of the far pedicle screw assembly.
Figure 49D:
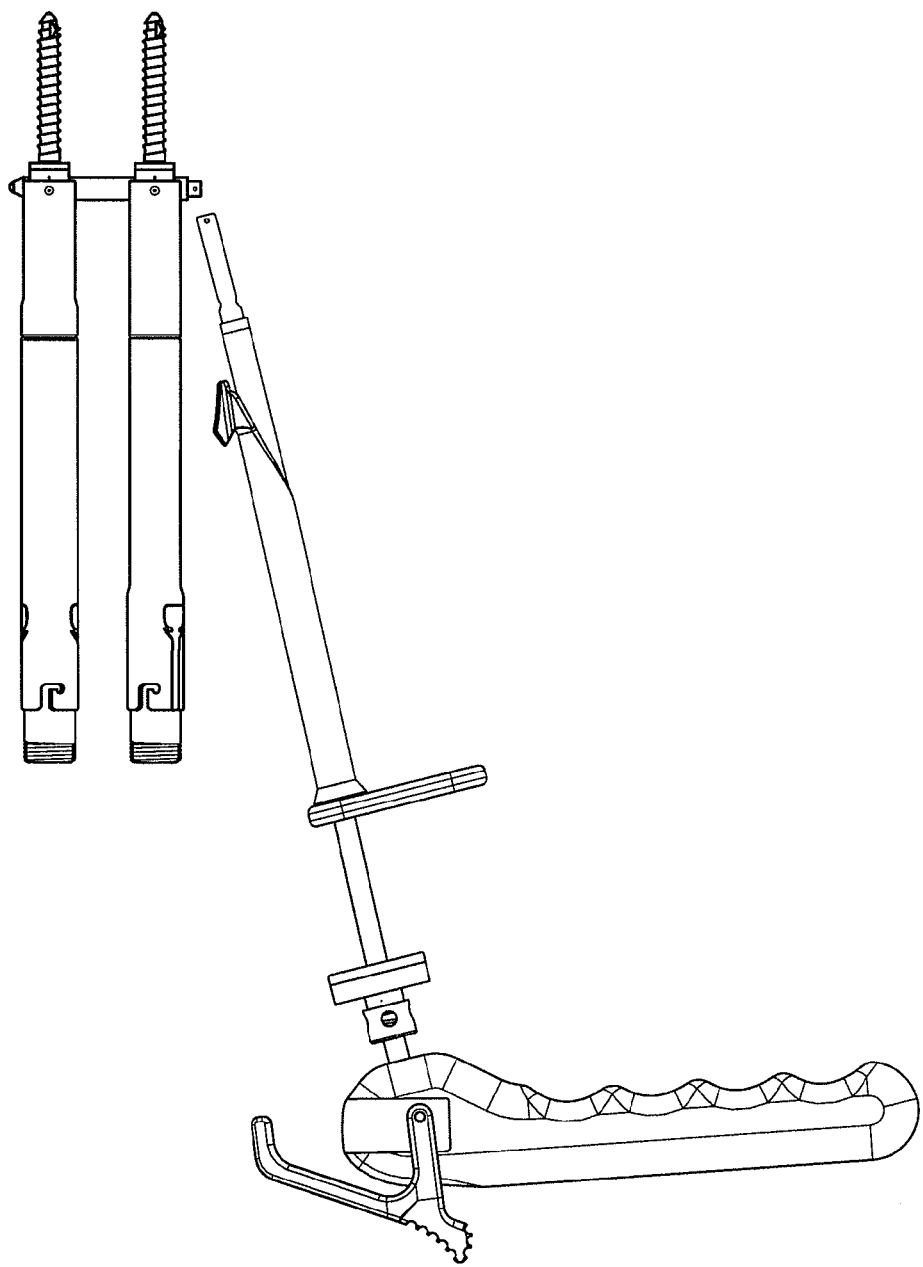
FIG. 49D is a side elevation view of the tools of FIG. 49A in a final stage of the rod insertion procedure with the connecting member within the yokes of the pedicle screw assemblies.

The rod inserter 1078 further includes a latch 1102 for limiting the movement of the shift assembly 1092 and the locking sleeve 1094. If the locking sleeve 1094 is inadvertently advanced too far up the inner shaft 1090 during the MIS procedure, the connecting member 26 may be prematurely released from the rod inserter 1078 by allowing the prongs 2000 to splay. The latch 1102 is attached to the handle 1088 by two pins 2024. A safety position shown in FIGS. 49A-49C limits the surgeon from moving the shift assembly 1092 and locking sleeve 1094 too far up the inner shaft 1090 and the shift assembly 1092. The latch 1102 can rotate about the pins 2024 from the safety position (FIGS. 49A-C) to the disengaged position (FIG. 49D) by engaging a finger portion 2026. The latch 1102 includes a stopper 2028 with a U-shaped portion 2030 that engages the inner shaft 1090 in the safety position. When the latch 1102 is in the safety position, the movement of the shift assembly 1092 is constrained from moving too close toward the handle 1099. This is so that when the surgeon is moving the shift assembly 1092 toward the handle 1088 the shift assembly 1092 will abut the stopped 2028 before the locking sleeve 1094 has released the prongs 2000 from the connecting member 26. Accordingly, in the latched or safety position, the latch member 1102 limits accidental removal of the connecting member 26 from the rod inserter 1078. The latch 1102 is pivoted to the disengaged position when the shift assembly 1092 needs to be advanced farther up the inner shaft 1092 to disengage the connecting member 26 from the rod inserter 1078 as shown in FIG. 49D.

Figure 48D:
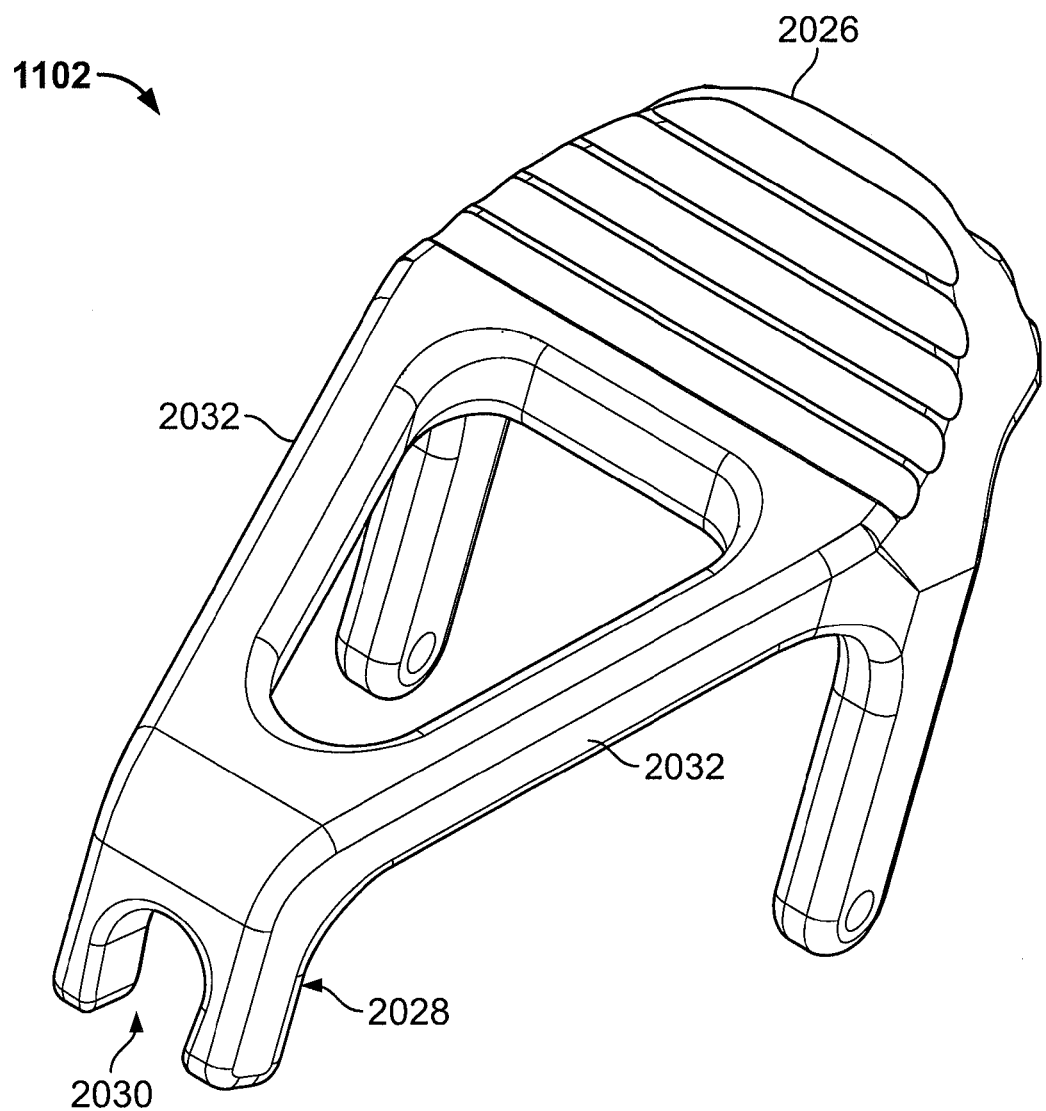
FIG. 48D is a perspective view of a latch portion of the rod inserter of FIG. 48A used for limiting the movement of the locking sleeve.

As shown in FIG. 48D, the latch 1102 includes two connecting arms 2032 that extend from the stopper 2028 to the finger portion 2026; however, it is contemplated that the latch 1102 may be unitary. The latch 1102 is comprised of black radel although other suitable materials can be used. Similar to the inner shaft 190 of rod inserter 178, the inner shaft 1090 may have etchings or grooves that indicated where the shift assembly 1092 should be positioned to inform the surgeon of the configuration of the end of the tool that is inserted into the wound. For example, the inner shaft 1090 may include characters or depictions to indicate the unlock, articulate, and lock positions.

To position the spinal rod or connecting member 26 into the yokes 22 of the pedicle screw assemblies 21, the connecting member 26 is pivotably connected to the attachment end 1096 of the inner shaft 1090 about a pivot axis. Before the connecting member 26 is advanced through the slots 114, 112 of the yoke manipulators 98, the outer locking sleeve 1094 is positioned over the pivot axis to limit or block pivoting of the connecting member 26 about the pivot axis. After securing the connecting member 26 to the rod inserter 1078, the connecting member 26 is advanced through the long slot 114 of the proximal yoke manipulator 98 and then a first portion or nose 180 of the connecting member 26 is inserted into the far yoke 22 of one of the pedicle screw assemblies 21. The outer locking sleeve 1094 is then moved to an unblocking position exposing the pivot axis to thereby permit pivoting of the connecting member 26 about the pivot axis. The pivoting movement of the connecting member 26 may be limited such that the connecting member 26 may pivot in one direction while limiting or restricting the pivoting in the opposite direction when the locking sleeve 1094 is in the unblocking position. While in the pivoting position, the rod inserter 1078 can be manipulated to place a portion of the connecting member 26 is a second closer or proximal yoke 22 of another of the pedicle screw assemblies 21. Finally, to disconnect the connecting member 26 from the inner shaft 1090, the outer locking sleeve 1094 may be advanced sufficiently away from the pivot axis to allow the prongs 2000 of the inner shaft 1090 to be disengaged from the connecting member 26. The locking sleeve 1094 may be secured relative to the inner shaft in each of the release, unblocking, and blocking positions. Further, the locking sleeve 1094 may be unlocked to move between the release, unblocking, and blocking positions.

The different configurations between the connecting member 26 and the rod inserter 1078 are used in the various stages of rod insertion. As illustrated in FIG. 49A, the pivot connection between the connecting member 26 and the inner shaft 1090 is covered such that the pivoting movement of the connecting member 26 is blocked or prevented. In this configuration, the surgeon may direct the connecting member 26 through the proximal yoke manipulator 98 having the long slot 114 toward the far yoke manipulator 98 having the short slot 116. The surgeon then guides the tip 180 of the connecting member 26 into and/or just past the yoke 22, as illustrated in FIG. 49B. When the tip 180 of the connecting member 26 is positioned at the far yoke 22, the inserter 1078 is adjusted to the articulating position by pulling back on the shift assembly 1092. The surgeon also moves the locking sleeve 1094 by pulling the shift assembly 1092 upward toward the latch 1102. As discussed above, the movement of the shift assembly 1092 is limited by the latch 1102. When the locking sleeve 1094 is pulled back such that the shift assembly 1092 is adjacent the latch 1102, the pivot connection is unblocked or exposed such that the connecting member 26 may articulate. In this configuration, the connecting member 26 is pivoted or rotated downward such that the end 184 opposite the tip 180 can be positioned within the proximal yoke 22 attached to the yoke manipulator 98 having the long slot 114. As shown in FIG. 49C, the latch 1102 limits the surgeon from pulling the shifting assembly 1092 too far upwards toward the handle 1088. After the connecting member 26 has been rotated into position between the yokes, the surgeon may ensure that the attachment end 184 is not located within the proximal yoke 22 by moving the inner shaft 1090 of the inserter 1078 nearly parallel to the yoke manipulator 98 and thereby pulling the attachment end 184 out of the yoke 22. However, depending on the surgeon, the rod inserter 1078 may already be adjacent the yoke manipulator 98 and the surgeon may employ the adjustment sleeve 1091 as a wedge to pull the attachment end 184 out of the proximal yoke 22. The latch 1102 may be rotated upward, as illustrated in FIG. 49D, to allow the shift assembly 1092 and the locking sleeve 1094 to be moved to expose a substantial portion of the opposing prongs 2000 such that the prongs 2000 splay outward and disengage or release the connecting member 26.

Turning to more of the details of the construction, the rod inserter 1078, like inserter 178, includes a handle 1088 to which an inner elongate rod or shaft 1090 is attached, for example, by welding, threaded engagement, pins, screws, and adhesive, among others. The inner shaft 1090 having a shift assembly 1092 and an outer control sleeve or a locking sleeve 1094 mounted thereon. The inner shaft 1090 and the locking sleeve 1094 are configured as a shaft assembly having a longitudinal axis. The inner shaft 1090 of the rod inserter 1078 including an attachment end portion 1096 having connecting structure, such as a pivot connection, configured to mate with the attachment end 184 of the connecting member 26. For example, the attachment end 1096 may be adapted to pivotably engage the spinal rod or connecting member 26 about a pivot axis. To aid in the attachment of the connecting member 26, the inner shaft 1090 of the rod inserter 1078, includes two slots 1098 at the attachment end 1096 that separate two opposing prongs 2000 from each other. During the MIS procedure, the prongs 2000 may be situated about portions of the connecting member 26 similar to the configuration previously discussed with respect to inserter 178. As discussed below, the outer locking sleeve 1094 of the shaft assembly may be moved relative to the inner shaft 1090 to prevent or block the connecting member 26 from pivoting.

The opposing prongs 2000 may include connecting structure 2002 that mates with corresponding structure 186 of the connecting member 26. The connecting structure 2002, shown in FIG. 48C such as a pivoting connection, and may include a recess, a boss or a projection, such as protuberances or frustoconical projections 2004 that project inward from the inwardly facing surfaces of the opposing prongs 2000. As shown in FIG. 2, the connecting structure 186 may be a recess or a through-bore, but may also include a boss, flat, capture, groove, or ridge, among others, configured to engage corresponding structure present on the rod inserter 178, 1078. It is also contemplated that the projections or protuberances be located on the connecting member 26 and the recesses located on the inwardly facing surfaces of the pair of opposing prongs 2000.

Once the connecting structure 2002 of the prongs 2000 is mated with corresponding structure 186 on the connecting member 26, a pivot connection about a pivot connection is established between the connecting member or rod 26 and the inserter tool 1078. By sliding the locking sleeve 1094 down the inner shaft 1090, the opposing prongs 2000 of the inner shaft 1090 are secured into position about the connecting member 26 thereby clamping the connecting member 26 between the prongs 2000. The locking sleeve 1094 may be slid down along the inner shaft 1090 to at least partially secure the prongs 2000 around the attachment end 184 of the connecting member 26 in a similar fashion to rod inserter 178. To keep the connecting member 26 generally rigidly attached to the inserter tool 1078 during the beginning of the rod insertion procedure, the locking sleeve 1094 is slid down such that the locking sleeve 1094 surrounds at least a substantial portion of the inner shaft 1090. By having the locking sleeve 1094 surround the pivot axis and connection between the connecting member 26 and the inner sleeve 1090, the member 26 is blocked from pivoting and is secured rigidly to the rod inserter 1078. Such a rigid connection is used during the MIS procedure to direct the connecting member 26 through the slots 114, 116 and into the yokes 22. After the nose or tip 180 of the connecting member 26 is positioned in the far yoke 22, the connecting member 26 is allowed to pivot such that the attachment end 184 pivots downward toward the proximal yoke 22. The locking sleeve 1094 of the rod inserter 1078 is moved upward toward the handle such that the pivot connection is exposed and the pivoting is no longer blocked. In the pivoting configuration, the locking sleeve 1094 remains positioned close enough to the pivot connection to keep the opposing prongs 2000 engaged with the attachment end 184, but the locking sleeve 1094 is not surrounding the pivot connection and does not prevent or block the connecting member 26 from pivoting. After the connecting member 26 has been seated in each of the yokes 22, the connecting member 26 can be released from the rod inserter 1078 by shifting the locking sleeve 1094 from the pivoting or unblocking position to the release position whereby the locking sleeve 1094 is sufficiently spaced from the opposing prongs 2000 of the inner shaft 1090 to permit the prongs 2000 to flex outwardly relative to each other to release the connecting member 26. Before the connecting member 26 is released from the rod inserter 1078, the latch 1102 is pivoted to the disengaged position such that the locking sleeve 1094 can be moved to the disengage position.

After the connecting member 26 is generally laterally positioned within the yokes 22 as described previously, the member 26 is sufficiently seated within the yokes 22 such that the closure caps 24 can fit within the yokes 22 to secure the connecting member 26. Depending on the patient's anatomy, the connecting member 26 may extend at an upward incline to such a degree such that the closure cap 24 cannot fit within the yoke 22. In such a circumstance, the connecting member 26 must be pushed into the yoke 22. The rod persuader 254, along with the closure cap 24 may be used to seat the connecting member 26 and to secure the closure cap 24 into position by rotating the caps 24. However, the rod persuader 254 may encounter a number of limitations depending on the patient anatomy and the preferences of the surgeon.

If the patient has a significantly displaced vertebra, the force required to reduce the connecting member 26 to its seated position in the yoke 22 may be quite significant and such large loads may be problematic. Seating of the connecting member 26 may require one vertebra to be adjusted relative to another vertebra; a significant amount of force can be required for the persuader 254 to move the vertebra via the closure cap 24 and yoke manipulator 98. The persuader 254 may encounter several problems when employed on patients having significantly displaced vertebra: the cap 24 may be pushed onto the tip of the persuader tool 254 too tightly and could become difficult to disengage from the persuader 254; the connection between the inner and outer sleeves 100, 102 of the yoke manipulator 98 could fail under the large loads; and the prongs 112 of the yoke manipulator 98 that attach to the yoke 22 could splay and disengage from said yoke. Such disengagement of the prongs 112 is especially problematic with manipulators 98 having the long slots 114.

The rod persuader 254 includes a portion that applies axial downward force against the cap 24, engaged with the connecting member 26 to urge the connecting member 26 into the yoke 22, while the persuader 254 uses the yoke manipulator 98 to hold the yoke 22 relative to the cap 24. This axial downward force could force the cap 24 onto the persuader too tightly to be easily or conveniently disengaged. Further, in one exemplary embodiment, the rod persuader 254 connects to the outer sleeve 102 of the yoke manipulator 98 via a bayonet connection illustrated as including a set of pins 329 in FIG. 34. However, the inner sleeve 100 is the portion of the yoke manipulator 98 that attaches to the yoke 22. Thus, the inner sleeve 100 and outer sleeve 102 of the yoke manipulator 98 typically need to be secured relative to one another to transfer the forces of the rod persuader 254 to the yoke 22.

Referring to FIGS. 7-12, the bone anchor 20 and the yoke 22 of the pedicle screw assembly 21 are delivered to the vertebra by the yoke manipulator 98, which includes two cylindrical sleeves 100, 102. The inner sleeve 100 includes two shaft slots 110 that create two shaft arms or prongs 112, which are positioned around portions of the pedicle screw assembly. The outer sleeve 102 is slid over the inner cylindrical sleeve 100 to secure the yoke manipulator 98 to portions of the pedicle screw assembly to prepare the assembly to be delivered to the bone. In one exemplary embodiment, the inner sleeve 100 and the outer sleeve 102 are secured to one another via a spring 134, as shown in FIGS. 7-12. The spring 134 operates such that when it is depressed, the outer sleeve 102 deforms to allow the sleeve 102 to be removed from around the inner sleeve 100. The persuader 254 seats the cap 24 and the connecting member 26 by transferring force from the persuader 254 to the outer sleeve 102, which transfers the force to the inner sleeve 100, and then to the yoke 22. Such a configuration requires a secure connection between the inner and outer sleeves 100, 102 in order to seat the connecting member 26 and cap 24 with the persuader 254. The spring 134 employs elastic deformation to allow the outer sleeve 102 to be removed from around the inner sleeve 100 by raising the finger portion 135 of the spring 134 away from the flat 130 of the inner sleeve 100, as shown in FIGS. 8-9. Thus, if the force needed to seat the connecting member 26 is excessively large, the spring 134 may encounter problems such as disengagement of the spring 134 from the flat 130. The axial force may be significant enough to permanently deform the spring 34. Whether permanent deformation results, the force may nonetheless be large enough to buckle the spring 134 thereby permitting the proximal edge of the spring 134 to move past the corresponding ledge of the inner sleeve thereby disengaging the inner and outer sleeves 100, 102.

To address the problems arising when large forces are required to seat a connecting member 26, a surgeon may prefer to use a convincing tool 2100 instead of the rod persuader 254 to seat the connecting member 26 into the yokes 22. The convincing tool 2100 can be positioned around outside of the yoke manipulator 98 (as opposed to the rod persuader 254 that is advanced down the center bore of the yoke manipulator 98), thereby avoiding having the prongs of the manipulator 98 splaying outwardly. Since the convincing tool 2100 is outside the yoke manipulator 98, the closure cap 24 may be delivered to the yoke 22 in a procedure separate from the procedure that seats the rod. Thus, the closure cap 24 is delivered with another tool, e.g., cap inserter 230, when the convincing tool 2100 is employed, as opposed to having the cap 24 inserted and the connecting member 26 seated by the persuader 254. This allows the connecting member 26 to be seated and the closure cap 24 delivered into position within the yoke 22 without using the same tool and thereby avoiding having the closure cap 24 pushed to tightly onto the tip of the persuader 254.

Figure 50A:
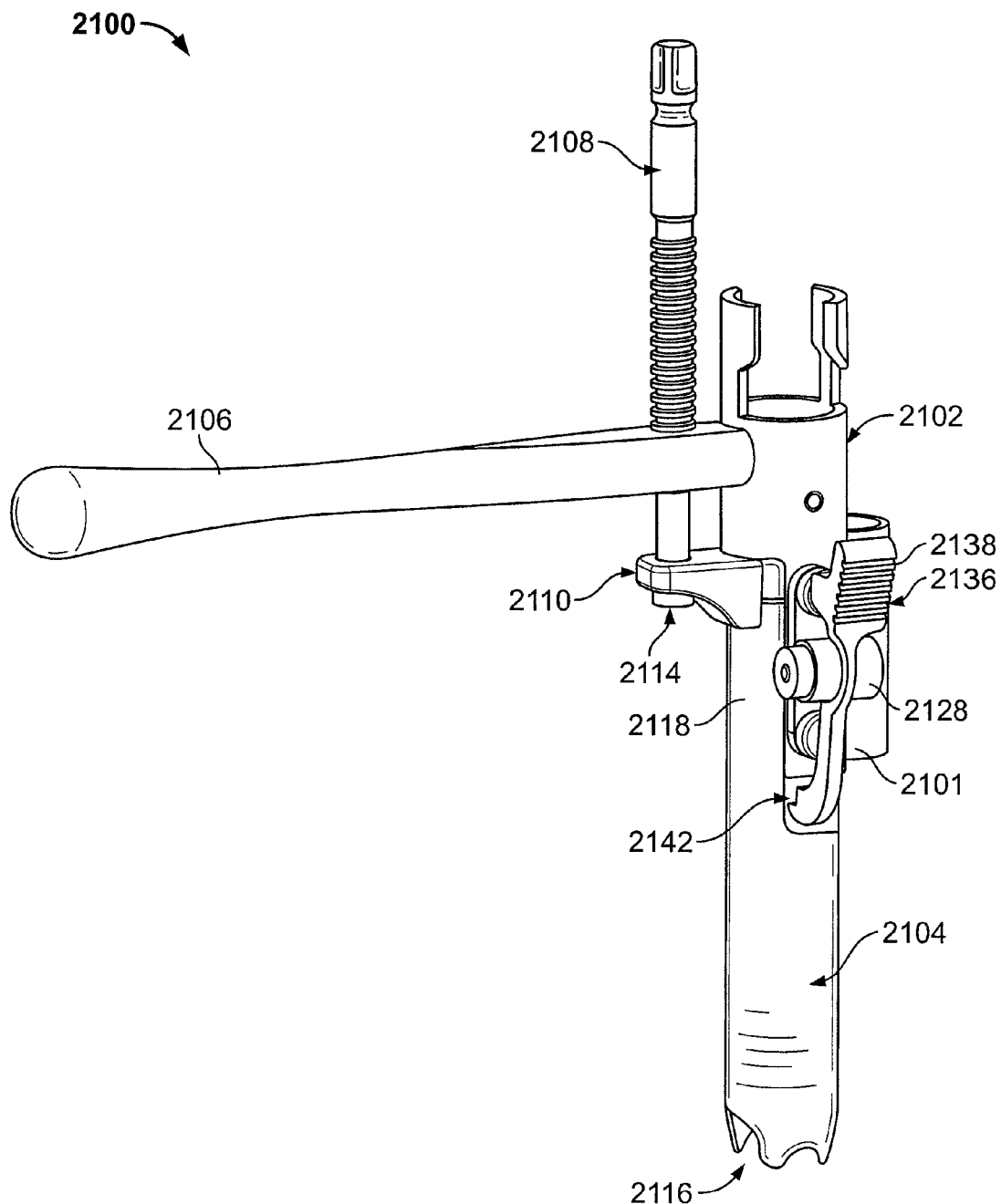
FIG. 50A is a perspective view of a convincing tool having a tool housing, a translation tube, and a latch for engaging the inner sleeve of the yoke manipulator of FIGS. 10-12.

As illustrated in FIG. 50A, the convincing tool 2100 includes a tool housing 2102, a translation tube 2104, a handle 2106, and a drive 2108 that rotatably is supported by a pivot housing 2110. The translation tube 2104 has a lower insertion end 2116 and an upper attachment end 2118 at which the pivot housing 2110 is attached. A shoulder bolt 2114 secures the drive 2108 to the housing 2110 as shown in FIG. 50C. The pivot housing 2110 is secured to the translation tube 2104 through a housing pin 2112. Since the drive 2108 is rotatably offset from the translation tube 2104, as shown in FIG. 50A, a slot 2120 allows the movement of the drive 2108 to be transferred to the translation tube 2104 and allows the pivot housing 2110 to ride upwards and downwards relative to the housing 2102.

Figure 50B:
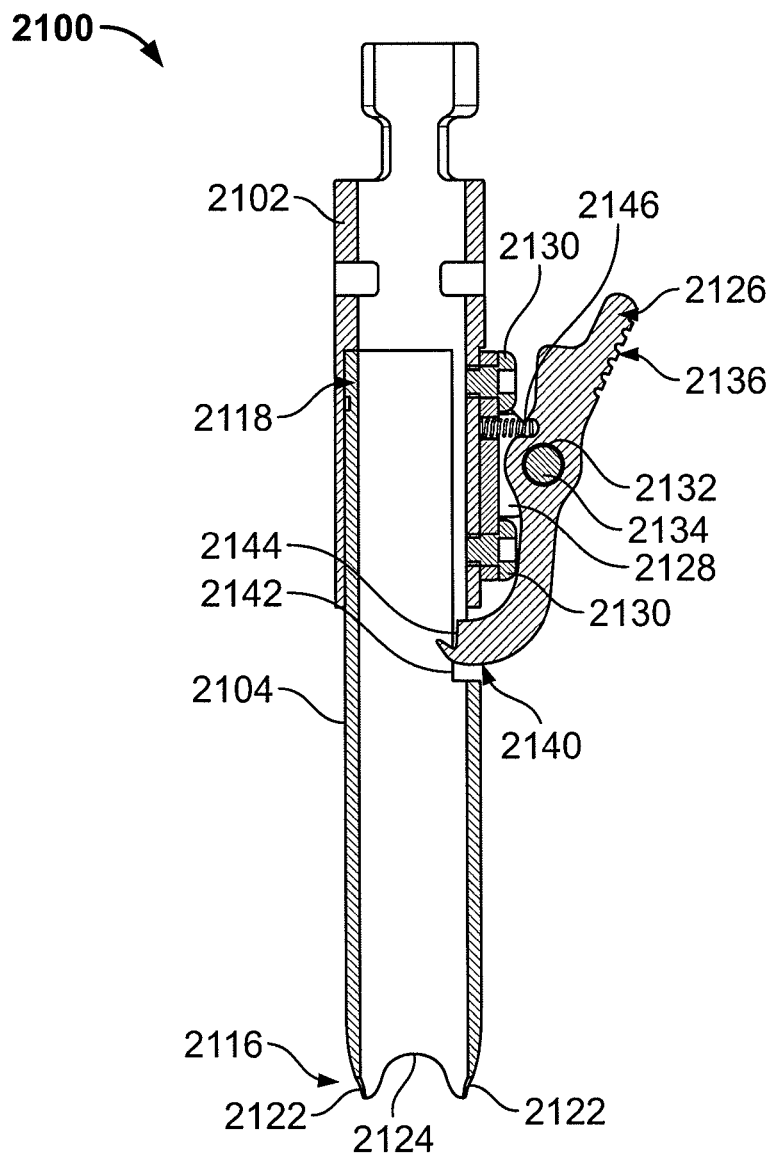
FIG. 50B is a cross-sectional view of the convincing tool of FIG. 50A taken along line B-B and showing the configuration of the tool housing, the driver, the rotatably offset translation tube, and the latch.
Figure 50C:
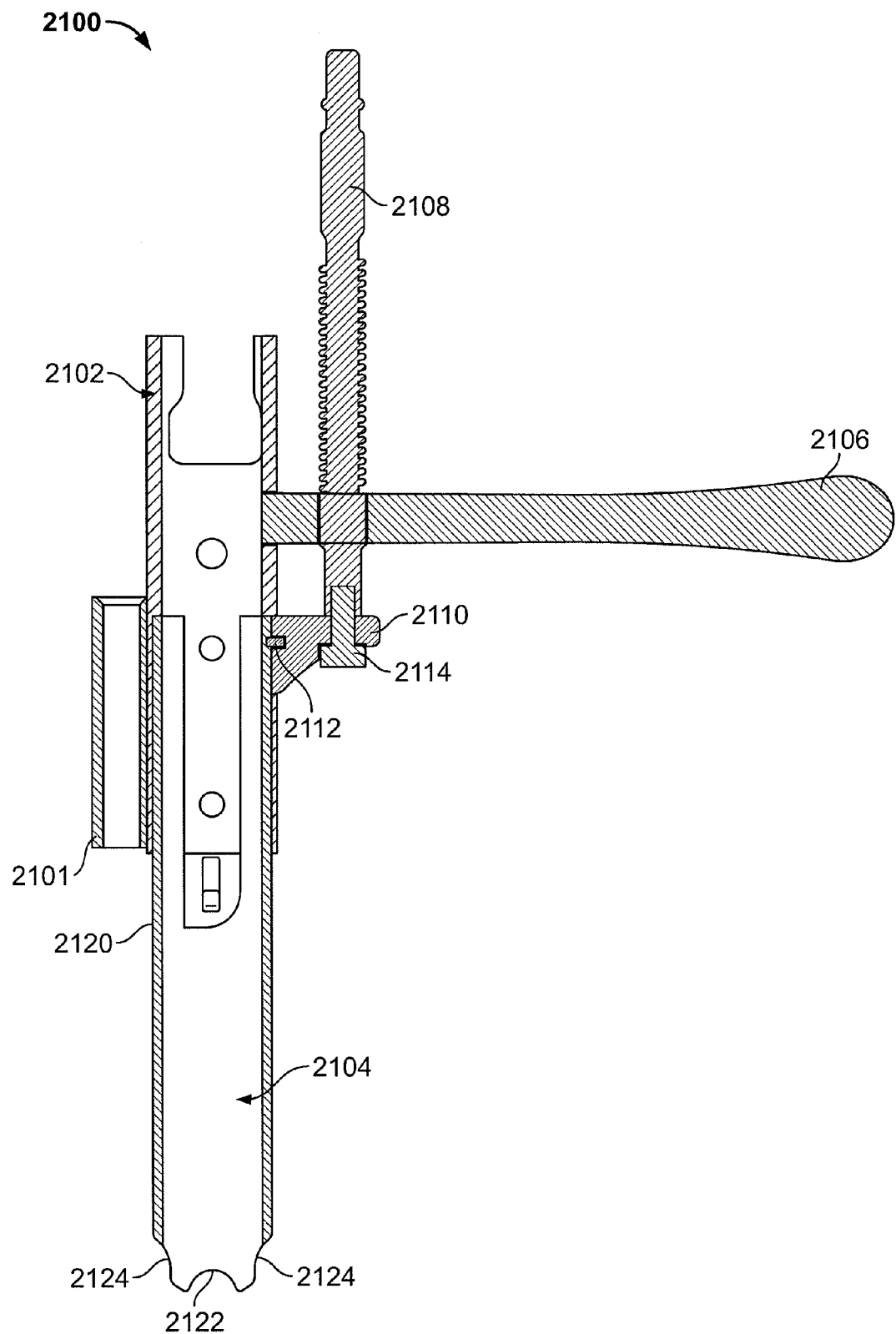
FIG. 50C is another cross-sectional view of the convincing tool of FIG. 50A showing the tool housing, the driver, and the rotatably offset translation tube, taken along line C-C.
Figure 50D:
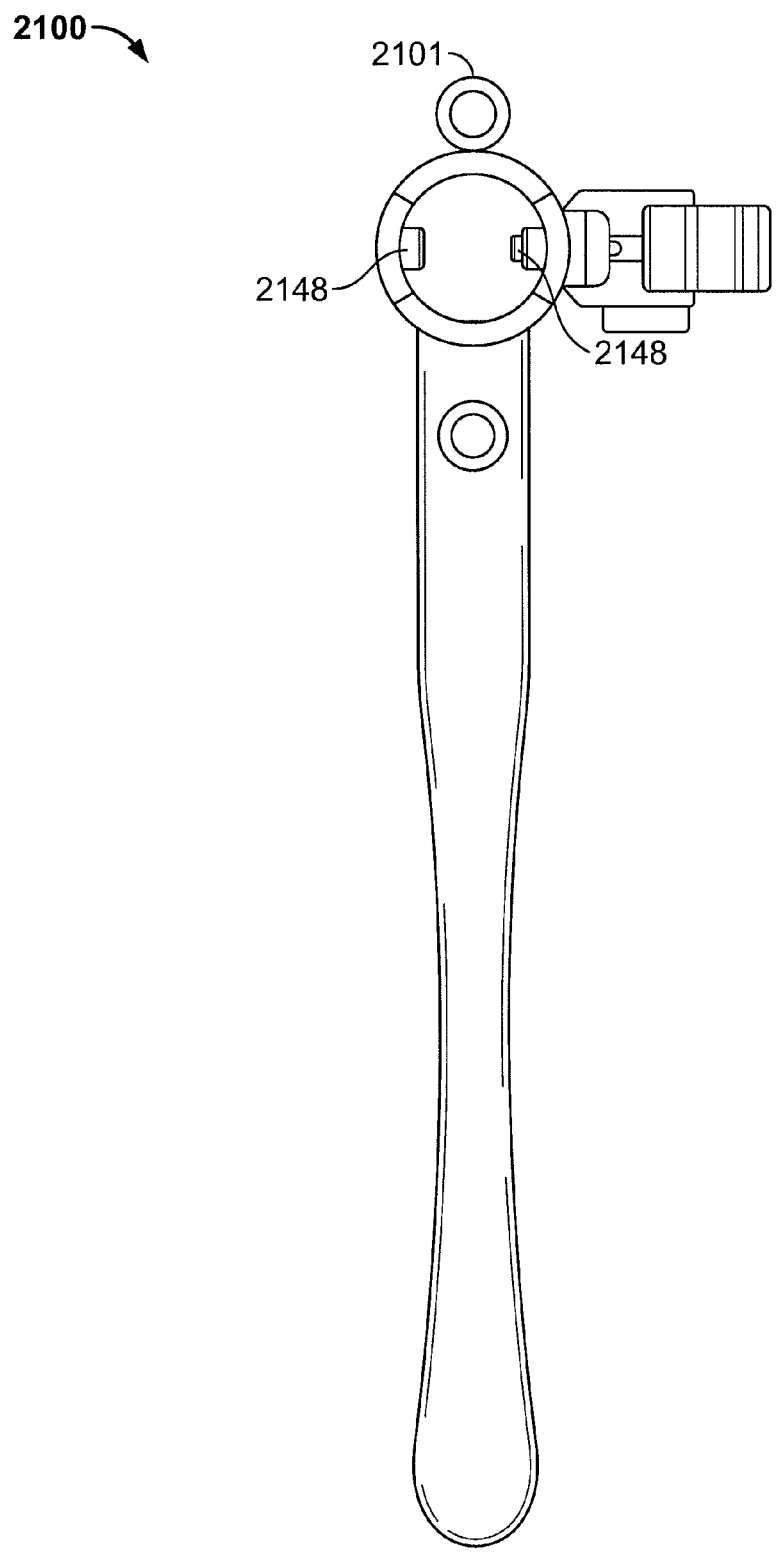
FIG. 50D is a top plan view of the convincing tool of FIG. 50A showing the tool housing, the handle, and the latch.
Figure 50E:
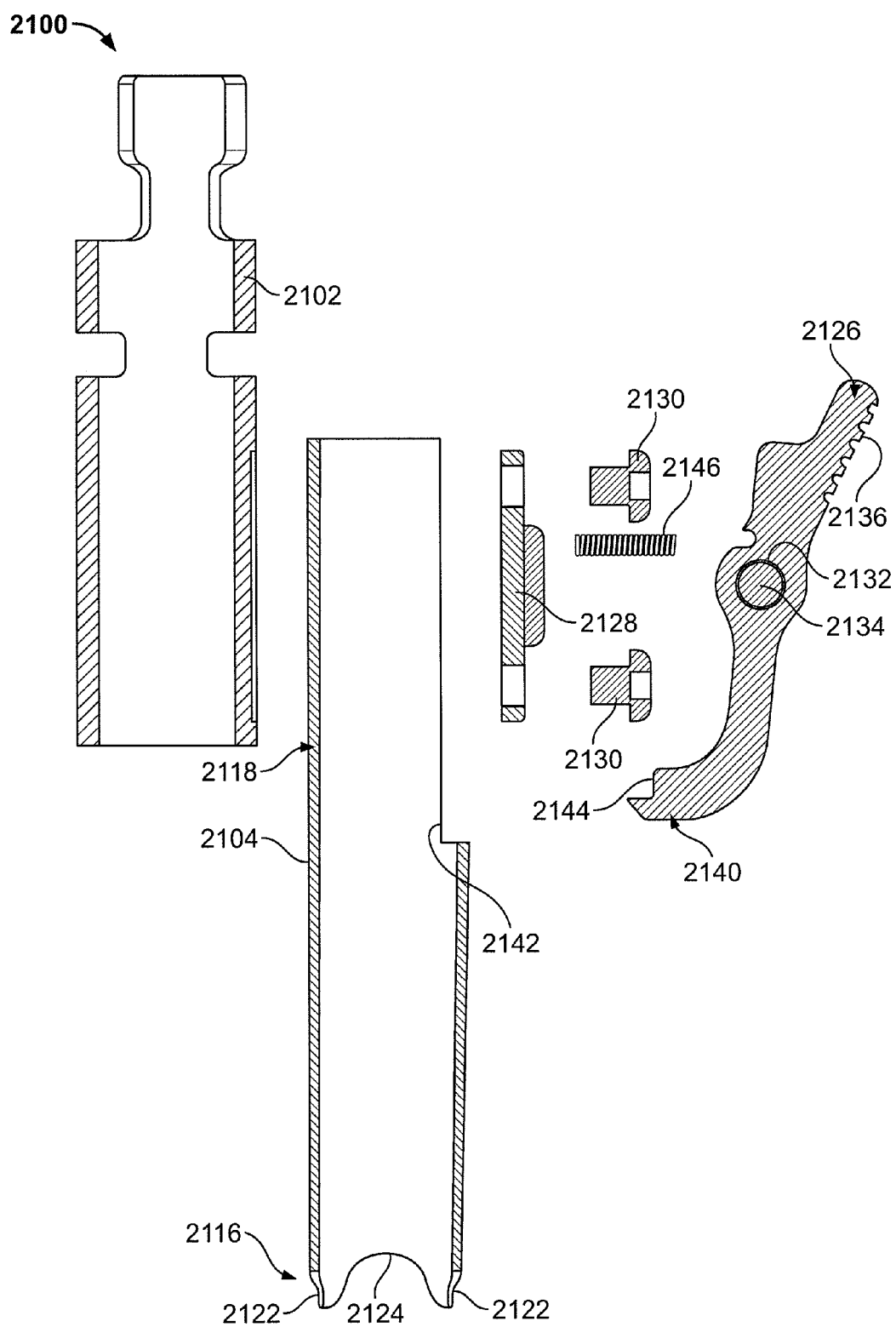
FIG. 50E is an exploded perspective view of the convincing tool of FIG. 50C.
Figure 50F:
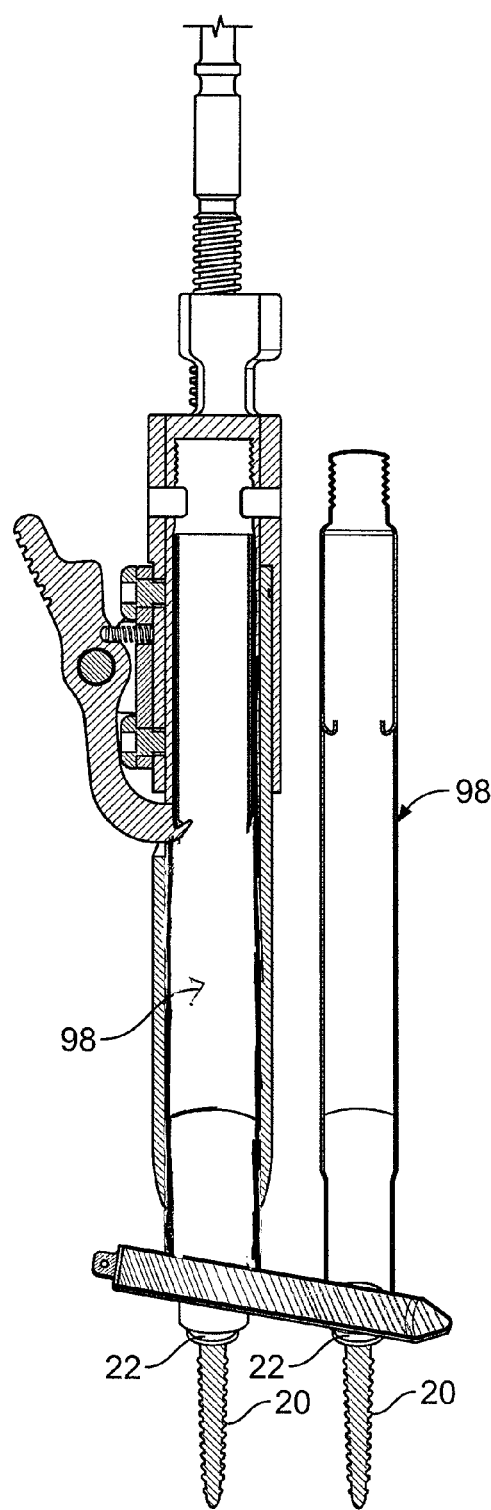
FIG. 50F is a side elevation view of the convincing tool of FIG. 50A, the yoke manipulators of FIGS. 7-12, the connecting member of FIG. 2, and the pedicle screw assemblies of FIG. 1 showing an initial stage rod positioning with the yokes.
Figure 50G:
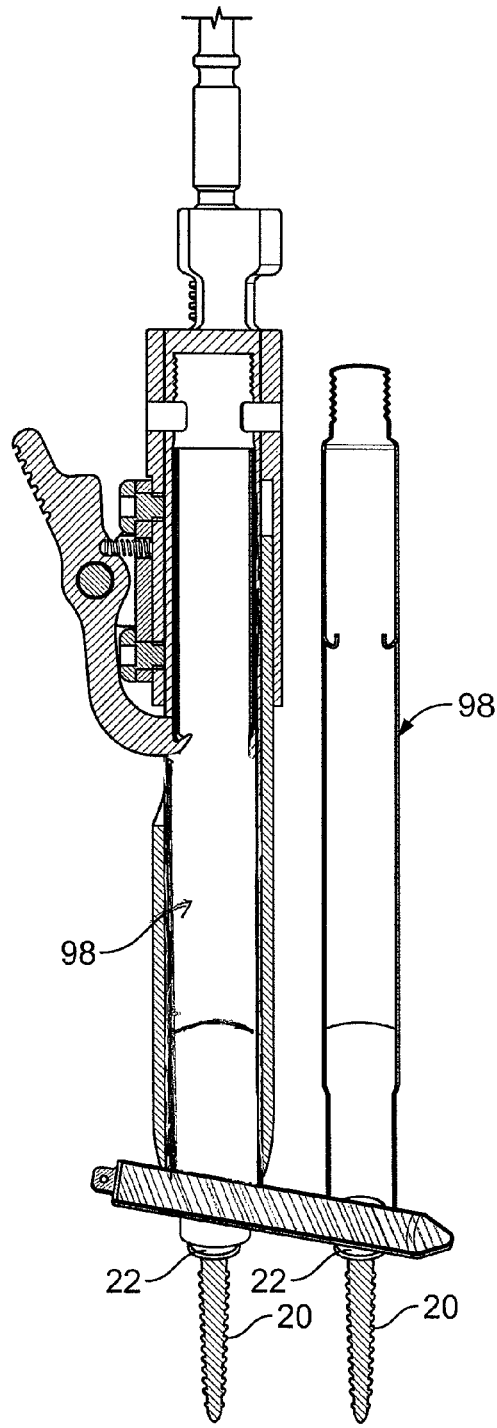
FIG. 50G is a side elevation view of the tools of FIG. 50F in an intermediate stage of rod positioning.
Figure 50H:
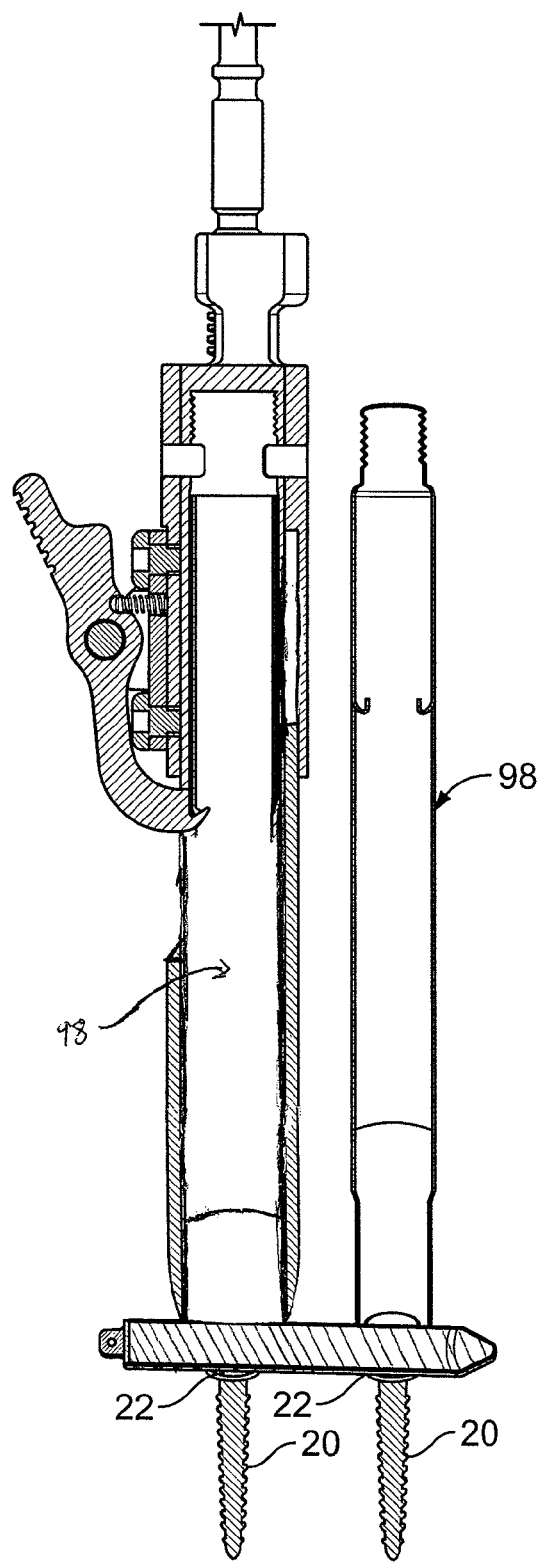
FIG. 50H is a side elevation view of the tools of FIG. 50F in a final stage of rod positioning.

To assist with seating the connecting member 26, the translation tube 2104 has opposing rod cutouts 2122 and opposing interference cutouts 2124 spaced ninety degrees from, the rod cutouts 2122 about the bottom 2116 of the tube 2104, as shown in FIGS. 50B and 50C. The rod cutouts 2122 are of a smaller size than the interference cutouts 2124. The rod cutouts 2122 are located transverse to the handle 2106. The rod cutouts 2122 are sized to engage the connecting member 26 and position the connecting member 26 into the yokes 22. As discussed below in greater detail, the convincing tool 2100 seats the connecting member 26 by pushing down on the member 26 while holding the yoke 22 against shifting by having the housing 2102 retain the yoke manipulator 98. The interference cutouts 2124 provide clearance between the translation tube 2104 and various portions of the spinal processes. The insertion end 2116 has a tapered configuration to ease insertion of the convincing tool 2100 into the surgical site.

The connecting member 26 is seated by having the translation tube 2104 push downward on the connecting member 26 while the tool housing 2102 keeps the yoke 22 vertically stationary. To seat the connecting member 26 into the yoke 22, the convincing tool 2100 not only pushes on the connecting member 26, but also attaches to the long slot 114 of the inner sleeve 100 yoke manipulator 98. By securing to the inner sleeve 100 of the yoke manipulator 98 to which the yoke 22 is mated, the yoke 22 is retained in position while the connecting member 26 is pushed downward and seated therein. Therefore, the connecting member 26 is pushed down relative to the yoke 22 via the yoke manipulator 98 by having the translation tube 2104 advanced into the wound by turning the driver 2108.

To secure to the inner sleeve 100 the tool housing 2102 of the convincing tool 2100 includes a latch 2126, as shown in FIGS. 50A-B. The latch 2126 secures to the long slot 114 of the yoke manipulator 98 while the translation tube 2104 pushes on the connecting member 26. Securing the tool housing 2102 via the latch 2126 to the yoke manipulator 98 allows the translation tube 2104 to move the connecting member 26 relative to the yoke manipulator 98 and the yoke 22. The latch 2126 pivots about a hinge 2128 that is attached to the housing 2102 by a pair of fasteners 2130, such as cap screws. The latch 2126 has an opening 2132 through which a pivot 2134, such as a shoulder screw, extends. In addition, the latch 2126 includes a finger tab 2136 with ribs 2138 for added friction. Opposite the finger tab 2136, the latch 2126 includes a toothed projection 2140 that extends through a slotted opening 2142 located in the translation tube 2104. The toothed projection 2140 includes a flat 2144 that provides clearance for the outer sleeve 102 of the yoke manipulator 98. Thus, since the toothed projection 2140 extends only a small distance past the flat 2144 that may engage the outer sleeve 102, the toothed projection 2140 will not extend significantly into the tubular opening of the yoke manipulator 98. Therefore, the convincing tool 2100 will not extend into the opening and interfere with the delivery of tools, devices, implants, or portions thereof that may be delivered down the center bore of the yoke manipulator 98, such as the closure cap 24. Instead, the toothed projection 2140 extends through the outer sleeve 102 and engages the long slot 114 of the inner sleeve 100, which is attached to the yoke 22, without excessively protruding past the inner sleeve 100.

As shown in FIG. 50B, the latch 2126 may have a curved geometry extending from the hinge structure 2128 in order to provide clearance for one of the fasteners 2130 and engage the tool with the inner sleeve 100 through the slotted opening 2142 that is located on the other side of the fastener 2130 from the pivot 2134. The convincing tool 2100 further includes a spring 2146 that biases the toothed projection 2140 into engagement with the inner sleeve 100 and simultaneously biases the finger portion 2136 outward from the housing 2102. Since the convincing tool 2100 grabs the inner sleeve 100 of the yoke manipulator 98 instead of the outer sleeve 102, the force does not have to be transferred to the inner sleeve by the spring 134. This creates a more robust attachment to the yoke 22 and lessens the chance the connection between the two sleeves may fail.

Figure 40:
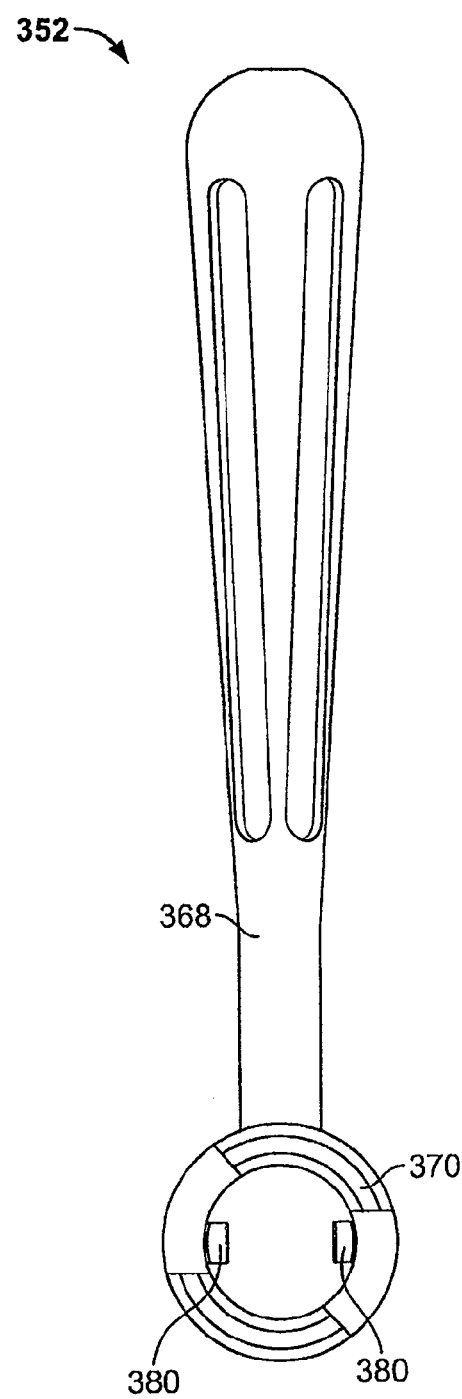
FIG. 40 is a top elevation view of the counter torque tube of FIG. 38, as configured in accordance with the various embodiments of the invention.

The convincer tool 2100 also includes two internal pins 2148 that extend into the tool housing 2102 and are slid down corresponding structure on the yoke manipulator 98 to keep the two tools aligned. The internal pins 2148 are similar to those located in the counter torque tube 352, as shown in FIG. 40. Proper tool alignment may assists with correct positioning of the cap 24 relative to the yoke 22 and misalignment of the cap 24 may prevent it from seating within the yoke 22. In addition, the convincer 2100 includes a side tube 2101 to be used for compression or distraction as discussed later.

Figure 51A:
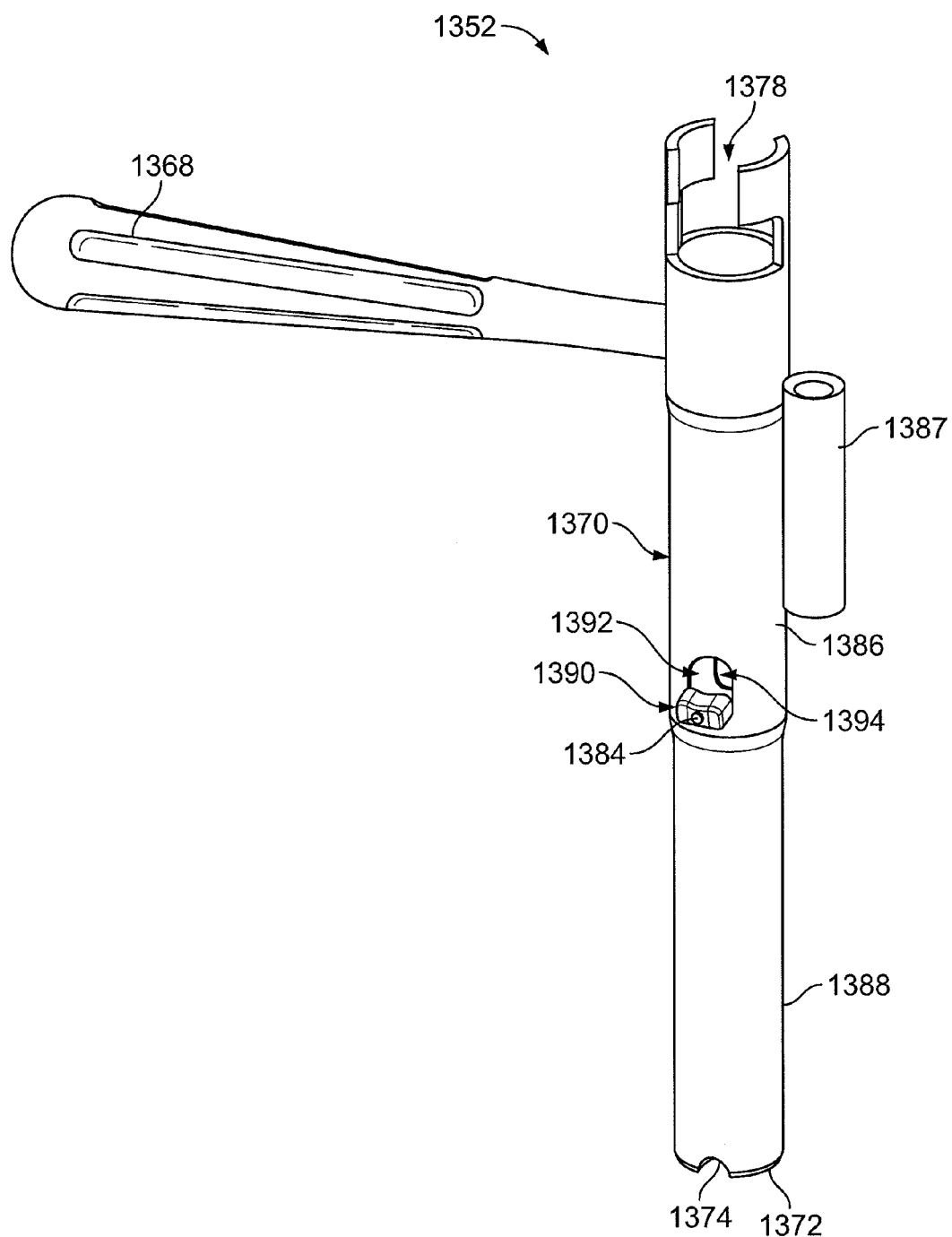
FIG. 51A is a perspective view of an alternative counter torque tube having a fulcrum and an opening for use in seating the connecting member.
Figure 51B:
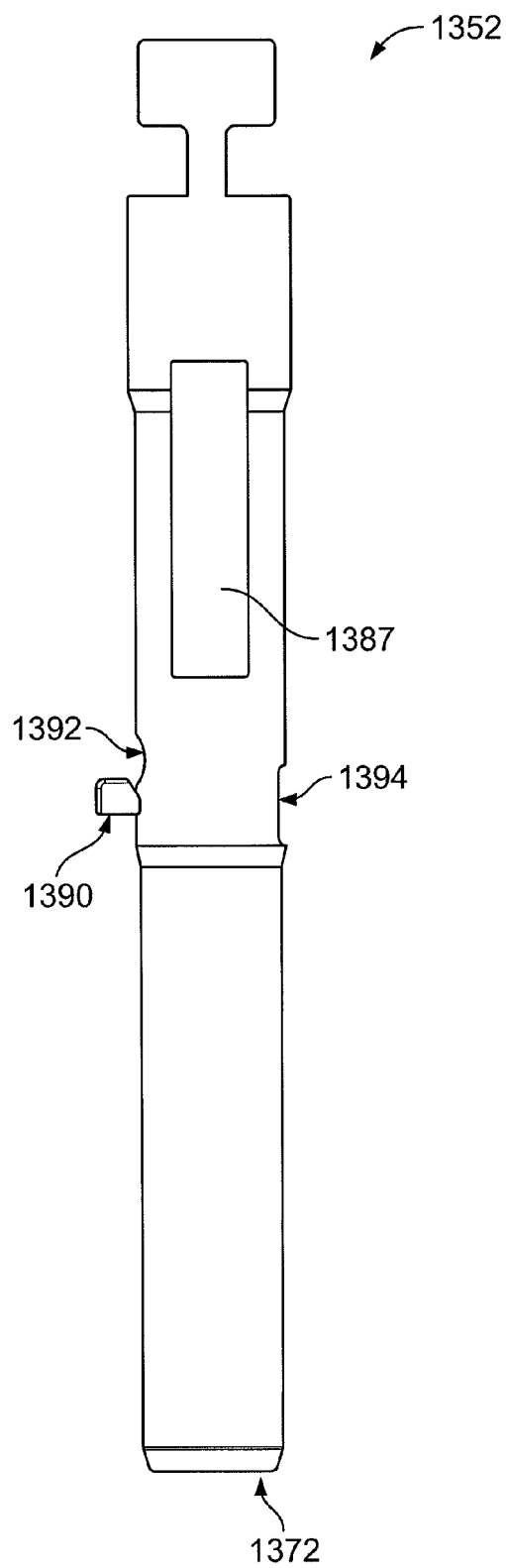
FIG. 51B is a side elevation view of the alternative counter torque tube of FIG. 51A.

Another alternative tool is the counter torque tube 1352 as shown in FIGS. 51A-B. Similar to counter torque tube 352, the counter torque tube 1352 is positioned around the yoke manipulator 98 and includes a handle 1368 and a body 1370. However, the counter torque tube 1352 is slightly longer than tube 352. The body 1370 has a larger diameter portion 1386 and a smaller diameter portion 1388. The smaller diameter portion 1388 is the lower portion of the tube 1352 and is the portion that is inserted into the wound. The smaller diameter portion 1388 extends to a tapered end 1372 that has curved cutouts 1374. The curved cutouts 1374 are sized so snugly engage the connecting member 26. In addition, the counter torque tube 1352 may include cutouts (not shown) to provide clearance from the various spinal structures. The counter torque tube 1352 also has connecting structure 1378 that limits the movement of the final locker 350, however, unlike connecting structure 378 of tube 352, the connecting structure 1378 allows for more rotation of the final locker 350 and therefore allows the surgeon to fully lock the closure cap 24. A pair of dowel pins 1380 also extends into the center of the counter torque tube 1352 and may be used to mate the counter torque tube 1352 with the yoke manipulator 98. The counter torque tube 1352 may also have a side tubes 1387 that allow the tool to be mated with the compression-distraction tool 1330 discussed below.

In one embodiment, the counter torque tube 1352 includes a fulcrum 1390 in the larger diameter portion 1386 just below an opening 1392. After the counter torque tube 1352 is seated atop the connecting member 26, a lever 1400, discussed in greater detail below, may be inserted through the opening 1392 and may engage the long slot 114 on the yoke manipulator 98. Then, the lever 1400 can be rotated around the fulcrum 1390 to move the long slot 114 and thus, the yoke manipulator 98, upwards. By pulling upwards on the yoke manipulator 98, the yoke 22 is pulled upward while the connecting member 26 is being pushed downward by the tapered end 1372 of the counter torque tube 1352 helps seat the connecting member 26 and may be useful if the surgeon encounters soft tissue that prevents the member 26 from seating in the yokes 22.

The fulcrum 1390 includes middle indentation 1396 having geometry to guide the lever 1400 to the opening 1392. The fulcrum 1390 has a sloped portion 1398 on the side adjacent the counter torque tube 1352. The opening 1392 of the counter torque tube 1352 is located slightly lower than upper surface of the fulcrum. Thus, a shoulder or ledge 1399 is created on the fulcrum 1390 since the opening 1392 extends below the upper surface of the fulcrum. The ledge 1399 allows the lever 1400 to pivot above the bottom of the opening 1392 and this positioning allows the surgeon to provide more force to reduce the connecting member 26 into the yoke 22. In addition, the fulcrum 1390 includes a through opening 1382 which may accommodate a pin 1384 that attaches the fulcrum 1390 to the body 1370 of the counter torque tube 1352.

The counter torque tube 1352 further includes an opening 1394 located opposing opening 1392 and fulcrum 1390. The opening 1394 may accommodate the fulcrum 1390 of an adjacent counter torque tube 1352. Thus, the opening 1394 is slightly lower relative to opening 1392 to accept the fulcrum 1390, which sits below opening 1392 of an adjacent tube 1352. In one preferred embodiment, the surgeon will employ one counter torque tube 1352 for each bone anchor 20 implanted into the patient. If the connecting member 26 is relatively short and the compression-distraction tool 1330 is used to shorten the distance between the bone anchors 20, the fulcrum 1390 may abut adjacent counter torque tubes 1352. Thus, by adding an opening 1394, one counter torque tube 1352 has clearance for an adjacent tube 1352. Thus, the opening 1394 allows the compression-distraction tool 1330 to be used to adjust the bone anchors 20 more closely to one another with interference of the fulcrum with the body 1370.

Once the counter torque tube 1352 and the lever 1400 are used to seat the connecting member 26, the tools can remain in position while the closure cap 24 is seated. Since the counter torque tube 1352 allows the surgeon to overcome the soft tissue positioned around the implant, the counter torque tube 1352 should not be removed from the system until after the connecting member 26 and closure cap 24 have been secured into position.

Figure 52:
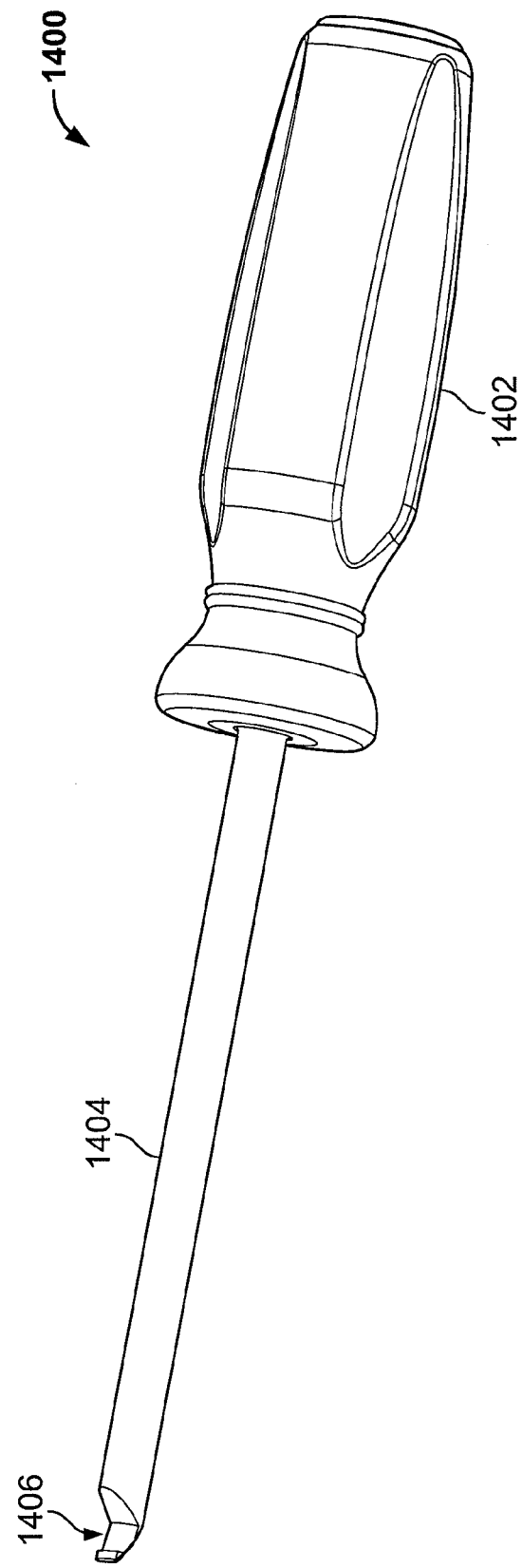
FIG. 52 is a perspective view of a lever for use with the counter torque tube of FIG. 51A to use with the fulcrum to seat the connecting member.

As shown in FIG. 52, the lever 1400 has a handle 1402 with a rod 1404 attached thereto. The rod 1404 had a hook-shaped end 1406 that is able to pass through the opening 1392 of the counter torque tube 1352 to engage the yoke manipulator 98. The hook-shaped end 1406 is sized with a tapered geometry such that the tip fits easily within the opening 1392. In one preferred embodiment, the closure cap 24 will be inserted through the yoke manipulator 98 and then the lever 1400 will be employed such that the portion of the lever 1400 that extends into the central opening of the yoke manipulator 98 will not interfere with the delivery of the closure cap 24.

Figure 53:
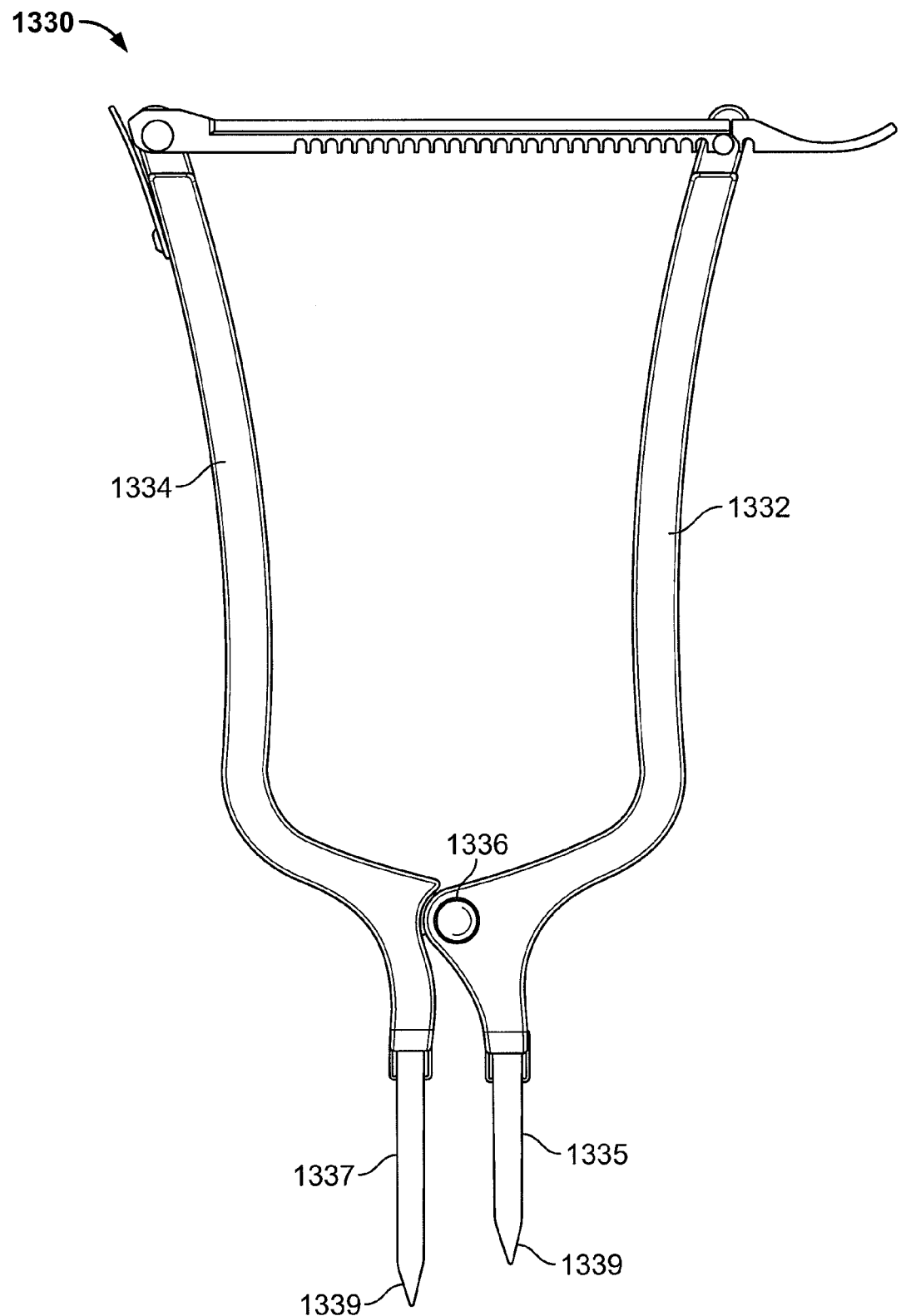
FIG. 53 is a front elevation view of an alternative compression-distraction tool for use in adjusting the distance between vertebrae.

As discussed above, the surgeon can compress or distract the position of the bone anchors 20 to adjust the distance between the vertebrae. The compressor-distraction tool 1330, similar to tool 330, includes two handles 1332 and 1334 connected together by pivot pin 1336. As shown in FIG. 53, the arms or handles 1332, 1334 are slightly longer than those of tool 330. The longer handles 1332, 1334 provide additional mechanical advantage. Instead of engagement arms 338 as employed by the tool 330 shown in FIG. 36, the handles 1332, 1334 attach to pins 1335, 1337. The arms 338 engaged flats located on the various MIS tools while the pins 1335, 1337 engage sleeves on the sides of the various MIS tools. The pin 1335 is slightly shorter than the pin 1337 to accommodate their insertion into openings one at a time. The pins 1335, 1337 further include tapered tips 1339 also provide for easier insertion. Since in one preferred embodiment, the connecting members 26 are pre-bent to a radius of 7 inches, the center pivot point of the tool 1330 is 7 inches away from the connecting member 26 to avoid a binding effect. The compression-distraction tool 1330 may be used with the convincing tool 2100 and the counter torque tube 1352.

Another tool a surgeon may desire to incorporate into the MIS procedure is the tissue dilation tool disclosed in U.S. Provisional Patent Application No. 60/813,628 filed on Aug. 22, 2006 and hereby incorporated by reference. Such a tool may be employed to stretch the tissue around an initial incision. This way a smaller incision can be maximized to accommodate larger various tooling and implants without requiring a larger incision by stretching the tissue.

In addition to the minimally invasive surgical procedure described herein, many of the described tools are used in a procedure that may require the surgeon to increase the size of the opening into the patient beyond what is normally considered a minimally invasive procedure. While the MIS system uses a stab wound opening to insert each bone anchor 20 and closure caps 24 and also uses one of those openings to insert the connecting member 26, the mini-open procedure has an opening that extends the distance between where the bone anchors 20 are seated. During a typical MIS procedure, a relatively small incision is made at the surgical side through which the pedicle screw assemblies 21 and connecting member 26 are advanced. A confined guideway created by the incision allows that delivery of the implant with the view of the implant site being obstructed. The mini-open procedure preferably uses a retractor to stretch the wound to accommodate various tools. While MIS system is the least invasive procedure, the full open procedure can be the most invasive and requires that the wound be sized large enough to accommodate the procedure without relying on the tissue dilators or retractors. Since the mini-open procedure provides the surgeon less space to operate than the full open, the tools are configured to avoid having to fully open the surgical wound. Such a slit opening in a mini-open surgery may be used based on the patient's anatomy or surgeon preferences.

Figure 54A:
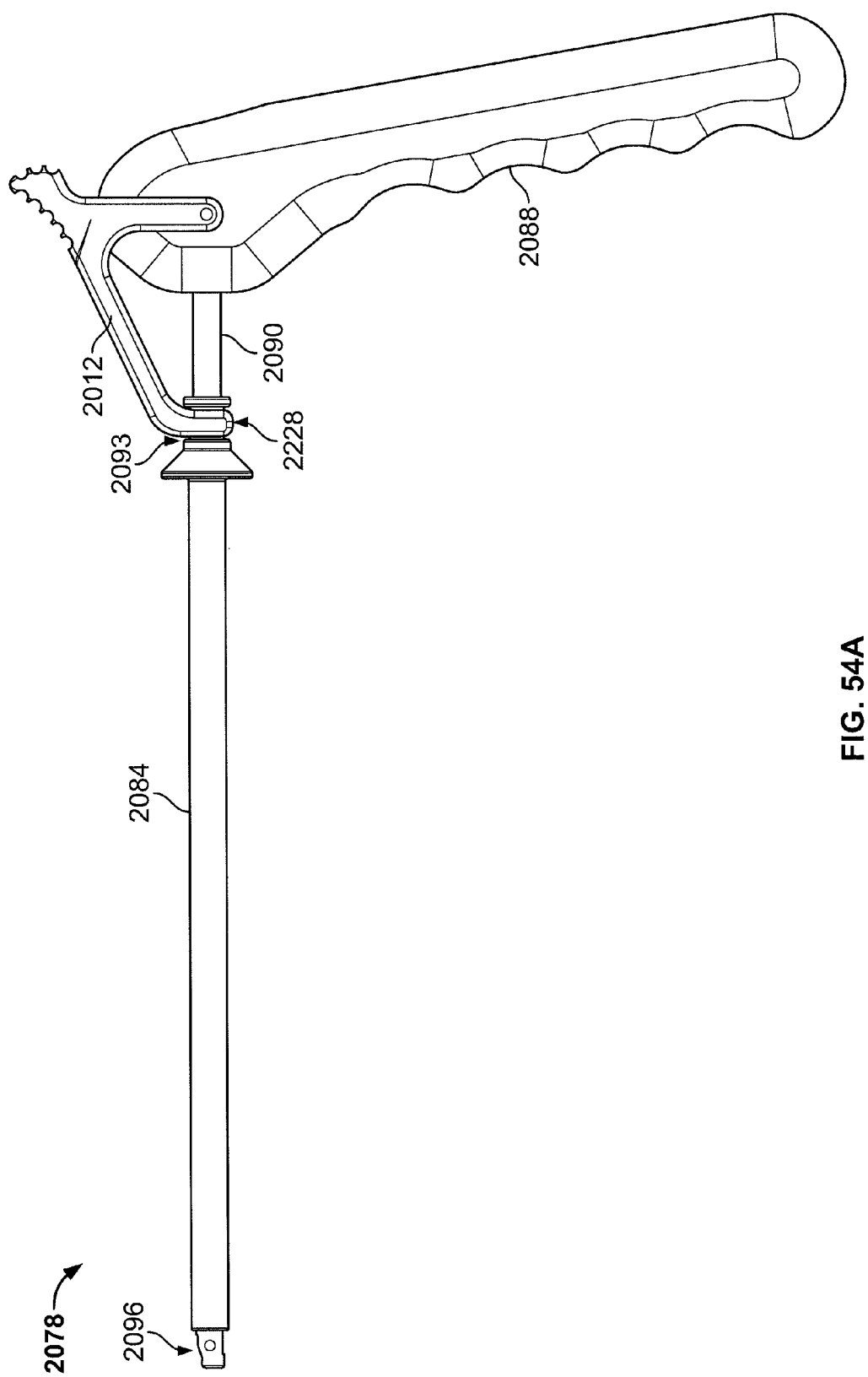
FIG. 54A is a side elevation view of an alternative rod inserter for use in a minimally open procedure to position the spinal rod within the pedicle screw assemblies.

In a mini-open procedure, a rod inserter 2078 may be used to seat the connecting member 26 as illustrated in FIG. 54A. Unlike the rod inserters 178 and 1078, the connecting member 26 can only be configured two ways relative to the inserter 2078: secured such that the connecting member is approximately 100° relative to the inner shaft 2090 and disengaged such that the rod inserter 2078 may be removed from the surgical site after rod insertion. The attachment end 2096 is configured to secure the member 26 approximately 90-100° relative to the shaft 2090 and locking sleeve 2094 such that the tip 180 of the connecting member 26 slightly lower than the attachment end 184 during the insertion procedure. The attachment end 2096 is also configure to either secure the member 26 to the inserter 2078 or to release the member 26, unlike inserters 178 and 1078 that have an articulating position such that the member 26 may rotate relative to the inserters 178, 1078.

Figure 54B:
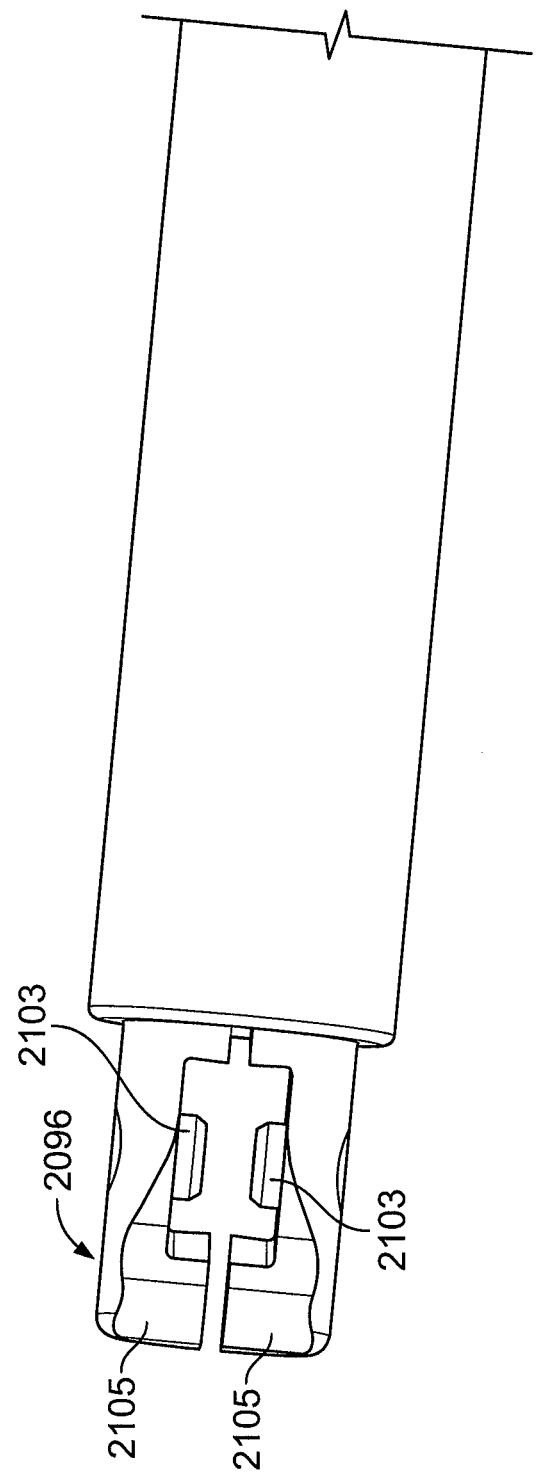
FIG. 54B is a perspective view of an end portion of the alternative rod inserter of FIG. 54A showing the structure for connecting the spinal rod to the rod inserter.
Figure 54C:
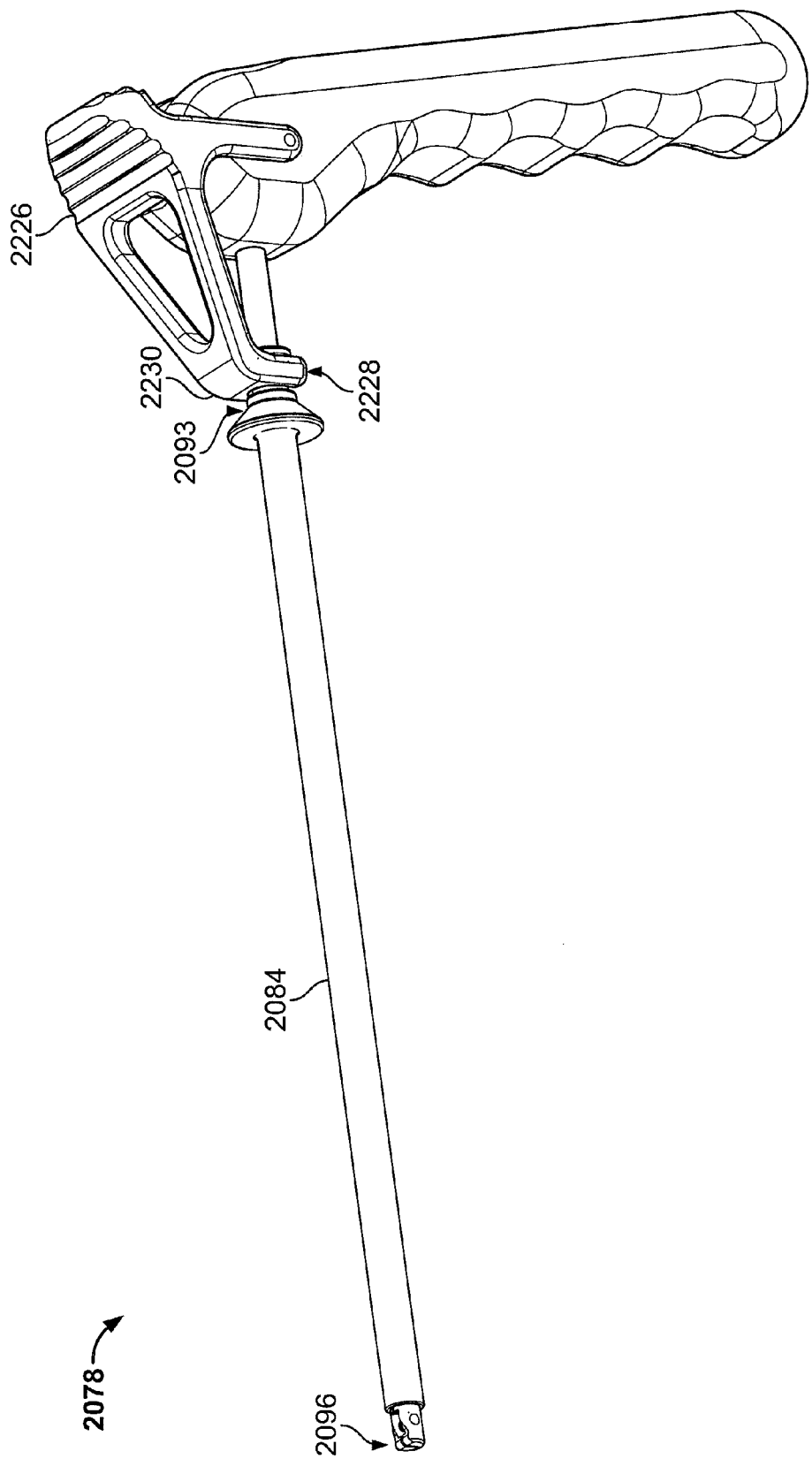
FIG. 54C is a perspective view of the alternative rod inserter of FIG. 54A.
Figure 54D:
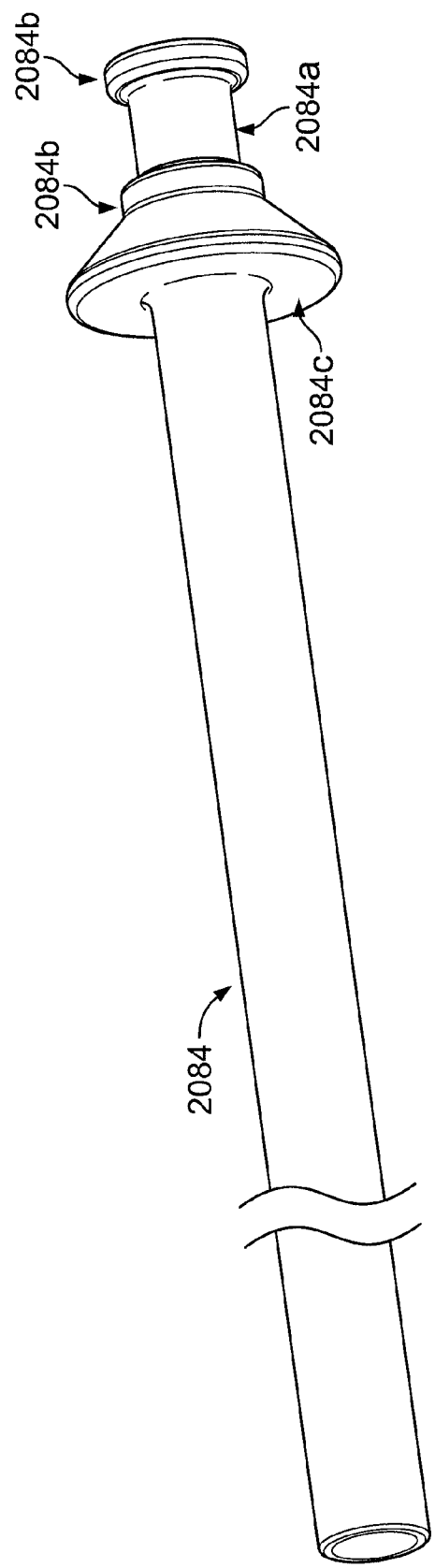
FIG. 54D is a perspective view of a locking sleeve of the alternative rod inserter of FIG. 54A.

As shown in FIG. 54A-C, the rod inserter 2078 includes a handle 2088, a latch 2102, inner shaft 2090, and a locking sleeve 2084. However, instead of a shift assembly the locking sleeve 2084 has a connecting structure 2093 that engages the latch 2102. The rod inserter 2078 having only two relative positions does not require a mechanism to shift the tool from a variety of configurations. The inner shaft 2090 includes an attachment end 2096 having two prongs 2105. The prongs 2105 have connecting pins 2103 that can mate with corresponding structures on the connecting member 26 to secure the two relative to each other. The latch 2102 includes a stopper 2228 with a u-shaped portion 2230. When the latch 2102 is in the safety position as described above, the u-shaped portion engages a recess 2084a located on the locking sleeve 2084. The recess 2084a has two raised portions 2084b on either side. The locking sleeve 2084 also includes an expanded portion 2084c that may be easily engaged by the fore finger and middle finger. After the connecting member 26 has been positioned between the yokes 22, a finger portion 2226 of the latch 2102 may be engaged to shift the latch 2102 to the disengaged position. Then, the expanded portion 2084c of the locking sleeve 2084 may be engaged to pull the locking sleeve 2084 back and allow the attachment end 2096 to disengage from the connecting member 26.

Figure 55:
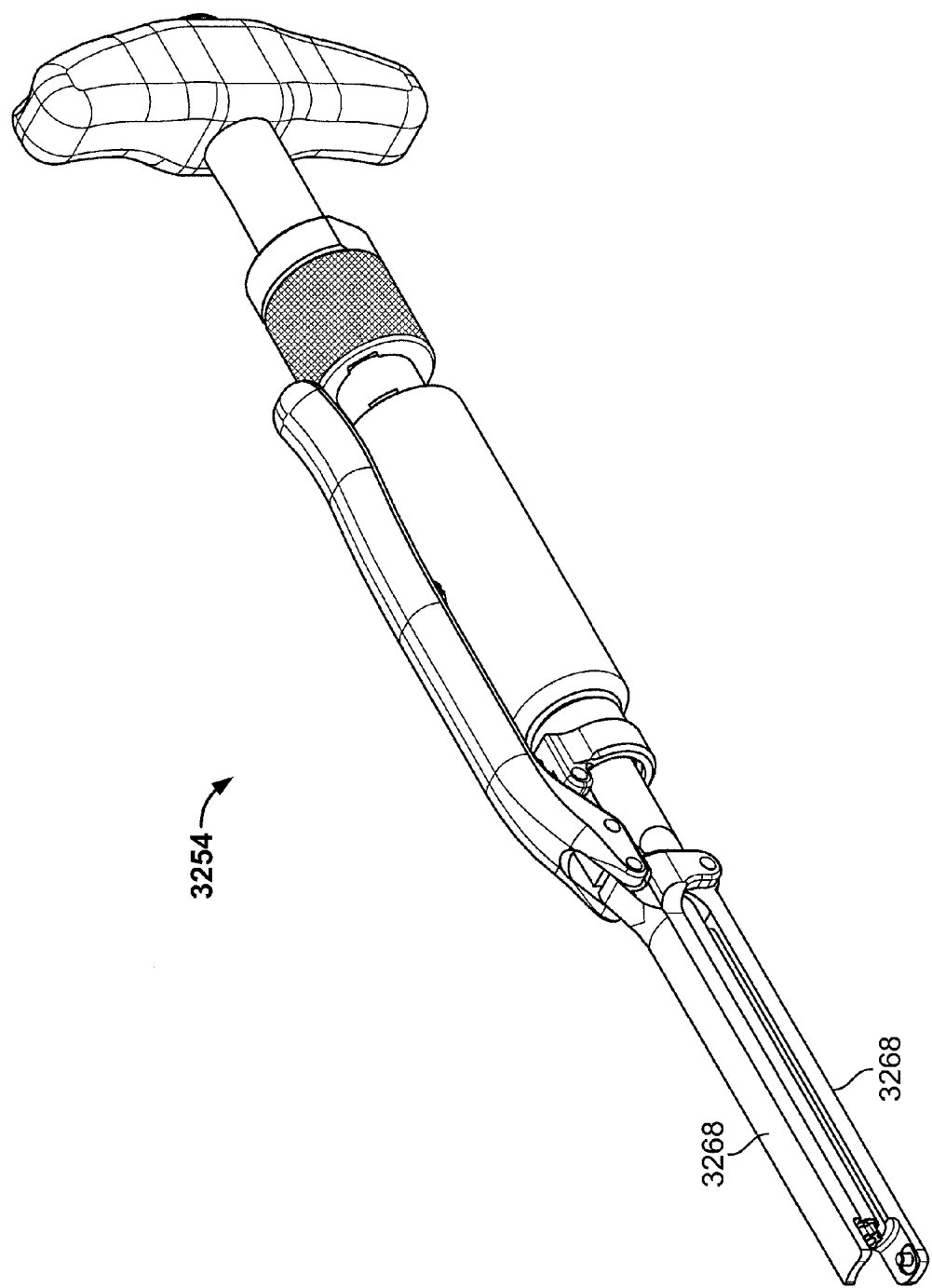
FIG. 55 is a perspective view of an alternative rod persuader for use in urging the spinal rod into the yoke and for securing the cap to the yoke.

For the mini-open procedure, a rod persuader 254 similar to the persuader tool disclosed in U.S. Provisional Patent Application No. 60/889,494, filed on Feb. 12, 2007 and U.S. patent application Ser. No. 10/973,659, filed Oct. 26, 2004, both of which are herein incorporated by reference, may be used to insert the closure cap 24 and seat the connecting member 26 sufficiently in the yokes 22. FIG. 55 illustrates an example of such a rod persuader. However, in one preferred embodiment, the jaw arms or prongs 3268 are longer to accommodate delivery of the closure cap 24 to the yoke 22 in a mini-open procedure. The longer arms 3268 allow for more clearance with the retractor that is often used in mini-open procedures.

Figure 56A:
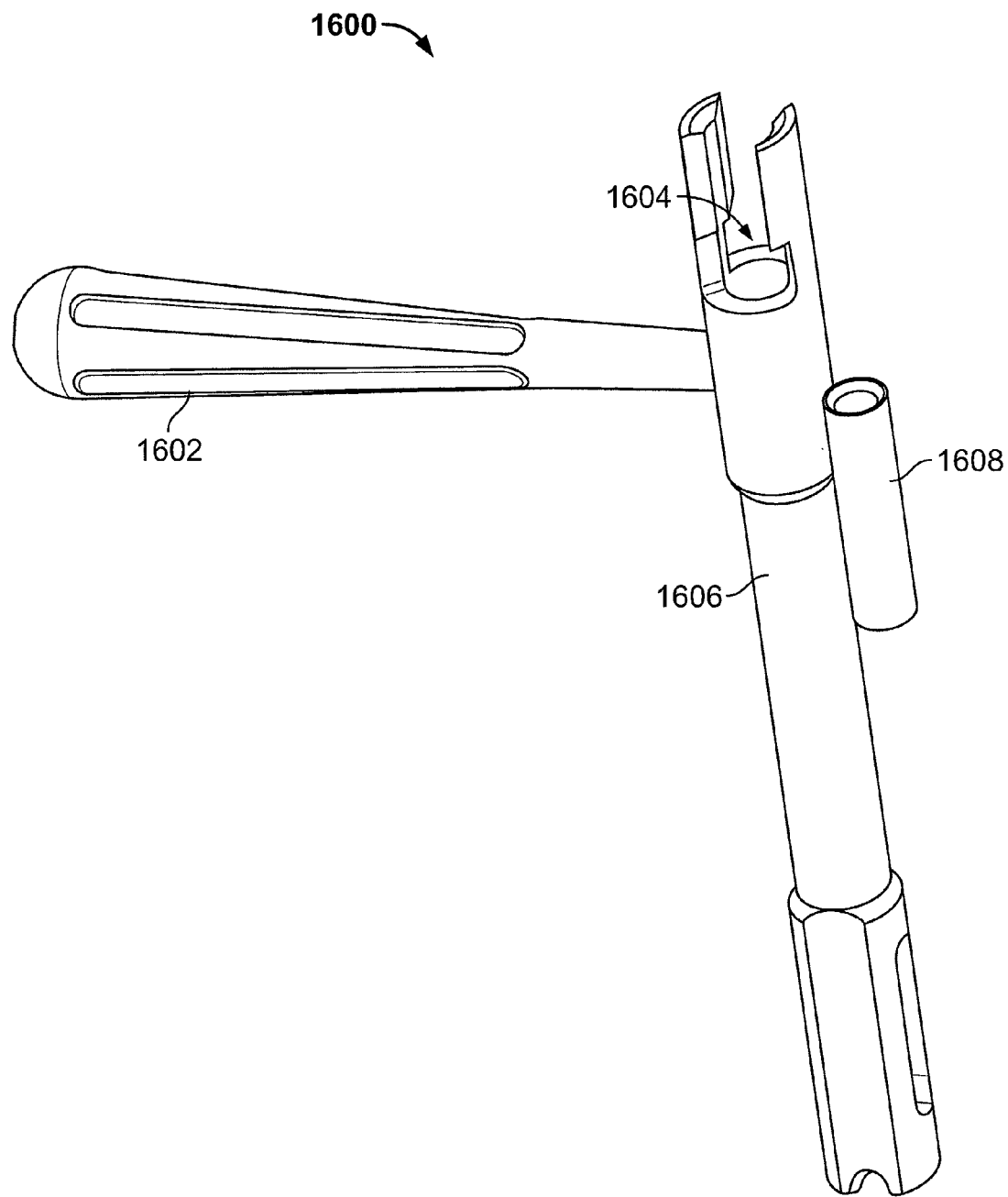
FIG. 56A is a perspective view of a stabilization tube for use during insertion of the cap.
Figure 56B:
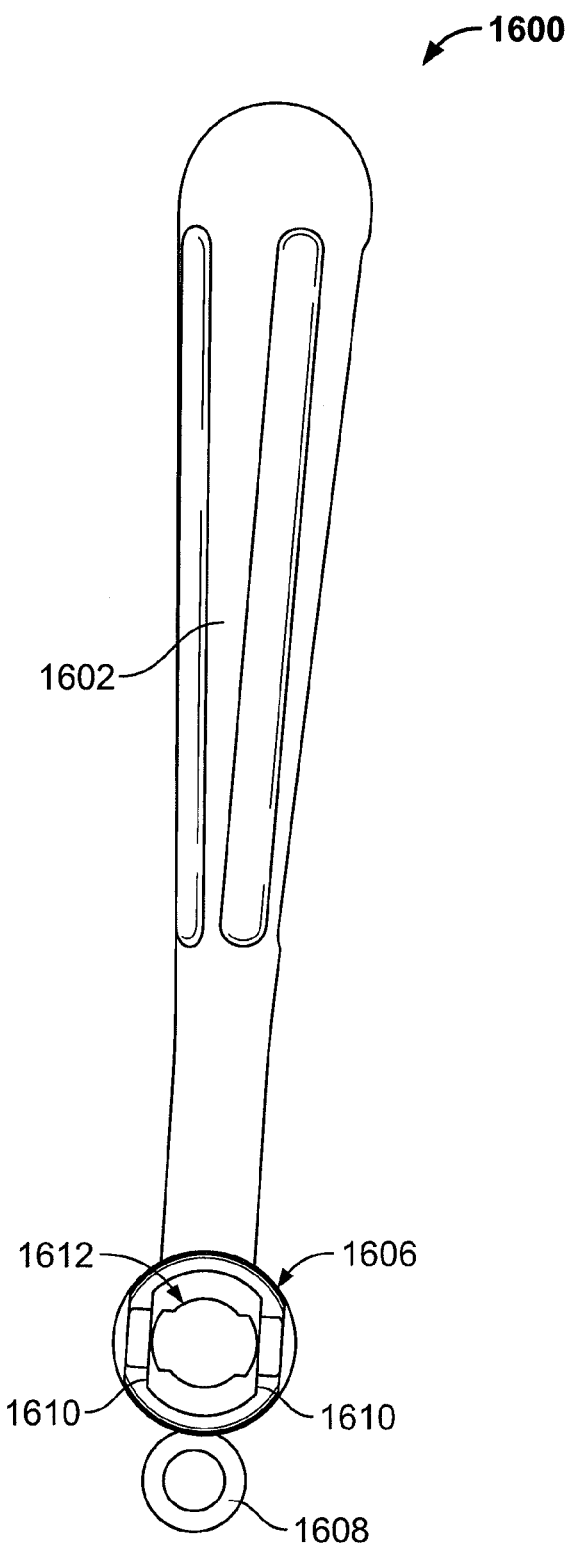
FIG. 56B is a bottom plan view of the stabilization tube of FIG. 56B showing the internal geometry of the stabilization tube.

Another tool that may be used in a mini-open procedure is the stabilization tube 1600, as shown in FIGS. 56A-B. The stabilization tool 1600, like the counter torque tube 1352, may include a handle 1602, connecting structure 1604, a shaft 1606 and a side tube 1608 to mate with the compression-distraction tool 1330. However, the stabilization tool 1600 is narrower than the counter torque tube because in the mini-open procedure, the yoke manipulator 98 is not employed or has been removed at this stage. Since the opening spans the distance between the bone anchors 20, the surgeon does not have to struggle with soft tissue that might prevent the connecting member 26 from seating within the yokes 22. Thus, the stabilization tube 1600 is employed to retain the yoke 22. To retain the yoke 22, the inner geometry of the stabilization tube 1600 includes flats 1610 that retain two sides of the yoke 22. In addition, it is contemplated that the inner geometry 1612 will include structure corresponding to the cross-section of the closure cap 24 so that the cap 24 is properly oriented during delivered into the yoke 22. However, such inner geometry may not be necessary depending on what tools are used to deliver the closure cap 24 into the yoke 22.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

The invention claimed is:

1. A minimally invasive surgical system comprising:
a pedicle screw assembly for being connected to a vertebral bone;
a coupling member of the pedicle screw assembly for receiving a spinal rod therein;
a tubular member adapted to releasably engage the coupling member of the pedicle screw assembly and having a sidewall and an opening extending through the sidewall;
a sleeve having an annular wall configured to slide over the tubular member and contact the spinal rod;
a fulcrum of the sleeve extending radially outward from the sleeve annular wall;
an aperture extending through the sleeve annular wall adjacent the fulcrum and being oriented to allow the sleeve aperture to be at least partially aligned with the tubular member opening when the sleeve is positioned over the tubular member;
a lever tool having a distal end portion adapted to fit through the sleeve aperture and at least partially into the tubular member opening to engage the tubular member sidewall adjacent the opening, an intermediate portion adapted to be supported by the fulcrum, and a proximal end portion for applying a force to the lever tool and pivoting the lever tool about the fulcrum for urging the sleeve and spinal rod toward the pedicle screw assembly.

2. The minimally invasive surgical system of claim 1, wherein the lever tool creates a moment arm between the distal end portion and the intermediate portion supported by the fulcrum to translate pivotal movement of the lever tool about the fulcrum into translational movement of the sleeve relative to the tubular member for urging the sleeve and spinal rod toward the pedicle screw assembly.

3. The minimally invasive surgical system of claim 1, wherein the fulcrum includes a ledge above a lower end of the sleeve aperture that permits the lever tool to pivot about a point elevated from the lower end of the sleeve aperture.

4. The minimally invasive surgical system of claim 1, wherein the distal end portion of the lever tool includes at least one surface configured to engage a portion of the sidewall of the tubular member adjacent the opening in the tubular member.

5. The minimally invasive surgical system of claim 1, wherein the fulcrum includes a depression for guiding the distal end portion of the lever tool through the sleeve aperture and at least partially into the tubular member opening.

6. The minimally invasive surgical system of claim 1, wherein the sleeve includes an opening sized to accommodate the fulcrum of an adjacent sleeve when the two sleeves are drawn into close proximity with each other.

7. A minimally invasive surgical system for seating a spinal rod into a pedicle screw assembly fastened to a vertebral bone, the system comprising:
a tubular member adapted to releasably engage the pedicle screw assembly and having a sidewall and an aperture extending through the sidewall;
a sleeve configured to slide over the tubular member and contact the spinal rod, the sleeve having a fulcrum positioned on an exterior of the sleeve and an aperture alignable with the tubular member aperture when the sleeve is positioned over the tubular member;
a lever tool having an end portion adapted to fit through the sleeve aperture and at least partially into the tubular member aperture and an intermediate portion adapted to abut the fulcrum for urging the sleeve and spinal rod toward the pedicle screw assembly;
a first receiving member positioned on the exterior of the sleeve;
a second tubular member adapted to releasably engage a second pedicle screw assembly fastened to a second vertebral bone;
a second receiving member connected to the exterior of the second tubular member; and
a tool having two moveable pins each on a pair of pivotably connected arms and sized to fit within the receiving members for moving the tubular members relative to each other a distance proportional to a user input when the pins are inserted into the receiving members permitting manipulation of the vertebral bones without projecting into the tubular members.

8. A minimally invasive surgical system comprising:
a pedicle screw assembly for being connected to a vertebral bone;
a coupling member of the pedicle screw assembly for receiving a spinal rod therein;
a tubular member having a longitudinally extending passage and an outer wall with an opening extending through the outer wall, the tubular member configured to be releasably engageable to the coupling member of the pedicle screw assembly;
a first tool having an elongate shaft and a distal end portion thereof configured to be connected to a locking device of the pedicle screw assembly for advancing the locking device through the tubular member passage and into the coupling member;
a sleeve sized to be positioned around the tubular member, the sleeve having a lower end portion for contacting the spinal rod and an aperture alignable with the tubular member opening when the sleeve is positioned around the tubular member;
a second tool having a distal end portion sized and configured to be inserted through the sleeve aperture and the tubular member opening when the sleeve aperture and the tubular member opening are at least partially aligned;
a fulcrum of the sleeve adjacent the sleeve aperture for supporting the second tool with the distal end portion thereof inserted through the at least partially aligned sleeve aperture and tubular member opening for urging the sleeve and the spinal rod toward the coupling member relative to the tubular member;
a proximal positioning portion of the first tool;
an upper axial guide portion of the sleeve configured to receive the first tool proximal positioning portion as the locking device is lowered through the tubular member passage and into the coupling member; and
a rotary guide portion of the sleeve disposed below the upper axial guide portion that is configured to permit the first tool positioning portion to be turned relative to the sleeve once the locking device has been advanced into the coupling member and restrict turning of the first tool positioning portion beyond a predetermined rotary position relative to the sleeve.

9. The minimally invasive surgical system of claim 8 wherein a distance between the fulcrum and the outer wall of the tubular member is greater than a distance between the outer wall of the tubular member and the sleeve when the sleeve is positioned around the tubular member and contacts the spinal rod.

10. The minimally invasive surgical system of claim 8, wherein the fulcrum includes a depression that guides the second tool into the sleeve through aperture.

11. The minimally invasive surgical system of claim 8, wherein the sleeve includes an opening sized to accommodate the fulcrum of an adjacent sleeve when the two sleeves are brought into close proximity with each other.

12. The minimally invasive surgical system of claim 8 wherein the first tool is a rotary drive tool and the second tool is a lever tool.

13. The minimally invasive surgical system of claim 8 wherein the rotary guide portion of the sleeve includes a circumferentially extending closed-ended slot and the proximal positioning portion of the first tool includes a member connected to the elongate shaft and extending transversely thereto that is configured to fit in and travel along the slot with the member engaging the end of the slot to limit turning of the first tool.

14. The minimally invasive surgical system of claim 8 further comprising a handle connected to the sleeve.

15. A minimally invasive surgical system for manipulating a fixation member relative to an anchor secured in a bone, the system comprising:
   a tubular member having a longitudinally extending passage and an outer wall with an aperture extending through the outer wall, the tubular member configured to be releasably engageable to the anchor;
   a sleeve sized to be positioned around the tubular member and contact the fixation member, the sleeve having an aperture alignable with the aperture in the tubular member when the sleeve is positioned around the tubular member, the sleeve having a ledge extending outward from the exterior of the sleeve and positioned adjacent the sleeve aperture to provide a fulcrum for a tool insertable through both apertures when the apertures are at least partially aligned for urging the sleeve and the fixation member toward the anchor relative to the tubular member;
   a second tubular member releasably engageable to a second anchor;
   a receiving member connected to the exterior of each of the tubular members; and
   a second tool having portions configured to be removably inserted into the receiving members and shifted relative to one another to produce movement of the anchors without extending into the passages of the tubular members.

16. A method of seating a spinal rod in a pedicle screw assembly, the method comprising:
   connecting a tubular member to a coupling member of the pedicle screw assembly, the coupling member being configured to receive a spinal rod therein;
   fitting a sleeve about the tubular member and advancing the sleeve along the tubular member until a distal end of the sleeve abuts the spinal rod;
   inserting a distal portion of a lever through an aperture of the sleeve and an opening of the tubular member so that the lever extends through the sleeve aperture and the tubular member opening;
   engaging the distal portion of the lever with the tubular member adjacent the opening thereof;
   positioning an intermediate portion of the lever against a fulcrum of the sleeve that extends radially outwardly from an annular wall of the sleeve; and
   applying a force to a proximal portion of the lever to pivot the lever extending through the sleeve aperture and tubular member opening about the fulcrum while the distal portion of the lever is engaged with the tubular member and the intermediate portion of the lever is supported by the fulcrum which urges the spinal rod toward the pedicle screw assembly by exerting an upward force on the tubular member and coupling member connected thereto and a downward force on the sleeve.

17. The method of claim 16, wherein engaging the distal portion of the lever with the tubular member adjacent the opening includes engaging a hook-shaped segment of the lever with a portion of the sidewall of the tubular member adjacent the opening of the tubular member.

18. The method of claim 16 wherein applying the force to the proximal portion of the lever to pivot the lever about the fulcrum includes pivoting the lever about a surface of the fulcrum positioned above a lower end of the sleeve aperture.

19. A method of seating a spinal rod into a pedicle screw assembly, the method comprising:
   engaging a tubular member relative to the pedicle screw assembly;
   positioning a sleeve around the tubular member until a distal end of the sleeve abuts the spinal rod;
   urging the spinal rod toward the pedicle screw assembly by exerting an upward force on the tubular member and a downward force on the sleeve using a lever and a fulcrum outwardly spaced from a sidewall of the sleeve to move the sleeve toward the pedicle screw assembly;
   engaging a second tubular member to a second pedicle screw assembly and positioning a second sleeve about the second tubular member;
   inserting pins of a second tool into receiving members connected to the exterior of the sleeves; and
   adjusting a pair of handles on the second tool to manipulate the positioning of the pins and alter the distance between the tubular members.

* * * * *

UNITED STATES PATENT AND TRADEMARK OFFICE
CERTIFICATE OF CORRECTION

PATENT NO.       : 8,551,141 B2                                              Page 1 of 1
APPLICATION NO. : 12/438538
DATED            : October 8, 2013
INVENTOR(S)      : Gephart et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1135 days.

Signed and Sealed this

Fifteenth Day of September, 2015

Michelle K. Lee
*Director of the United States Patent and Trademark Office*